US007894995B2

(12) United States Patent
Jojic et al.

(10) Patent No.: US 7,894,995 B2
(45) Date of Patent: Feb. 22, 2011

(54) MOLECULAR INTERACTION PREDICTORS

(75) Inventors: Nebojsa Jojic, Redmond, WA (US); Manuel Jesus Reyes Gomez, Kirkland, WA (US)

(73) Assignee: Microsoft Corporation, Redmond, WA (US)

( * ) Notice: Subject to any disclaimer, the term of this patent is extended or adjusted under 35 U.S.C. 154(b) by 1085 days.

(21) Appl. No.: 11/538,405

(22) Filed: Oct. 3, 2006

(65) Prior Publication Data

US 2007/0192036 A1 Aug. 16, 2007

Related U.S. Application Data

(62) Division of application No. 11/356,196, filed on Feb. 16, 2006.

(51) Int. Cl.
*G01N 33/50* (2006.01)
(52) U.S. Cl. .............................. 702/19; 702/20; 702/30
(58) Field of Classification Search ........................ None
See application file for complete search history.

(56) References Cited

U.S. PATENT DOCUMENTS

| | | | |
|---|---|---|---|
| 5,933,819 | A | 8/1999 | Skolnick et al. |
| 6,861,234 | B1 | 3/2005 | Simard et al. |
| 6,895,396 | B2 | 5/2005 | Schwartz et al. |
| 7,094,555 | B2 | 8/2006 | Kwok et al. |
| 2004/0072162 | A1 | 4/2004 | Fomsagaard et al. |
| 2004/0072246 | A1 | 4/2004 | Martin et al. |
| 2004/0072249 | A1 | 4/2004 | Hoffman et al. |
| 2004/0137537 | A1 | 7/2004 | Montero-Julian et al. |
| 2005/0074809 | A1 | 4/2005 | Brusic |
| 2005/0074813 | A1 | 4/2005 | Nauss et al. |
| 2005/0079549 | A1 | 4/2005 | Castracane |
| 2005/0095655 | A1 | 5/2005 | Montero-Julian et al. |
| 2006/0057673 | A1 | 3/2006 | Liu et al. |
| 2006/0084116 | A1 | 4/2006 | Muchhal |
| 2006/0111554 | A1 | 5/2006 | Lasters et al. |
| 2006/0160071 | A1 | 7/2006 | Heckerman et al. |
| 2006/0257944 | A1 | 11/2006 | Fridman et al. |
| 2007/0005262 | A1 | 1/2007 | Gershoni et al. |
| 2007/0154953 | A1 | 7/2007 | Brunner et al. |

FOREIGN PATENT DOCUMENTS

| WO | WO9859244 A1 | 12/1998 |
|---|---|---|
| WO | WO 0220564 A2 | 3/2002 |
| WO | 2005038429 A2 | 4/2005 |

OTHER PUBLICATIONS

Jain (Journal of Computer-Aided Molecular Design, 10, p. 427-440, 1996).*
Jurs et al. (Computer-Assisted Drug Design, Chapter 4, p. 103-129, ACS Symposium Series, vol. 112, 1979).*
Qu et al. (ISMB-98 Proceedings, American Association for Artificial Intelligence, pp. 9, 1998).*
Waterhouse et al. ("Classification and regression using mixtures of experts", Ph.D. Thesis, University of Cambridge, pp. 215, 1997).*
Espadaler et al. (Bioinformatics, vol. 21, No. 16, p. 3360-3368, 2005).*
Kratochwil, Nicole A. et al. Predicting plasma protein binding of drugs: a new approach. Biochemical Pharmacology. Nov. 1, 2002, vol. 64, Issue 9, pp. 1355-1374.
Rubin, G. M. et al. An expectation maximization algorithm for training hidden substitution models. Journal of Molecular Biology. Apr. 12, 2002, vol. 317, Issue 5, pp. 753-764.
International Search Report and Written Opinion dated Oct. 9, 2008 for PCT Application Serial No. PCT/US2008/060945, 11 Pages.
Brusic, et al. "Prediction of MHC Binding Peptides Using Artificial Neural Networks", Complexity International, Apr. 1995, vol. 02, http://www.complexity.org.au/ci/vol02/vbb/vbb.html, last accessed Jan. 24, 2007, 10 pages.
Peters, et al. "A Community Resource Benchmarking Predictions of Peptide Binding to MHC-I Molecules", http://mhcbindingpredictions.immuneepitope.org/manuscript.pdf, accessed Jan. 24, 2007, 51 pages.
Yanover, et al. "Predicting Protein-Peptide Binding Affinity by Learning Peptide-Peptide Distance Functions", Predicting Binding Affinity by Learning Distance Functioning, pp. 456-471, last accessed Jan. 24, 2007, Recomb 2005, LNBI 3500, p. 456-471 2005.
Zhu, et al. "Improving Prediction of MHC Class I Binding Peptides with Additional Binding Data", https://www.jsbi.org/journal/GIW04/GIW04P127.pdf, last accessed Jan. 24, 2007, 2 pages.
Hertz, et al. PepDist: a new framework for protein-peptide binding prediction based on learning peptide distance functions. BMC Bioinformatics. Mar. 20, 2006;7 Suppl 1:S3.
Sette, et al. Nine major HLA class I supertypes account for the vast preponderance of HLA-A and -B polymorphism, Immunogenetics, Nov. 1999 50:201-212.
Jones, et al. "A new approach to protein fold recognition," Nature (1992) 358:86-89.
Melo, et al. "Statistical potentials for fold assessment," Protein Science (2002) 11:430-448.
Chang, et al. Predicting peptides bound to I-Ag7 class II histocompatibility molecules using a novel expectation-maximization alignment algorithm. Proteomics 2007, 7, 367-377.
Jojic, et al. "Topographic transformation as a discrete latent varaible," Neural Information Processing Systems (NIPS) '99, Nov. 1999, Denver, CO.

(Continued)

Primary Examiner—Karlheinz R Skowronek
(74) Attorney, Agent, or Firm—Lee & Hayes, PLLC

(57) ABSTRACT

Adaptive threading models for predicting an interaction between two or more molecules such as proteins are provided. The adaptive threading models have one or more learnable parameters that can be learned from all or some of the available data. The available data can include data relating to known interactions between the two or more molecules, the composition of the molecules and the geometry of the molecular complex.

16 Claims, 76 Drawing Sheets

OTHER PUBLICATIONS

Stern, et al. Peptide 15-mers of defined sequence that substitute for random amino acid copolymers in amelioration of experimental autoimmune encephalomyelitis. Proc Natl Acad Sci U S A. Feb. 1, 2005;102(5):1620-5. Epub Jan. 21, 2005.

Karpenko, et al. Prediction of MHC class II binders using the ant colony search strategy. Artif Intell Med. Sep.-Oct. 2005;35(1-2):147-56.

Reche, et al. Enhancement to the RANKPEP resource for the prediction of peptide binding to MHC molecules using profiles. Immunogenetics. Sep. 2004;56(6):405-19. Epub Sep. 3, 2004.

Nielsen, et al. Improved prediction of MHC class I and class II epitopes using a novel Gibbs sampling approach. Bioinformatics. Jun. 12, 2004;20(9):1388-97. Epub Feb. 12, 2004.

Davies, et al. A novel predictive technique for the MHC class II peptide-binding interaction. Mol Med. Sep.-Dec. 2003;(9-12):220-5.

Murugan, et al. Prediction of MHC class II binding peptides based on an iterative learning model. Immunome Res. Dec. 13, 2005;1:6.

Brusic, et al. Prediction of MHC class II-binding peptides using an evolutionary algorithm and artificial neural network. Bioinformatics. 1998;14(2)121-30.

Lazaridis et al., "Effective Energy Functions for Protein Structure Prediction", Theory and Simulation, http://www.sci.ccny.cuny.edu/~themis/curropin.pdf, last accessed Jan. 24, 2007, 7 pages, Current opinion in structural biology, 2000 10: 139-145.

Lilien, et al. "A Novel Ensemble Based Scoring and Search Algorithm for Protein Redesign, and Its Application to Modify the Substrate Specificity of the Gramicidin Synthetase a Phenylalanine Adenylation Enzyme", http://delivery.acm.org/.10.1145/980000/974622/p46-lilien.pdf?key1=974622&key2=3858269611&coll=GUIDE&dl=GUIDE&CFID=75919783&CFTOKEN=92791909, last accessed Jan. 24, 2007, 12 pages, Recomb '04 Mar. 27-31, 2004.

Zhao, et al. "Application of Support Vector Machines for T-cell Epitopes Prediction", Bioinformatics, Apr. 7, 2003, vol. 19, No. 15 2003, pp. 1978-1984, http://bioinformatics.oxfordjournals.org/cgi/reprint/19/15/1978, last accessed Jan. 24, 2007, 7 pages.

Lee, et al. Biophysical Chemistry, vol. 115, p. 209-214. Jan. 6, 2005.

Deng, et al. J. Chem. Inf. Comput. Sci. vol. 44, pp. 699-703, 2004.

Park, et al. Proteins, vol. 40, pp. 237-248. 2000.

Marshall, et al. Proteomics and Protein-Protein Interactions: Biology chemistry, bioinformatics and Drug Design, Chapter 2, pp. 115-146. 2005.

Altuvia, et al. Methods, vol. 34, pp. 454-459. 2004.

Wiesmuller, et al. Biol. Chem. vol. 382, pp. 571-579. 2001.

Miyazawa, et al., J. Mol. Biol., vol. 256, p. 623-644, 1996.

specific weight. (1992). In Academic Press Dictionary of Science and Technology. Retrieved Jun. 25, 2008, from http://www.credoreference.com/entry/3161132.

density. (1992). In Academic Press Dictionary of Science and Technology. Retrieved Jun. 25, 2008, from http://www.credoreference.com/entry/3094286.

OA mailed Jul. 7, 2008 for U.S. Appl. No. 11/356,196, 22 pages.

O. Schueler-Furman, et al., "Structure-based prediction of binding peptides to MHC class I molecules: Application to a broad range of MHC alleles," Protein Science, 2000, pp. 1838-1846, vol. 9.

A. Sette, et al., "Peptide binding to the most frequent HLA-A class I alleles measured by quantitative molecular binding assays," Molecular Immunology, 1994, pp. 813-822, vol. 31, No. 11.

M. Bhasin, et al., "MHCBN: A comprehensive database of MHC binding and non binding peptides," Bioinformatics, 2003, pp. 665-666, vol. 19, No. 5.

H. Rammensee, et al., "SYFPEITHI: database for MHC ligands and peptide motifs," Immmunogenetics, 1999, pp. 213-219, vol. 50.

C. Moore, et al., "Evidence of HIV-1 Adaptation to HLA-Restricted Immune Responses at a Population Level," Science, May 24, 2002, pp. 1439-1443, vol. 296.

C. Yanover, et al., "Predicting protein-peptide binding affinity by learning peptide-peptide distance functions," Recomb, 2005, pp. 456-471.

K. Arien, et al., "Replicative fitness of historical and recent HIV-1 isolates suggest HIV-1 attenuation over time," AIDS, Oct. 14, 2005, pp. 1555-1564, vol. 19.

N. Jojic, et al., "Using "epitomes" to model genetic diversity: Rational design of HIV vaccine cocktails,", in Advances in Neural Information Processing Systems 18, Presented at NIPS 2005, 8 pages.

N. Jojic, et al., "Learning MHC I-peptide binding", Bioinformatics, vol. 22 No. 14 2006, pp. e227-e235.

H. Singh, et al., "ProPred: prediction of HLA-DR binding sites", Bioinformatics Applications Note, vol. 17, No. 12, 2001, pp. 1236-1237.

Altuvia et al. (1997). Human Immunology, vol. 58, pp. 1-11.

Wojciechowski et al. (2001). J. Comput. Chem., vol. 23, pp. 189-197.

Freire, "Thermodynamics of protein folding and molecular recognition", IUPAC, Pure & Applied Chemistry, vol. 69, No. 11, 1997, pp. 2253-2261.

Guler, "A Model With an Intrinsic Property of Learning Higher Order Correlations", Neural Networks, vol. 14, 2001, pp. 495-504.

Mamitsuka, "Predicting Peptides That Bind to MHC Molecules Using Supervised Learning of Hidden Markov Models", PROTEINS: Structure, Function, and Genetics 33, Wiley-Liss, Inc., 1998, pp. 460-474.

Neal, "NIPS (Neural Information Processing Systems)", NIPS 2004 Conference, Dec. 2004.

Nielsen, et al., "Reliable Prediction of T-cell epitopes using neural networks with novel sequence representations", Protein Science, The Protein Society, Cold Spring Harbor Laboratory Press, 2003, pp. 1007-1017.

Swain, et al., "An automated approach to modelling class II MHC alleles and predicting peptide binding", retrieved on Aug. 19, 2009 at <<http://ieeexplore.ieee.org/search/wrapper.jsp?arnumber=974415>>, Bioinformatics and Bioengineering Conference 2001, Proceedings of the IEEE 2nd Int Symposium, 2001, pp. 81-88.

Zhang, et al., "Consistency in structural energetics of protein folding and peptide recognition", Protein Science 6, Cambridge University Press, 1997, pp. 1057-1064.

Brusic, et al., "Prediction of Promiscuous Peptides that Bind HLA Class I Molecules", Immunology and Cell Biology, 2002, vol. 80, Issue 3, pp. 280-285.

Heckerman, et al., "Leveraging Information Across HLA Alleles/Supertypes Improves Epitope Prediction", Springer Berlin/Heidelberg, Research in Computational Molecular Biology, Lecture Notes in Computer Science, 2006, vol. 3909, pp. 296-308.

Jacob, et al., "Epitope Prediction Improved by Multitask Support Vector Machines", Retrieved on Feb. 6, 2007, Available at <<http://hal.archives-ouvertes.fr/docs/00/12/90/62/PDF/mtkepitope-jacob-vert.pdf>>, 18 pgs.

Lee, et al., "Learning With Positive and Unlabeled Examples Using Weighted Logistic Regression", In the Proceedings of the Twentieth International Conference on Machine Learning, 2003, 8 pgs.

Rousseeuw, et al., "Robustness Against Separation and Outliers in Logistic Regression", Elsevier Science Publishers B.V., Computational Statistics & Data Analysis, 2003, vol. 43, Issue 3, pp. 315-332.

Tandon, et. al., "Predicting Continuous Epitopes in Proteins", IEEE, In the Proceedings of the Computational Systems Bioinformatics Conference, 2005, pp. 133-134 (2 pgs.).

Williams, et al., "Incomplete-Data Classification Using Logistic Regression", ACM, In the Proceedings of the 22nd International Conference on Machine Learning, 2005, pp. 972-979.

Xiao, et al., "Prediction of Genomewide Conserved Epitope Profiles of HIV-1: Classifier Choice and Peptide Representation", Statistical Applications in Genetics and Molecular Biology, 2005, vol. 4, Issue 1, Article 25, 36 pgs.

Bhasin et al., "Pcleavage: an SVM based method for prediction of constitutive preteasome and immunoproteasome cleavage sites in antigenic sequences", Nucleic Acids Research, 2005. vol. 33, Web Server issue, 6 pages.

International Search Report and Written Opinion dated Oct. 9, 2008 for PCT Application Serial No. PCT/US20081060945, 11 Pages.

Panchenko et al., "Combination of Threading Potentials and Sequence Profiles Improves Fold Recognition", Journal of Molecular Biology 296, 2000, 13 pages.

Peters et al., "The Immune Epitope Database and Analysis Resource: From Vision to Blueprint", PLoS Biology, Mar. 2004, vol. 3, Issue 3, 3 pages.

Schmidler et al., "Bayesian Segmentation of Protein Secondary Structure", Journal of Computational Bilogy, vol. 7, Nos. 1/2, 2000, pp. 233-248.

Florea, et al., "Epitope Prediction Algorithms for Peptide-based Vaccine Design", Computer Society, In the Proceedings of the Computational Systems bioinformatics, 2003, 10 pages.

Gotoh, "Multiple Sequence Alignment: Algorithm and Applications", Advanced Biophysics, 1999, vol. 36, pp. 159-206.

Lund, et al., "Definition of Supertypes for HLA Molecules Using Clustering of Specificity Matrices", Immunogenetics, vol. 55, No. 12, 2004, pp. 797-810.

Tsuda, et al., "Marginalized Kernels for Biological Sequences", Bioinformatics, 2002, vol. 18, Supplement 1, pp. S268-S275.

* cited by examiner

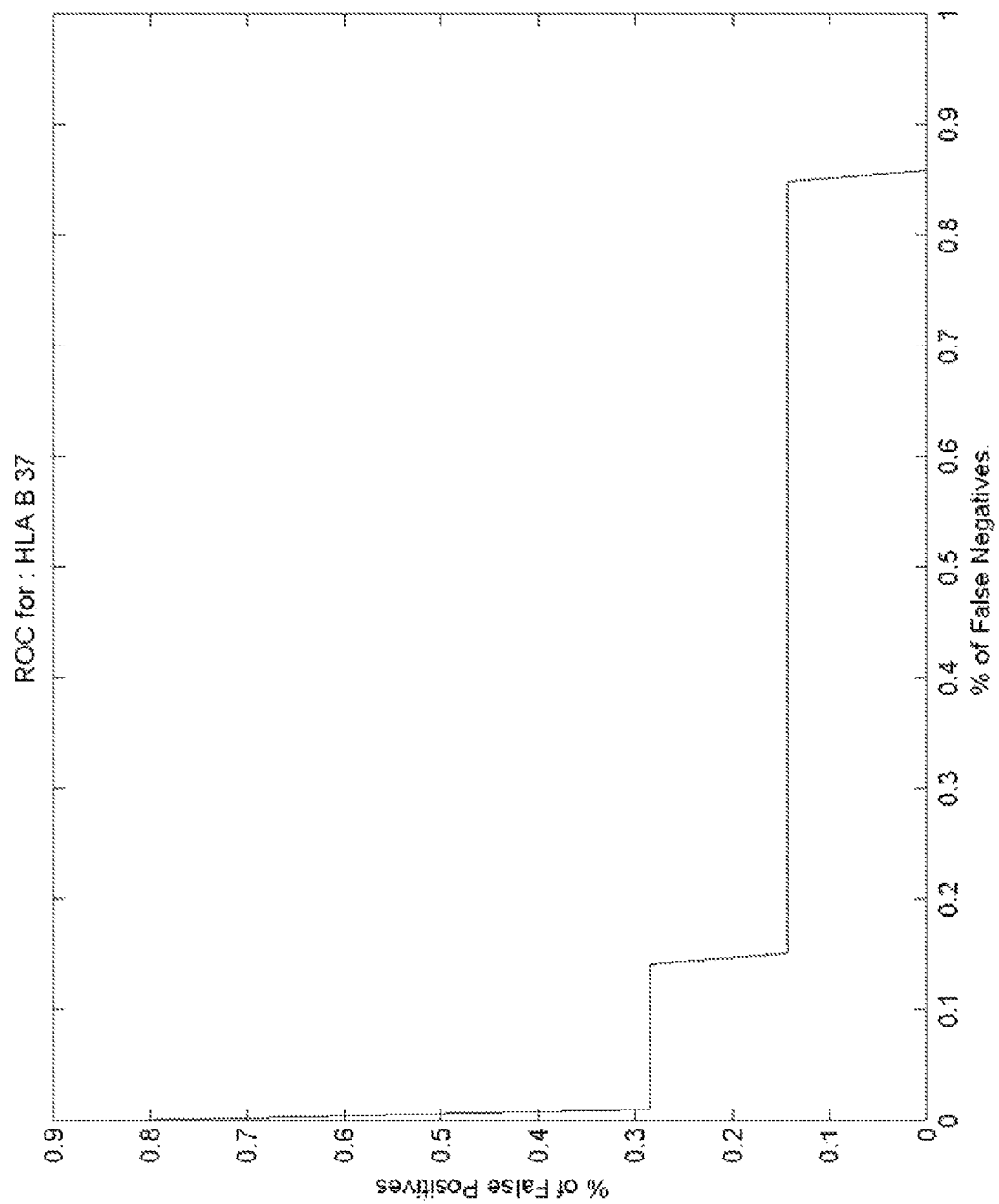

MOLECULAR INTERACTION PREDICTORS

CROSS REFERENCE TO RELATED APPLICATIONS

This application is a divisional of U.S. patent application Ser. No. 11/356,196, filed on Feb. 16, 2006, and entitled MOLECULAR INTERACTION PREDICTORS. This application is related to U.S patent application Ser. No.11/538,413 filed on Oct. 3, 2006, and entitled MOLECULAR INTERACTION PREDICTORS. The entireties of the aforementioned applications are incorporated herein by reference.

BACKGROUND

Living organisms possess various mechanisms for preventing disease states. For instance, the vertebrate immune system provides both humoral-mediated and cellular-mediated immunological defenses. As part of the cellular arm, cytotoxic CD8+ T cells kill infected cells if they recognize short peptides (amino acid subsequences) from a pathogenic protein, which are presented within the Major Histocompatibility Complex class 1 (MHC-1) molecules on a cell's surface. Most human cells create such short peptides by a process that trims proteins down to a length of 8-11 amino acids suitable for binding to MHC-I molecules, or around 20 amino acids suitable for binding to MHC-II. The MHC molecules bind to some of the processed peptides (referred to as epitopes) and present them on the surface of the cell where the cells of the immune system can encounter and recognize the epitopes. The particular epitopes that can be presented by a cell depend on the type of MHC molecules expressed by the organism.

The human MHC molecules are also often referred to as the Human Lymphocyte Antigen (HLA) molecules. MHC-I (HLA-1) molecules are encoded in three regions of the human genome, labeled A, B, and C. Since each individual inherits genes from two parents, each individual expresses from three to six different MHC molecules. The regions of the genome that code for MHC molecules are among the most variable in the human genome. The diversity is concentrated in those nucleotide sequences coding for the groove region of the MHC molecule where an epitope binds to the MHC molecule.

Since different MHC molecules typically bind to different peptides, it is very important clinically to classify MHC types. For example, organ transplant recipients may reject organs received from donors with different MHC types because the cells in these transplanted organs will present MHC-peptide complexes that are new to the immune system of the recipient. Modern MHC typing is performed by sequencing, and the sequence data for all known MHC variants is publicly available.

The interaction between an MHC molecule and a peptide (or any two molecules) can be characterized by a binding free energy. The lower the binding free energy, the greater the affinity between the two proteins. The binding free energy is the difference between the free energy of the bound and unbound states. The binding energy for an MHC-peptide complex can be directly measured by competition experiments with a standard peptide. It is expressed as the ratio between the half-maximal inhibitory concentration (IC50) of the standard peptide to that of the test peptide. In the context of MHC-peptide binding, IC50 is the concentration of the test peptide required to inhibit binding of the standard peptide to MHC by 50%. The result of such experiments is a set of relative binding energies (negative logarithms of the relative concentrations), for different MHC-peptide combinations.

Despite significant progress over the last few years, predicting 3-D protein structure and binding remains difficult to solve problems. Research in this area has focused on complex physics-based models using a large number of particles to describe not only the amino acids in the proteins, but also the solvent that surrounds them. One example of a structural model that can be used to predict peptide-MHC affinity is the threading model. The threading model is based on the premise that proteins fold in a finite number of ways and that the change in the short peptide that binds to MHC does not dramatically influence the 3-D binding configuration. Therefore, instead of screening all theoretically possible ways a particular sequence can fold and bind to another peptide to properly choose the sequence's 3-D structure, the protein binding configurations that are already known are used to compute the binding energy (or affinity).

Due to the importance of MHC complexes, many structures of MHC-peptide binding configurations have been obtained by crystallographers. Since x-ray crystallography reveals that MHC-peptide complexes exhibit a finite number of conformations, the threading approach can be applied to the problem of predicting MHC-peptide binding. The threading approach assumes that energy is additive, but it introduces a simplification that allows estimation of the binding energy of a peptide with an MHC molecule whose 3-D configuration of binding with some other peptide is known. In particular, the assumption is that the binding energy is dominated by the potentials of pairwise amino acid interactions that occur when the amino acids are in close proximity (e.g., distance smaller than 4.5 Å). Another assumption underlying the threading approach is that the proximity pattern of the peptide in the groove (i.e., MHC binding site) does not change dramatically with the peptide's amino acid content. As the pairwise potentials are assumed to depend only on the amino acids themselves and not on their context in the molecule, the energy becomes a sum of pairwise potentials taken from a symmetric 20×20 matrix of pairwise potentials between amino acids. These parameters are computed based on the amino acid binding physics and there are several published sets derived in different ways.

The MHC-peptide threading procedure utilizes solved MHC-peptide complexes as the threading template, a definition of interacting residues and a pairwise contact potential table. To predict MHC-peptide binding, the query sequence is "threaded" through the various known MHC structures to find the best fit. These structural data files are available, for instance, from the Research Collaboratory for Structural Bioinformatics (RCSB) protein data bank. The algorithm for the threading model proceeds as follows. Given a known structure of an MHC-peptide complex, the contacting MHC residues for each peptide position are determined. The amino acid-amino acid pairwise potentials are used to score the interaction of a peptide amino acid at a certain position with all its contacting residues. Assuming position independence, the peptide's score is the sum of the amino acid scores.

An example of an MHC-peptide complex is given in FIG. 1, which shows the 3-D structure of MHC A0201 bound to a peptide. The peptide amino acid centroids are marked in 3-D space by triangles and the centroids of the MHC amino acids are marked by circles. The MHC amino acids that are in proximity (<4 Å) of the peptide are marked by filled circles.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The subject matter described herein utilizes machine learning techniques to predict molecular interactions. By way of example, a threading model can be expressed as one or more parametric functions having learnable parameters. The parameters can be estimated from available data and the trained adaptive threading model can be used to predict molecular interactions. The available data can be of any type suitable for the particular molecules under study. For instance, if the adaptive threading model is used to predict protein-protein (e.g., MHC-peptide, receptor-ligand, antibody-antigen, etc.) binding energies, the parameters can be estimated from the protein sequences, 3-D protein-protein complex structural data and known binding energies (continuous or threshold) for similar protein-protein complexes. Knowledge of epitopes includes knowledge of threshold or binary energy data. For peptides that are epitopes, this implies low binding energy. If the IC50 or some other continuous measure of binding affinity is not known, other sources of binding data can be used. For instance, for some peptides, the information in the published literature can be used to determine whether they are or are not epitopes even though their exact binding energy is not known. In these cases, binary (low or high) information about binding energy can be used.

The adaptive model can infer unknown data using machine learning techniques. The learnable parameters can be, for instance, contact potentials, weights and distance function parameters. Any suitable machine learning technique can be used to estimate the parameters and infer unknown variables and parameters so as to maximize the fit of the known data to the model (e.g., iterative optimization, iterative least squares, expectation maximization (EM), generalized expectation maximization (GEM), variational expectation maximization (VEM), gradient descent, conjugate gradient descent, etc.).

The subject matter can be used to not only identify molecules with very low binding energies (i.e., good binders such as epitopes), but also to rank the molecules having intermediate levels of binding. The model significantly outperforms the standard threading approach in binding energy prediction. The subject matter also can be used to identify the effects of host immune pressure on pathogen evolution (e.g., HIV sequence evolution within a host and on a population level).

The following description and the annexed drawings set forth in detail certain illustrative aspects of the subject matter. These aspects are indicative, however, of but a few of the various ways in which the subject matter can be employed and the claimed subject matter is intended to include all such aspects and their equivalents. For ease of description, MHC-peptide binding energies have been selected to illustrate how the subject matter can be employed. However, the subject matter facilitates making predictions about any molecular binding configuration, especially protein-ligand binding or other situations in which a family of similar molecules have been documented to bind to a variety of molecules of interest and is not limited only to predicting MHC-peptide binding energies. A ligand can be any molecule (especially a small molecule, such as a peptide) that binds to another.

BRIEF DESCRIPTION OF THE DRAWINGS

FIGS. 18a-f show ROC curves demonstrating the performance of an adaptive threading predictor trained on data from over 50 MHC molecules.

DETAILED DESCRIPTION

Figure 1:
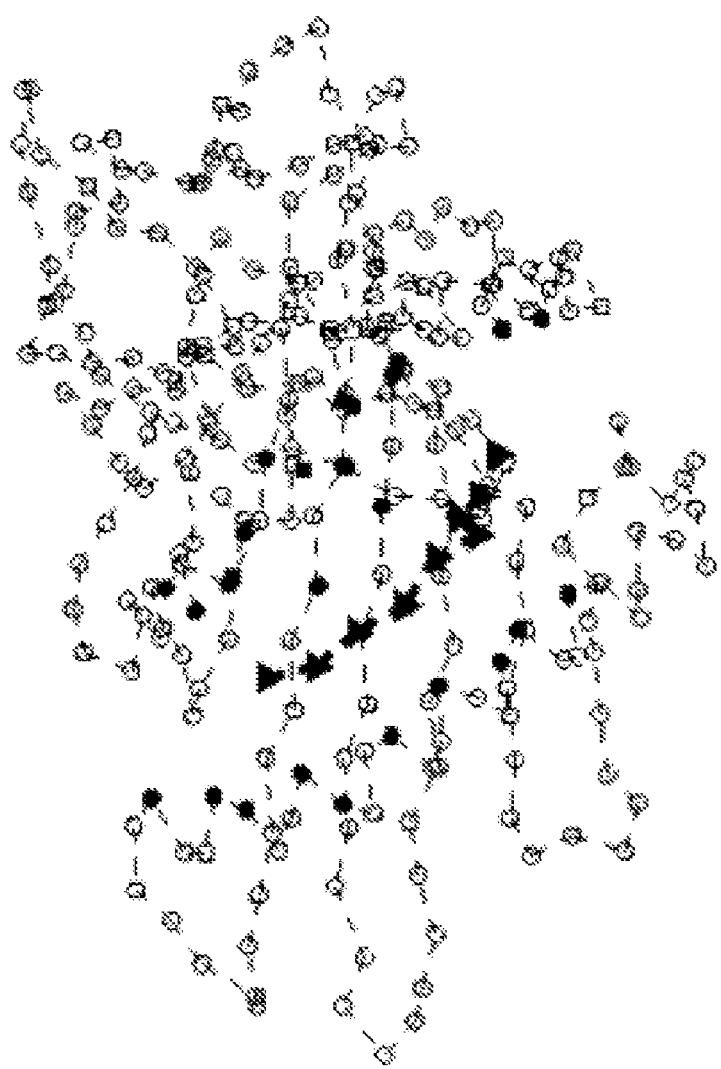
FIG. 1 schematically illustrates the 3-D structure of MHC A0201 bound to a peptide.
Figure 2:
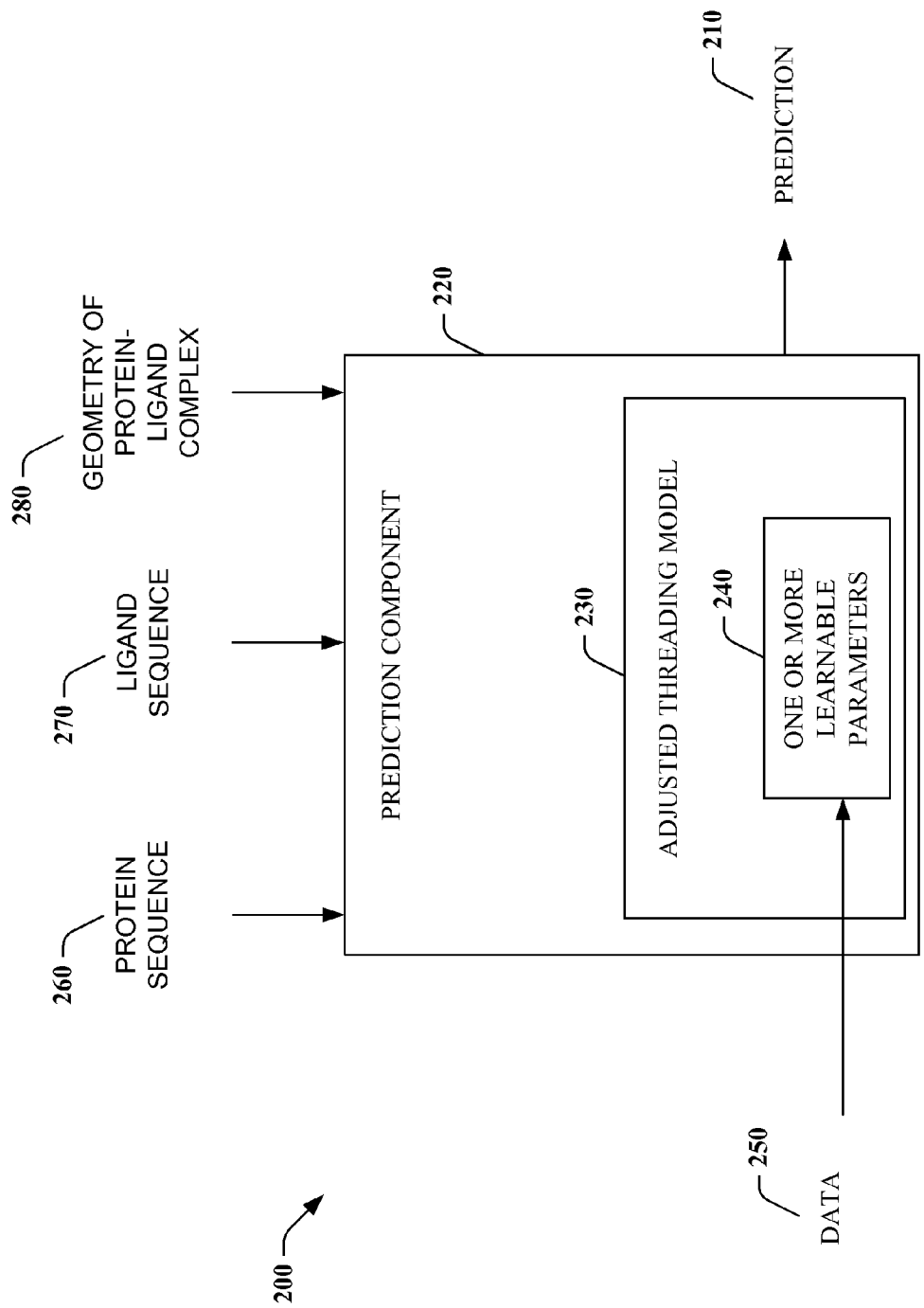
FIG. 2 is a block diagram of one example of a system that facilitates making a prediction relating to a molecular interaction.

FIG. 2 schematically illustrates an exemplary system 200 that facilitates making a prediction 210 relating to an interaction between a protein and a ligand. One example of such a system 200 utilizes a prediction component 220 employing an adjusted threading model 230 having one or more learnable parameters 240 that are estimated using available direct or indirect data 250 (either separately or jointly) about molecular binding. The system 200 makes the prediction 210 utilizing the estimated learnable parameters 240, information about the protein's sequence 260, information about the ligand's sequence 270 and information about the geometry of the protein-ligand complex 280 (e.g. MHC-peptide complexes, T-cell receptor-ligand, antibody-antigen, etc.).

By way of example, the adjusted threading model 230 can be used to make a prediction 210 about the binding energy of an MHC-peptide complex as a function of the MHC sequence and the peptide sequence. One way to accomplish this is to add learnable parameters 240 to a general mathematical definition of a threading model expressed as follows:

$$E(m, s, e) \approx \sum_i \sum_j \phi_{s_i, e_j} h(d_{i,j}^m) \quad (1)$$

where i is a sequence position in the MHC molecule having sequence s and j is a sequence position in the peptide having sequence e, $\phi$ is a pairwise contact potential, and $d_{i,j}^m$ is the distance between the i-th amino acid of the MHC molecule and the j-th amino acid of the peptide in the m-th known 3-D structure. The distances $d_{i,j}^m$ are obtained from the 3-D structural data. The structural data can be, for instance, the 3-D coordinates of the amino acids of an MHC-peptide complex obtained by crystallography. A distance $d_{i,j}^m$ can be, for instance, the distance between an atom in the side chain of the i-th amino acid in the m-th MHC molecule and any atom in the j-th amino acid in the peptide. Function h is the step function:

$$h(d) = \begin{cases} 1, & d \leq d_{thr} \\ 0, & d > d_{thr} \end{cases} \quad (2)$$

where $d_{thr}$ is a threshold distance. If the i-th amino acid of the MHC molecule and the j-th amino acid of the peptide are not at least as close the threshold distance, the amino acids do not contribute to the binding energy E. The parameter $d_{thr}$ is typically hand chosen to be about 4-4.5 Å.

Figure 3:
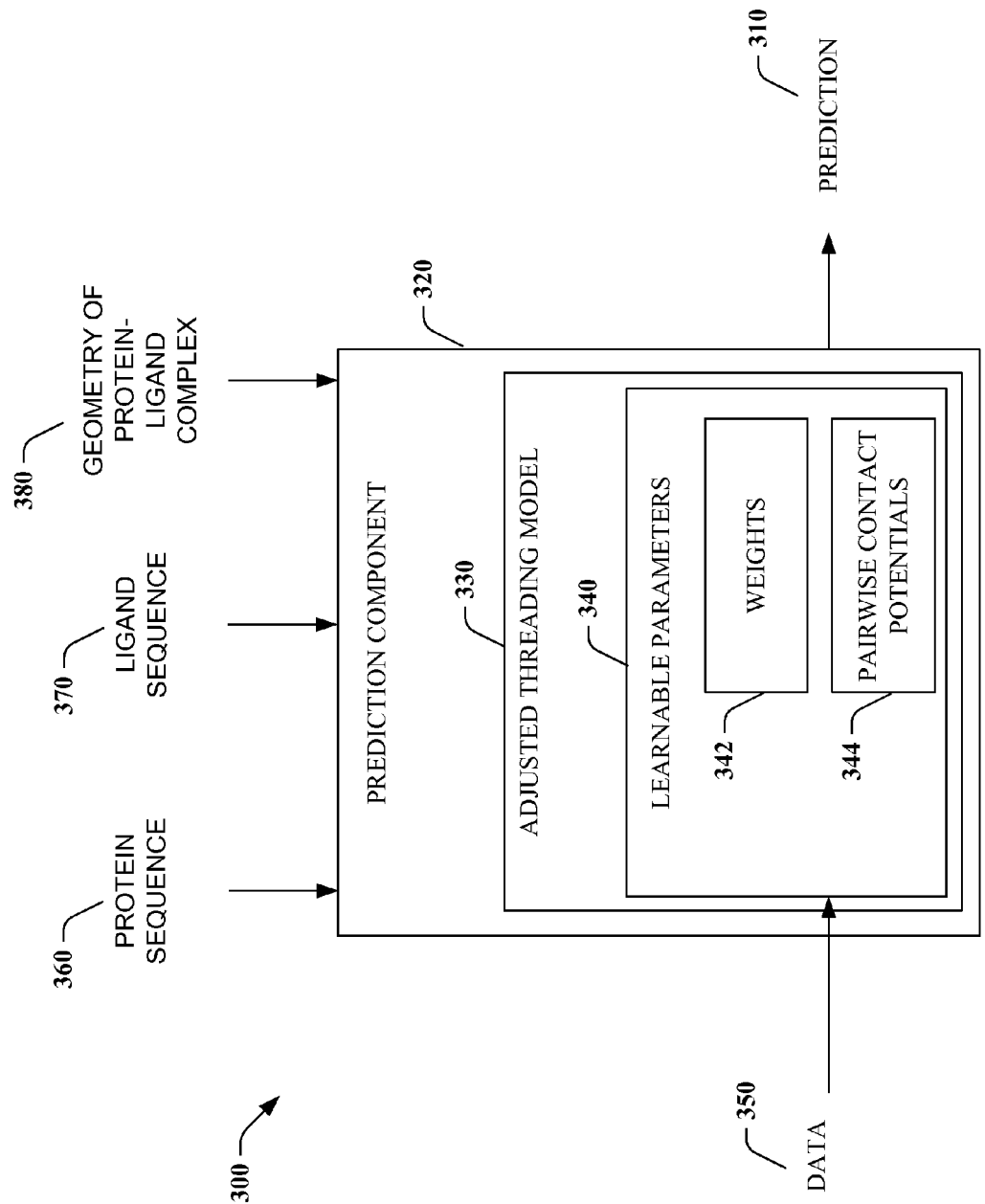
FIG. 3 is a block diagram of another example of a system that facilitates making a prediction relating to a molecular interaction.

In order to use the abundant direct or indirect information about binding to improve the threading model, the threading equation given in Equation 1 can be adjusted by adding one or more learnable parameters. As shown in FIG. 3, the learnable parameters 340 can be learnable weights 342 and pairwise contact potentials 344. By way of example, learnable MHC-specific weights 342 ($w_{i,j}^m$) and learnable pairwise contact potentials 344 ($\phi_{s_i, e_j}$) can be added to the threading equation as follows:

$$E(m, s, e) \approx \sum_i \sum_j w_{i,j}^m \phi_{s_i, e_j} h(d_{i,j}^m). \quad (3)$$

The learnable weights 342 and learnable pairwise contact potentials 344 can be estimated from the data 350 using machine learning techniques. For instance, a Bayesian network can be constructed using previously published pairwise potential matrices as a Bayesian prior on the potentials 344 to avoid overtraining. A Bayesian prior favoring $w_{ij}^{m=1}$ can be used to estimate the weights 342. Thus, the model reduces to standard threading when priors are strong enough to ignore the dataset of energies E for various peptide and MHC combinations. However, the priors can be left weak enough so that the data can dominate the learning process and the priors simply serve as a measure against over-fitting.

The data 350 utilized to learn the weights 342 ($w_{i,j}^m$) and pairwise contact potentials 344 ($\phi_{s_i, e_j}$) can be, for instance, known MHC sequences, known 3-D structures of MHC-peptide complexes, known binding energies for MHC-peptide complexes, binding energies of known non-binders (peptides that have a very high binding energy with the particular MHC molecule), and binding energies of known strong binders. The data 350 can be obtained from any suitable source. For instance, the sequence data for known MHC variants can be obtained from websites. Structural MHC-peptide data files can be obtained from the RCSB protein data bank at. MHC-peptide binding affinities can be obtained experimentally by measuring the IC50 as described above. The sequences of known binders and non-binders can be obtained from publicly available databases such as the SYFPEITHI database at, the Los Alamos National Laboratory database and the MHCBN database. These databases provide "binary" energy data for many peptides (i.e., by indicating if a peptide is a strong binder with very low binding energy or a non-binder with very high binding energy for a particular MHC type).

The dataset of measured binding energies can be directly used to train the adjusted threading model 330 but the dataset of known good binders and non-binders (i.e., binary energy) requires a treatment of missing energy values. To incorporate this data, the lowest binding energy in the measured binding energy dataset for good binders (epitopes), and similarly, the highest binding energy for the non-binders can be used. Alternatively, the spread between the binding energies of the binders and non-binders can be maximized, or a cost function (other than quadratic) that punishes high but not low binding energies for good binders and does the opposite for non-binders can be used. During training, if 3-D structural data is not available for a MHC molecule having sequence s, the distances $d_{i,j}^m$, can be defined from the available structural data file corresponding to the MHC molecule whose sequence content is the most similar to s. Using a generative approach, m can be considered as a hidden variable influencing the sequence s, thus allowing m to be machine inferred (e.g., Bayesian inference) from s. Alternatively, m can be machine inferred from both s and e. Integrating m out, exactly or approximately (e.g., by setting the most likely m that maximize the likelihood, minimizes the energy or yields the best similarity between the m-th structure's amino acid content and that of s and e) yields the resulting estimator E(s,e).

One way to estimate the learnable parameters 340 is to assume that Gaussian noise exists in the energy data 350 E and, because of the bilinear dependence of E on φ and w, fit the adjusted threading model 330 using variational learning techniques. As the optimization criterion becomes quadratic, the variational inference essentially iterates a liner regression to find the contact potential 344 variables (penalized appropriately by the prior) and a regression that estimates the weights 342 again taking into account the Gaussian prior favoring $w_{i,j}=1$.

By way of another example, since the pairwise contact potentials 344 parameters (φ) are shared across all the data 350, the model 330 can be fit to all of the structural data relating to the MHC-peptide complexes together. The weighting 342 parameters (w), however, are specific to a particular MHC molecule. Training only on a limited number of MHC molecules degrades the performance of the predictor on the test data even for the MHC molecules included in training. Joint training improves energy prediction for individual MHC types according to the equation:

$$E(m, s, e) \approx \sum_i \sum_j w_{i,j} \phi_{s_i,e_j} h(d_{i,j}^m), \quad (4)$$

where $w_{i,j}$ are MHC-independent weights 342. The data shows that MHC types for which little binding and epitope data is available can be better trained with weight sharing. The data also shows a slight degradation in energy estimation for the MHC types for which more data is available in comparison to the models having MHC type-specific weights. As more data becomes available, both the models with shared weights and type-specific weights become more precise, although the current data indicates that the type-specific models still should be slightly better. Moreover, the embodiments having shared weights allow prediction even for completely new MHC types discovered in nature or those synthesized artificially (e.g. by mutating existing MHC sequences) before any binding data is obtained for training.

Other adjustments can be made to address errors introduced by the assumptions underlying the threading model. For instance, one such assumption is that all pairs of amino acids that are in a proximity defined by h will contribute to the energy independently. When the threshold parameter $d_{thr}$ is set high (producing a very sparse set of pairs i, j that contribute to the energy), this approximation indeed renders these amino acid pairs isolated from each other. However, setting a low distance threshold $d_{thr}$ results in many interactions being left out. Raising the threshold can result in having one amino acid in the MHC molecule interacting with multiple amino acids in the peptide, in which case the additive model could be questioned.

Figure 4:
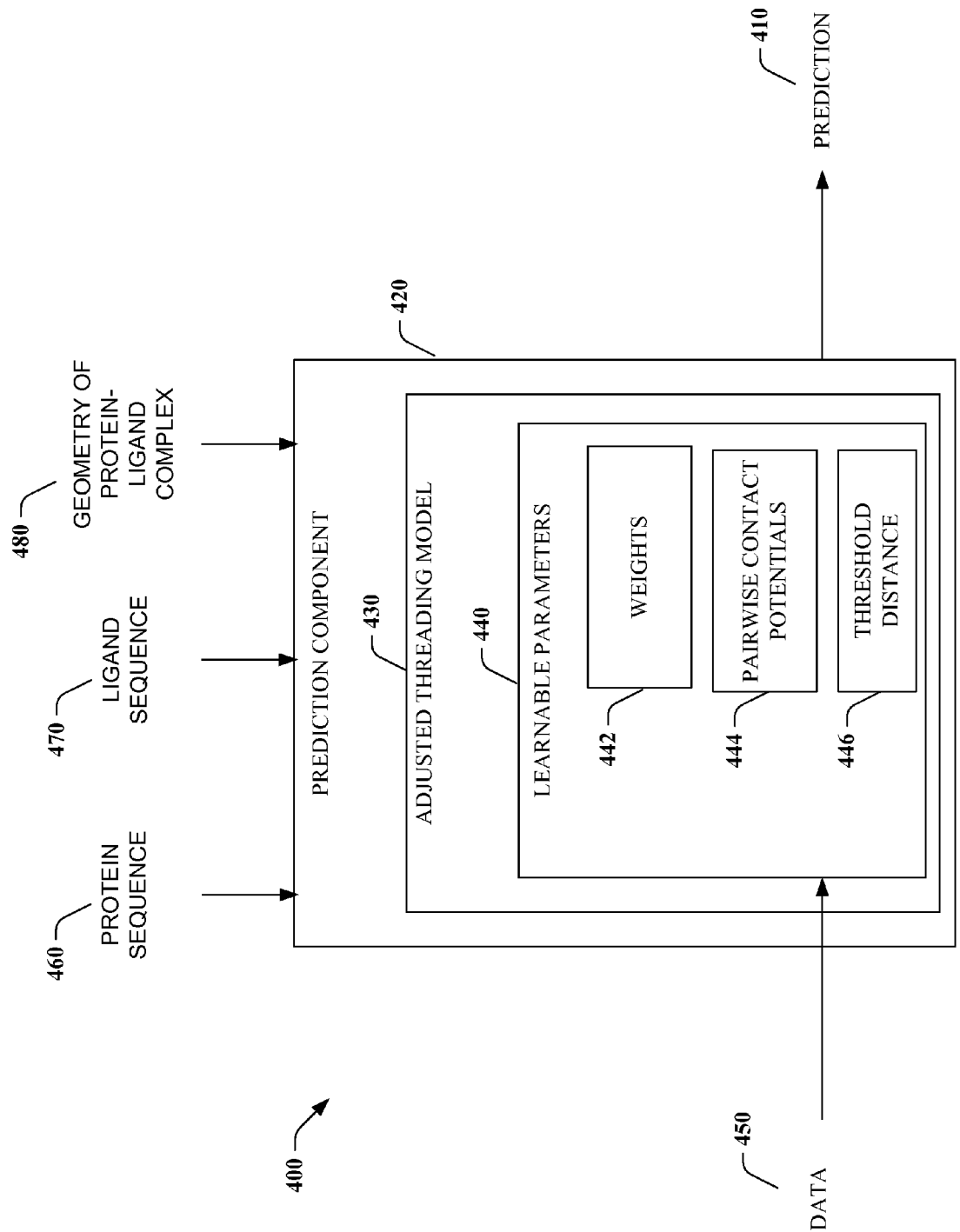
FIG. 4 is a block diagram of another example of a system that facilitates making a prediction relating to a molecular interaction.
Figure 5:
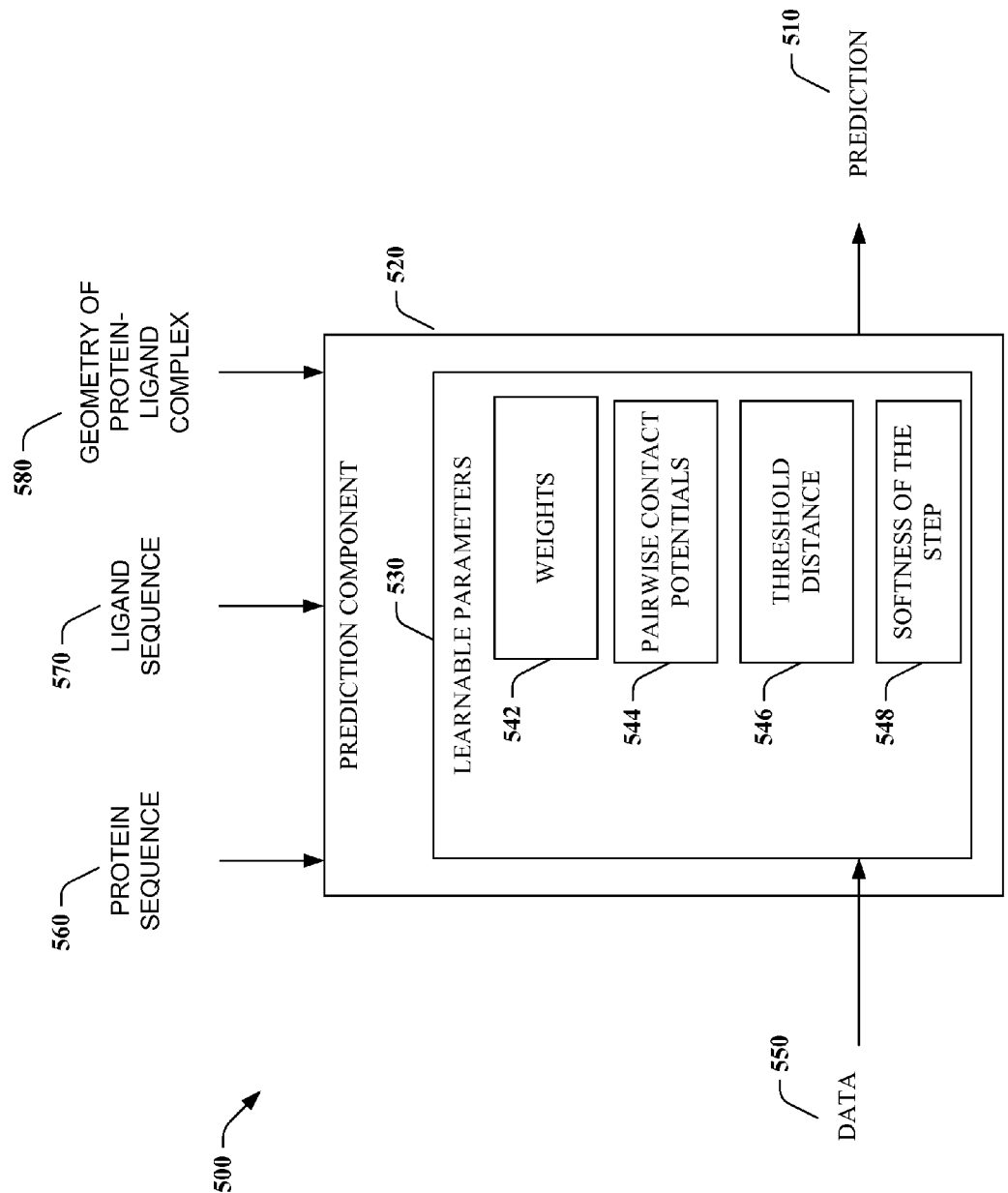
FIG. 5 is a block diagram of another example of a system that facilitates making a prediction relating to a molecular interaction.

To vitiate these errors, as shown in FIG. 4, the adjusted threading model 430 can be further adjusted, for instance, by adding a learnable threshold distance 446 to optimize the threshold distance $d_{thr}$ parameter. As shown in FIG. 5, the adjusted threading model 530 can be made more robust to slight variations in geometry by using a soft step function (e.g., sigmoid) that has a learnable softness of the step 548. This makes the predictor 520 more robust because this eliminates the problem of turning off the contribution to the energy prediction 510 of those amino acid pairs whose distance is close to the threshold but slightly above the threshold (as can occur with the hard step function). The learnable parameters 546 and 548 can be estimated to optimally set the threshold and the softness of the step. One example of such a learnable soft step function is:

$$h(d) = 1 - (1/(1 + e^{-A*(d_{i,j}^m - d_{thr})})) \quad (5)$$

where A is a parameter that determines the softness of the step function, $d_{thr}$ is the threshold distance and $d_{i,j}^m$ is the distance between the i-th amino acid of the MHC molecule and the j-th amino acid of the peptide in the m-th 3-D structure. The learnable parameters A and $d_{thr}$ can be estimated using machine learning algorithms designed to minimize the error between the predicted energies and the true energies (e.g., gradient descent).

Figure 6:
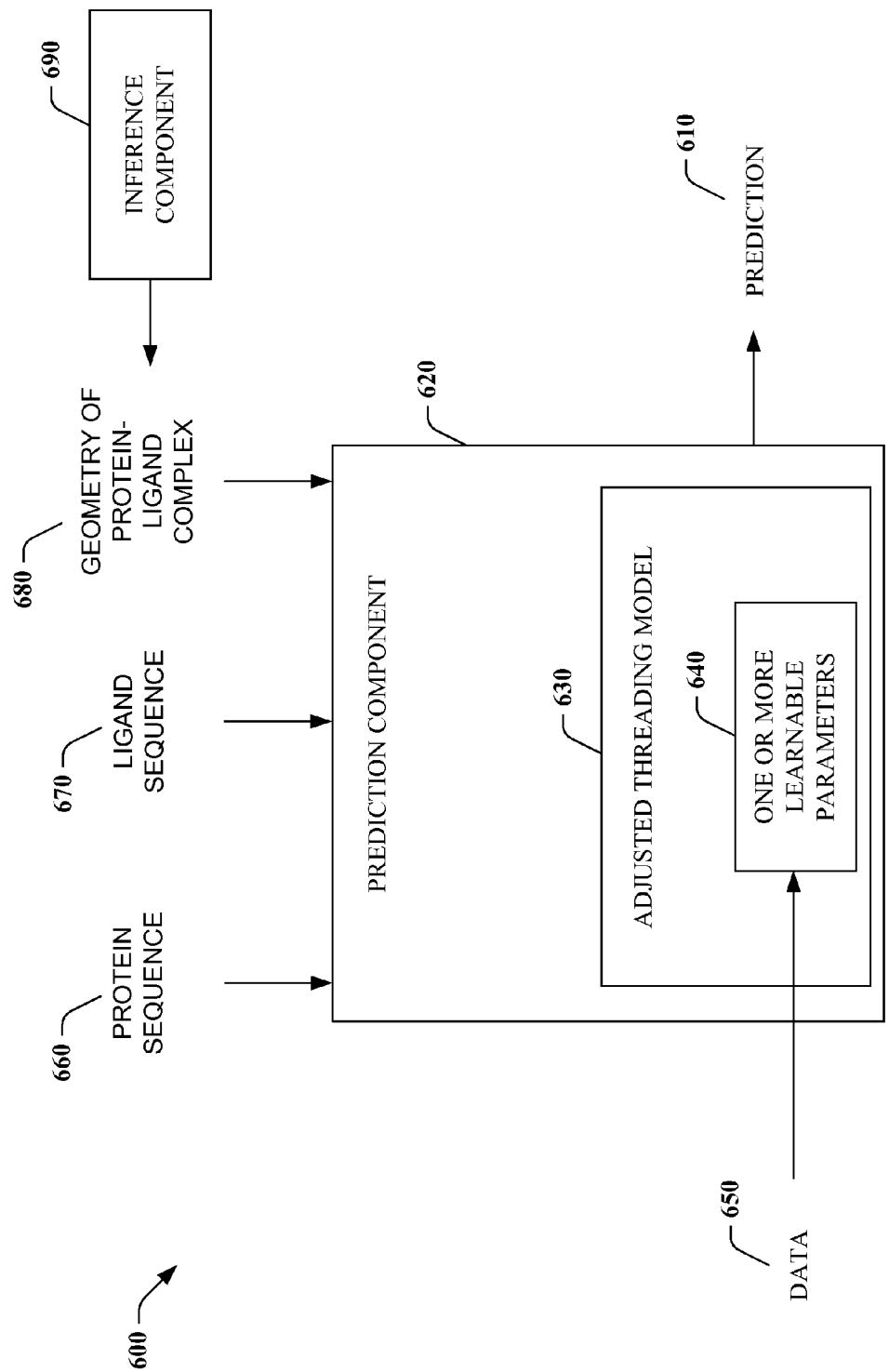
FIG. 6 is a block diagram of yet another example of a system that facilitates making a prediction relating to a molecular interaction.

As shown in FIG. 6, an inference component 690 can be used to infer information about geometry 680, and thus can facilitate making predictions 610 even when the geometry 680 is not known (e.g., unavailable data or if the molecules are synthetic). After the adjusted threading model 630 is trained on the data 650, the prediction component 620 can provide a prediction 610 even for proteins for which no data other than their sequence s is given. By way of example, if 3-D structural data is not available for a MHC molecule, the distances $d_{i,j}^m$, can be defined from the available structural data file corresponding to the MHC molecule whose sequence content is the most similar to s. Using a generative approach, m can be considered as a hidden variable influencing the sequence s, thus allowing m to be machine inferred (e.g., Bayesian inference) from s. Alternatively, m can be machine inferred from both s and e. Integrating m out, exactly or approximately (e.g., by setting the most likely m that maximizes the likelihood, minimizes the energy, or yields best similarity between the m-th structure's amino acid content and that of s and e) yields the resulting estimator E(s,e).

Figure 7:
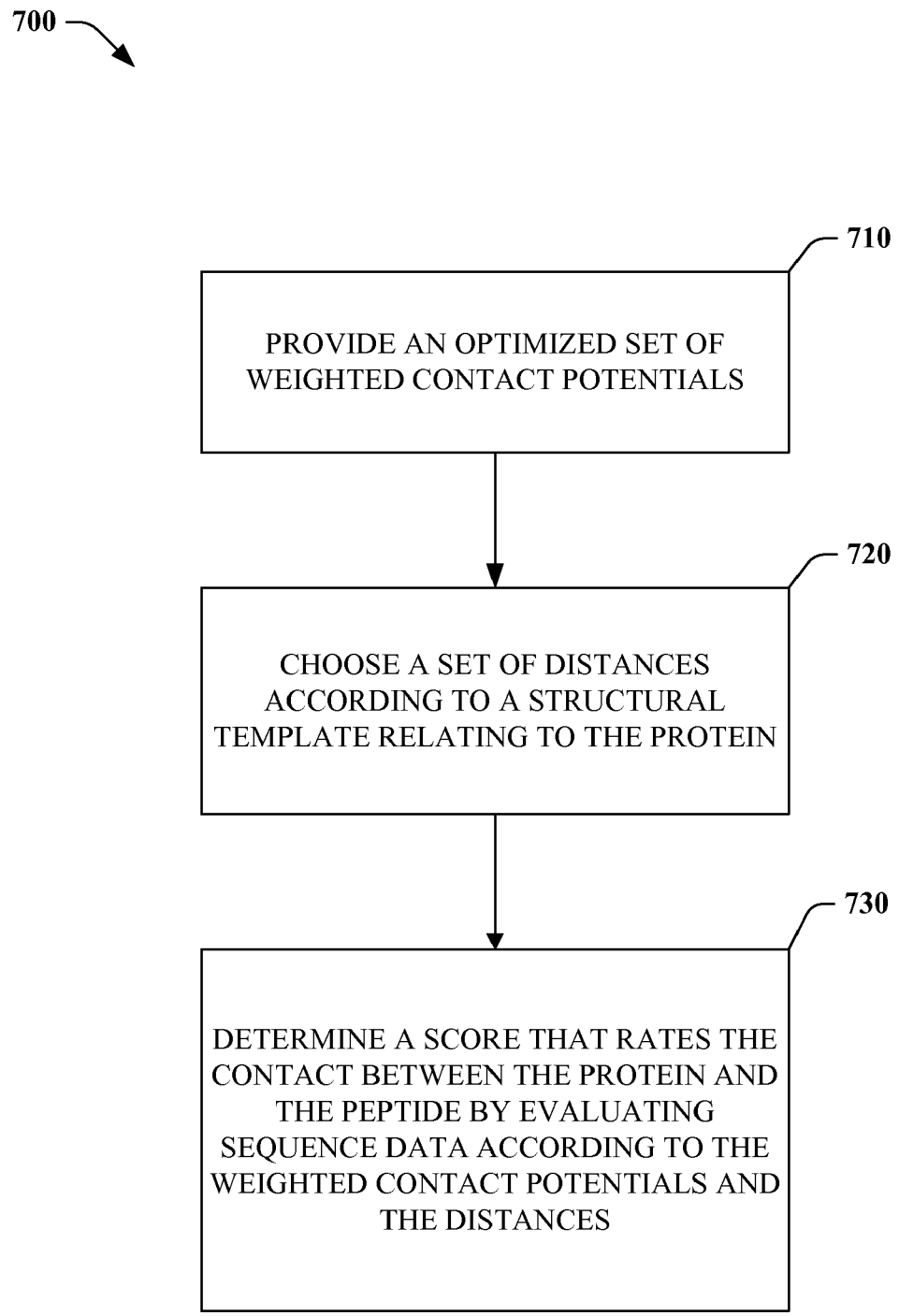
FIG. 7 is a flowchart illustrating one example of a method to evaluate a molecular contact.

FIG. 7 illustrates a method 700 for evaluating a contact between a protein (e.g., MHC, T cell receptor, antibody, etc.) and a peptide (e.g., epitope, 9mer, ligand, antigen, etc.). The term "ligand" is used broadly to mean any molecule that binds to another. A short molecule, such as a peptide, is one example of a ligand. The protein and peptide can be naturally occurring amino acid sequences or can be sequences not occurring naturally. At step 710, an optimized set of weighted contact potentials are provided. The set of optimized weighted contact potentials can be optimized utilizing one or more machine learning algorithms (e.g. iterative optimization, iterative least squares, generalized expectation maximization (GEM), variational expectation maximization (VEM), etc.). By way of example, the bilinear models with or without a soft step function given in equations 3-5 can be used to facilitate optimizing the weighted contact potentials.

At step 720, a set of distances are chosen according to a structural template relating to the protein. The structural template can be, for instance, obtained by crystallography and contain the 3-D coordinates of the amino acids of a protein-peptide complex (e.g., an MHC-peptide complex). The set of distances can define, for instance, the distance between an amino acid of the protein and an amino acid of the peptide for the two to be considered in contact. The set of distances can be chosen, for instance, by machine inferring (e.g., Bayesian inference) the identity of the structural template. One way to infer the structural template to define the distances is to employ a machine learning algorithm to choose the closest match from known structural templates. The match can be based on, for instance, the sequence of the protein or the sequences of both the protein and the peptide.

At step 730, a score that rates the contact (e.g., the binding energy) between the protein and the peptide is determined by evaluating protein sequence and peptide sequence data according to the set of distances and the optimized set of weighted contact potentials. One way of evaluating the sequence data according to the set of distances and optimized set of weighted contract potentials is by using the bilinear model described in reference to FIGS. 2-6 above. The protein sequence and peptide sequence data can be evaluated according to the set of distances by, for instance, utilizing an optimized soft step distance function (e.g. Equation 5). The optimized soft step distance function can be optimized, for instance, using gradient descent.

The steps of the method 700 need not be performed in the order described and can be performed in different orders. By way of example, step 720 can be performed before step 710 or steps 710 and 720 can be performed concurrently.

Figure 8:
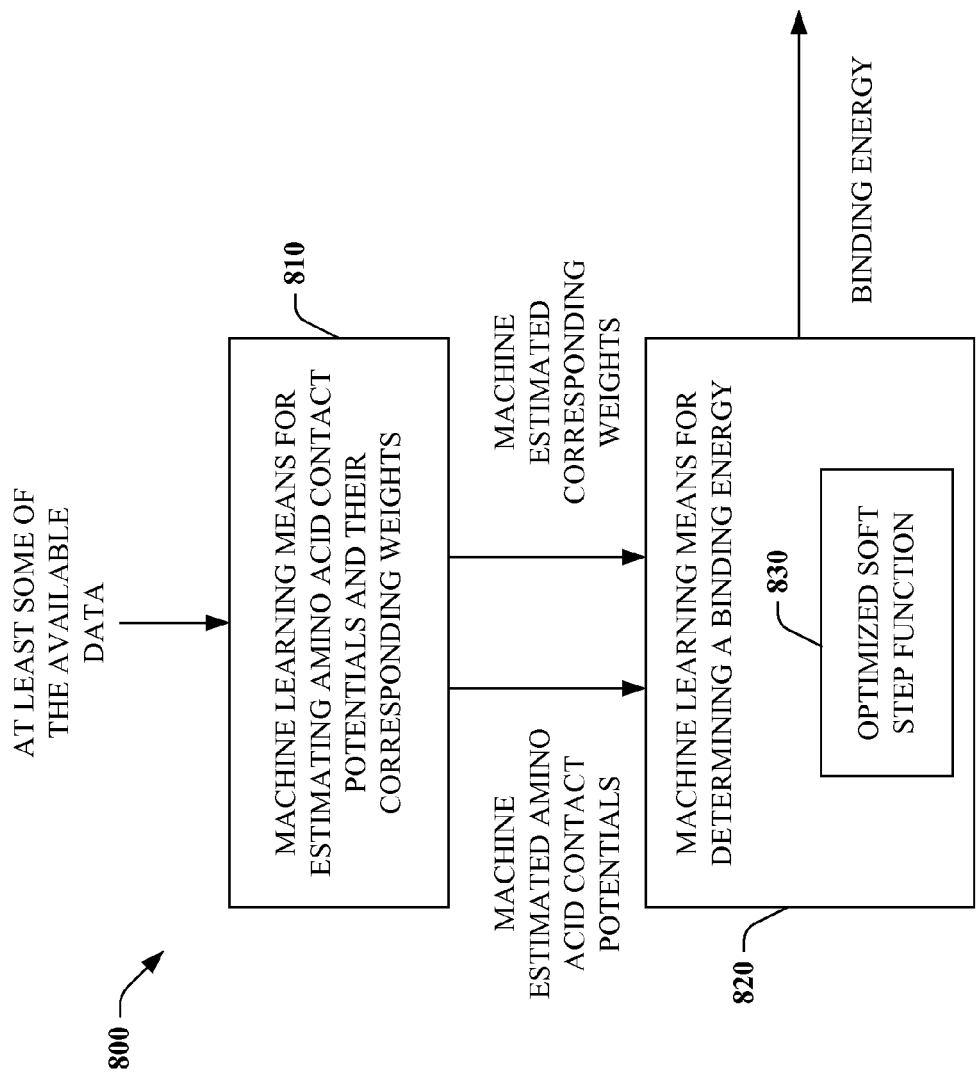
FIG. 8 is a block diagram of an exemplary system that facilitates determining the binding free energies of protein-protein complexes.
Figure 9A:
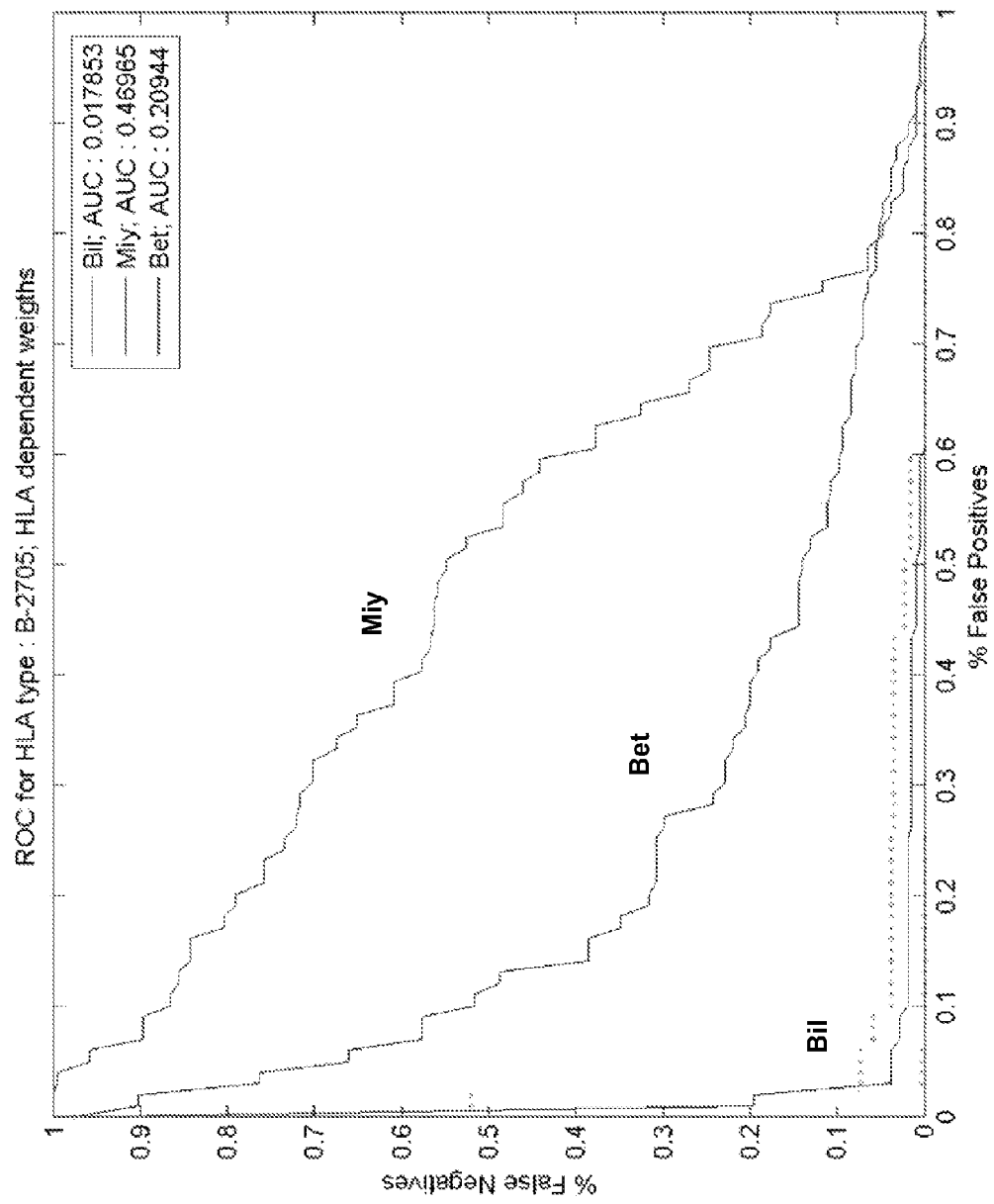
FIGS. 9a-d show ROC curves comparing the performance of a bilinear predictor having MHC-specific weights (Bil) to the standard threading approach employing two previously published pairwise potential matrices (Miy and Bet).
Figure 9B:
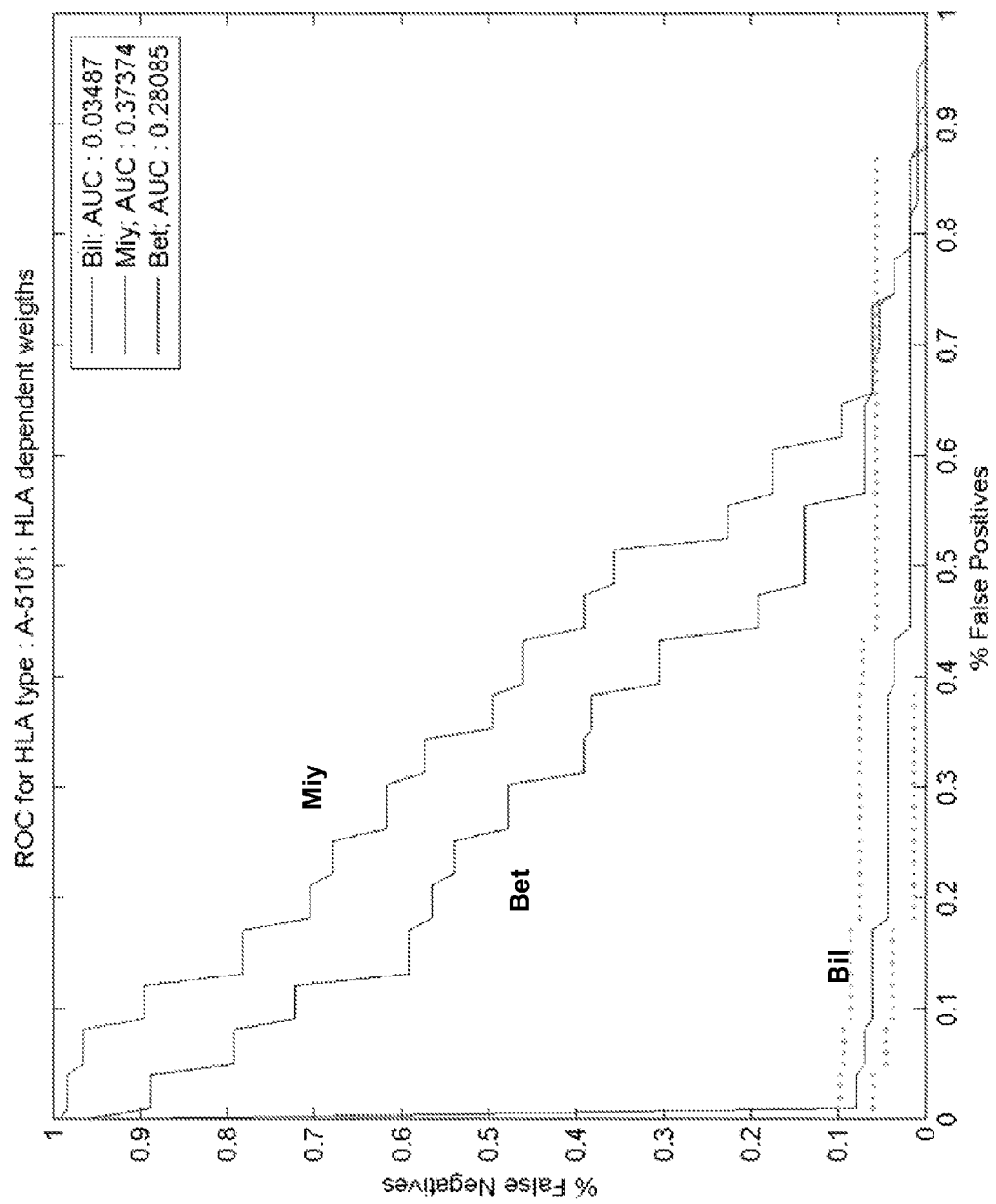
Figure 9C:
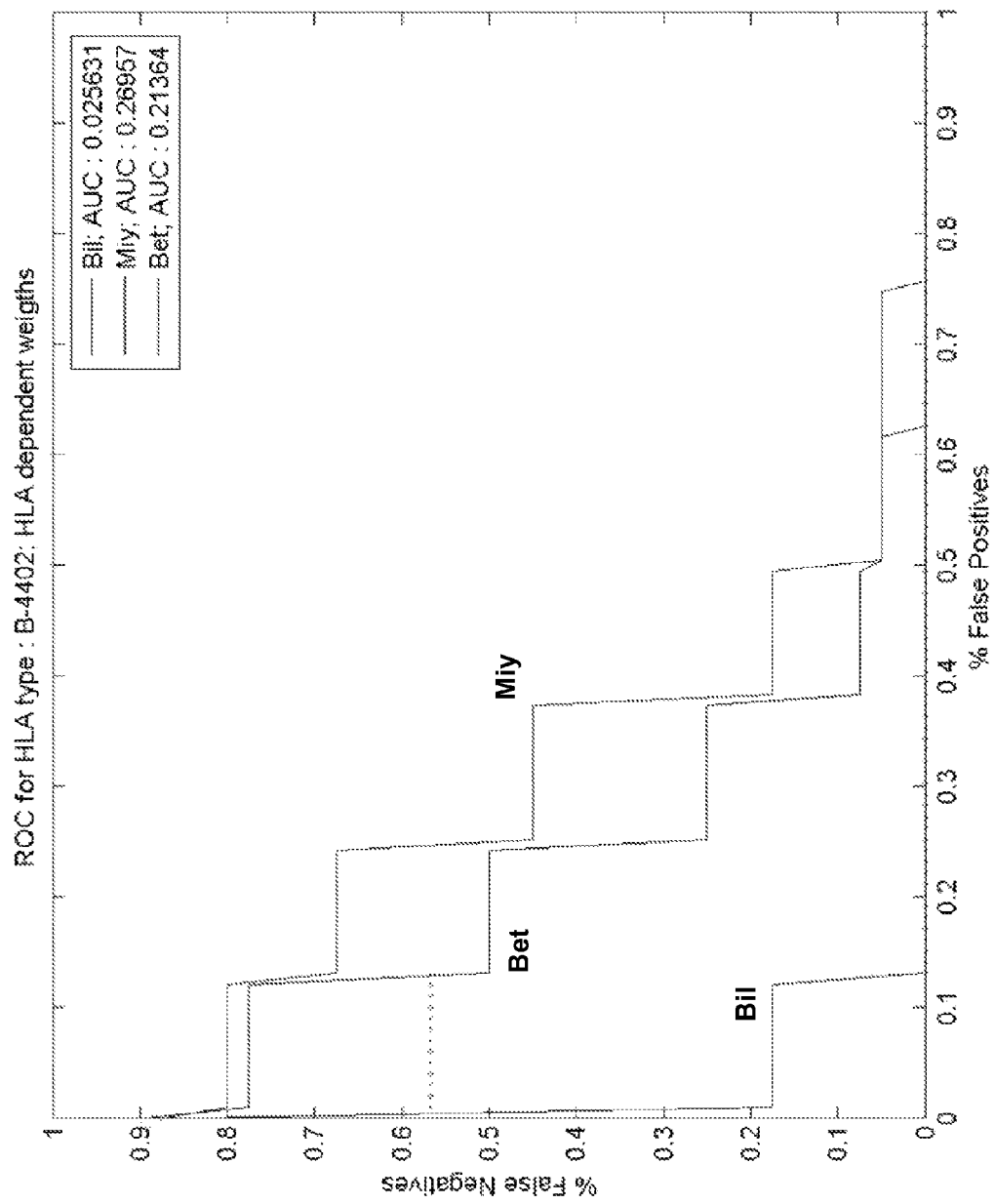
Figure 9D:
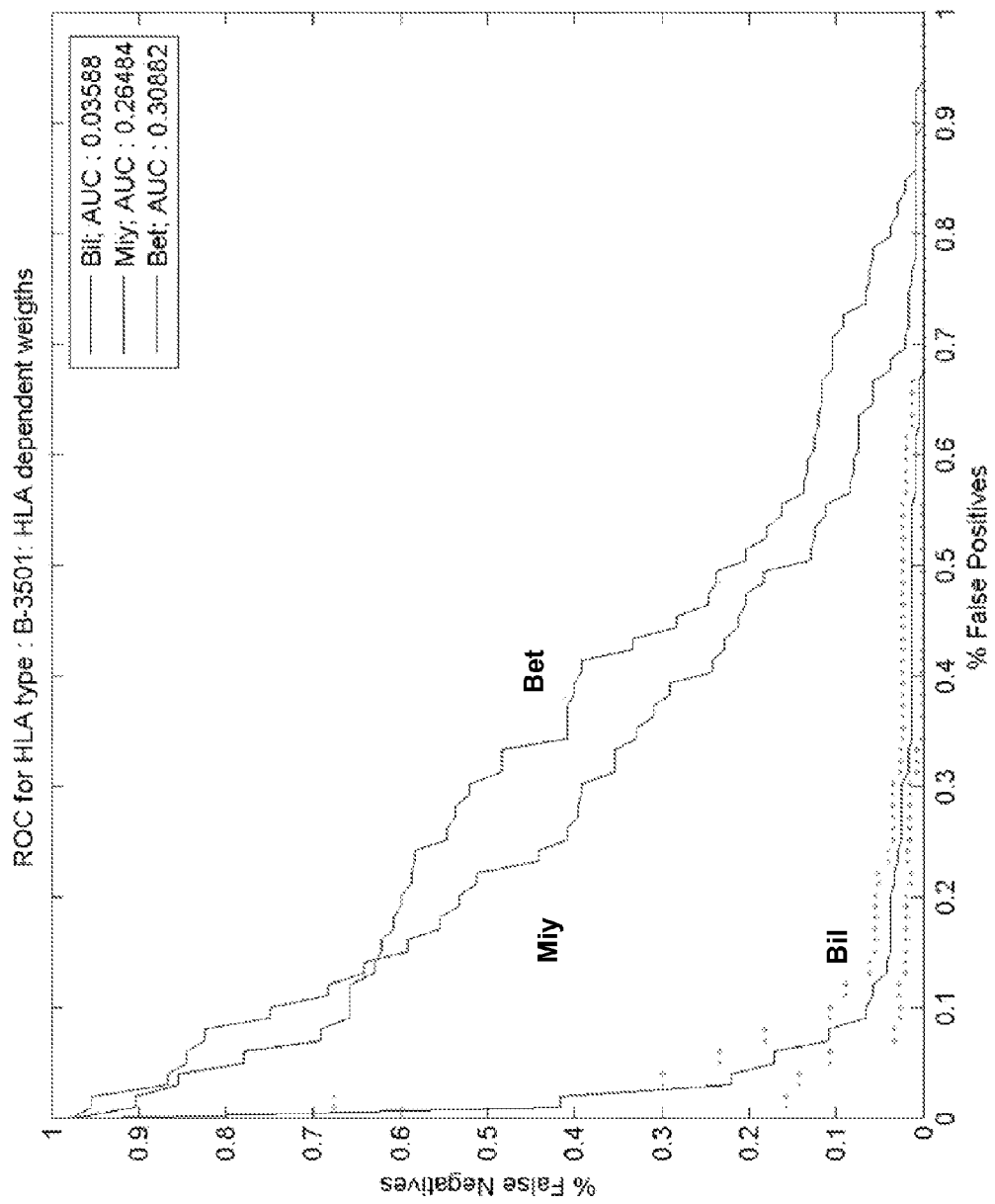
Figure 10A:
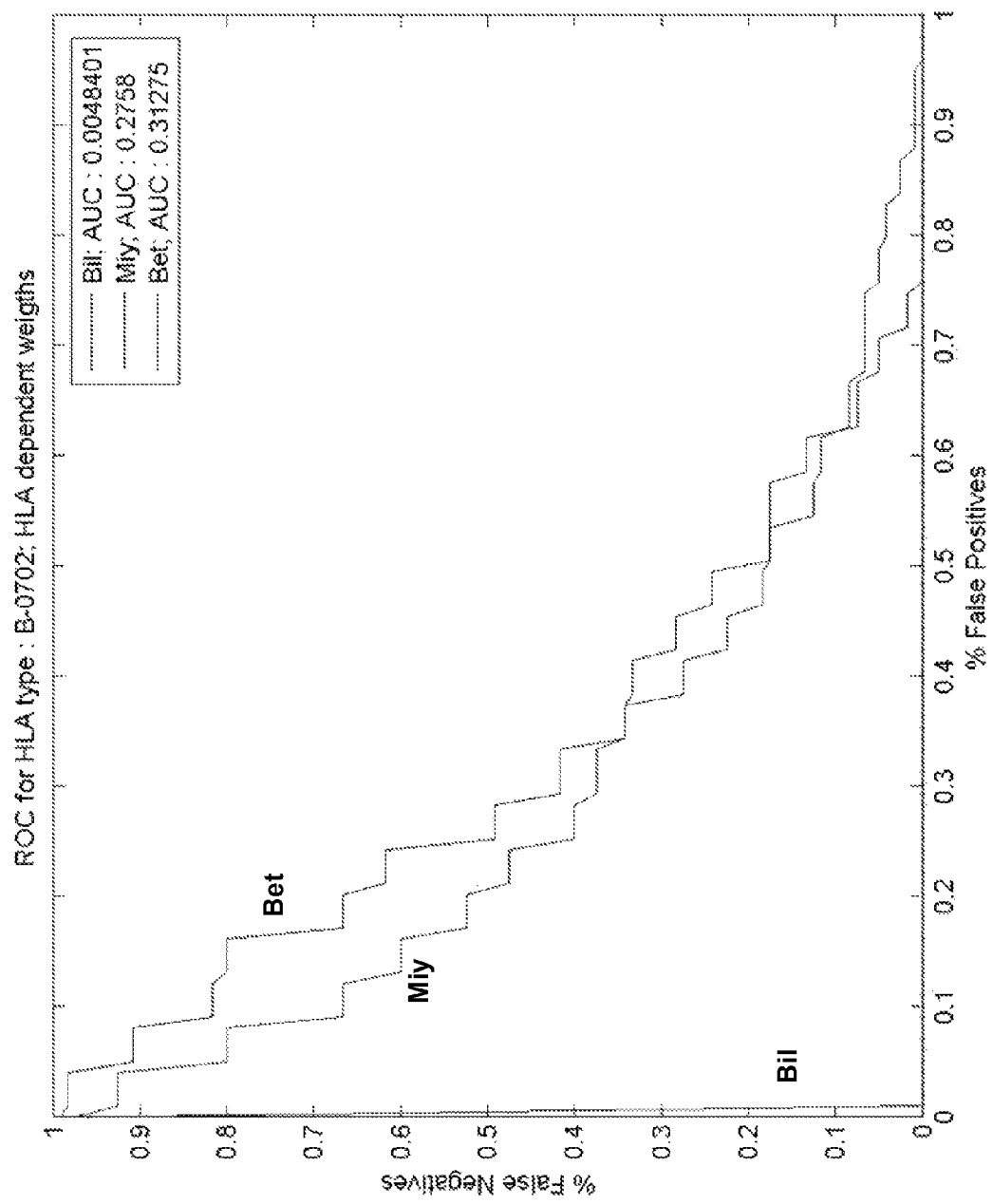
FIGS. 10a-e show ROC curves comparing the performance of a bilinear predictor having MHC-specific weights (Bil) to the standard threading approach employing two previously published pairwise potential matrices (Miy and Bet).
Figure 10B:
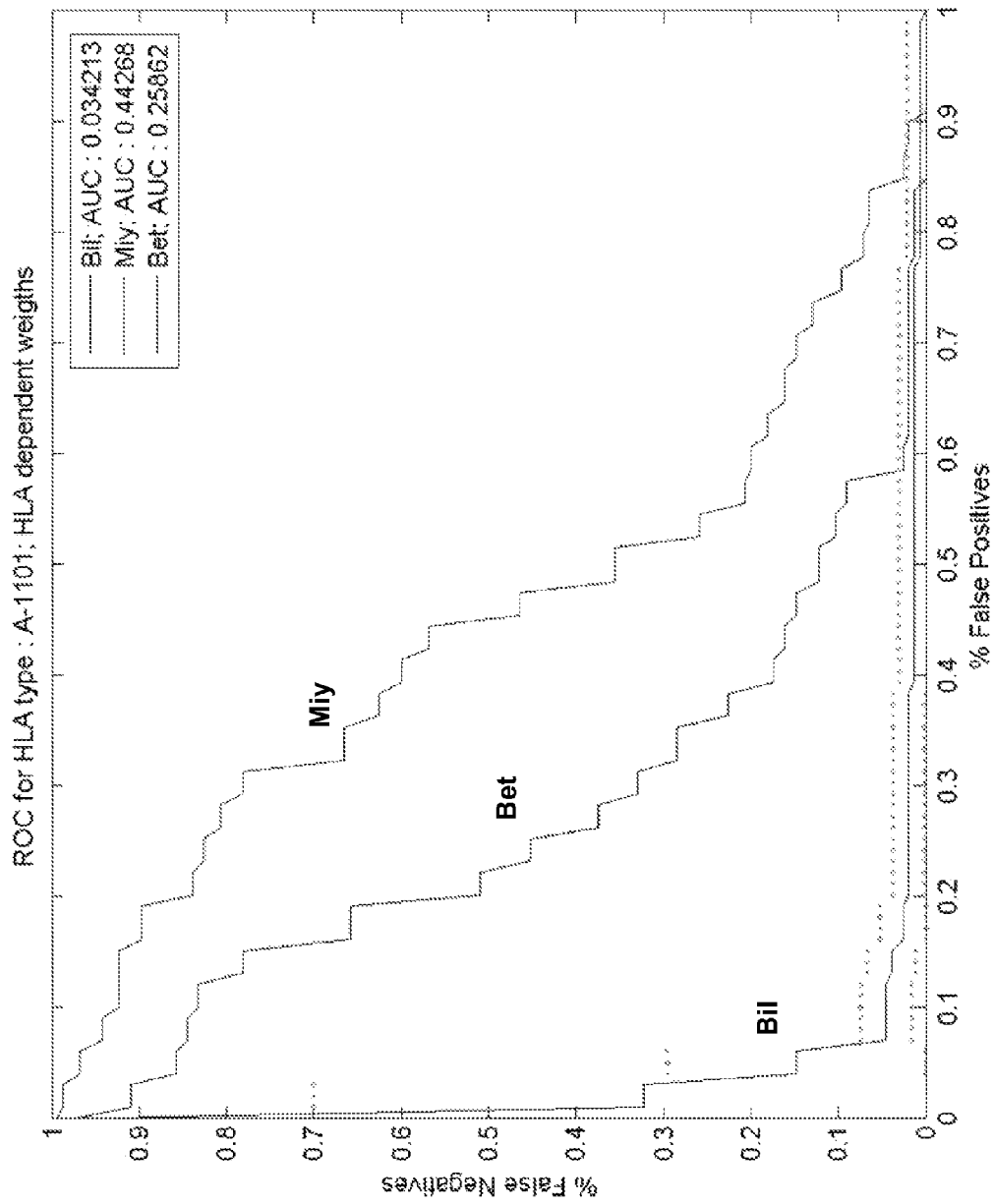
Figure 10C:
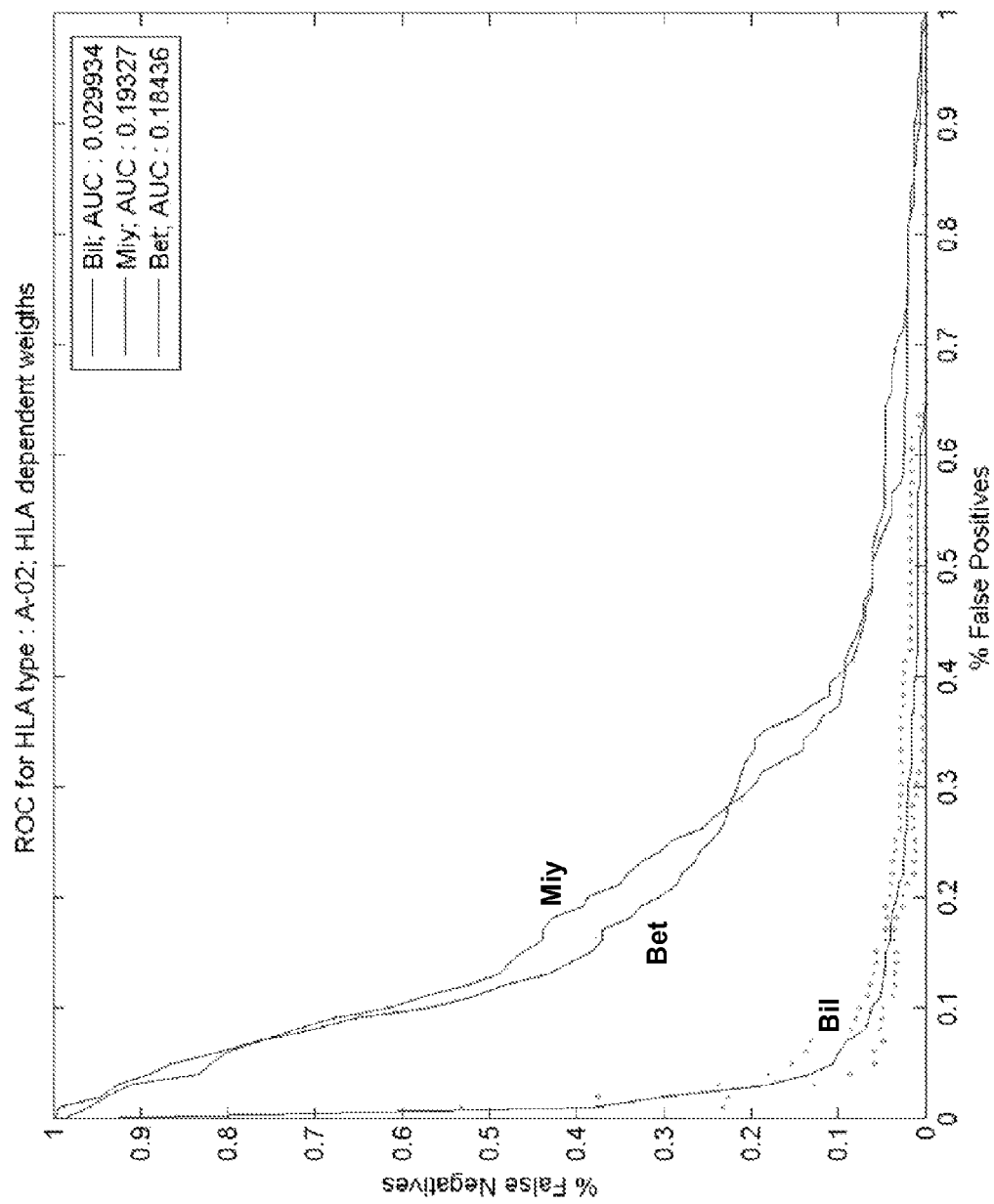
Figure 10D:
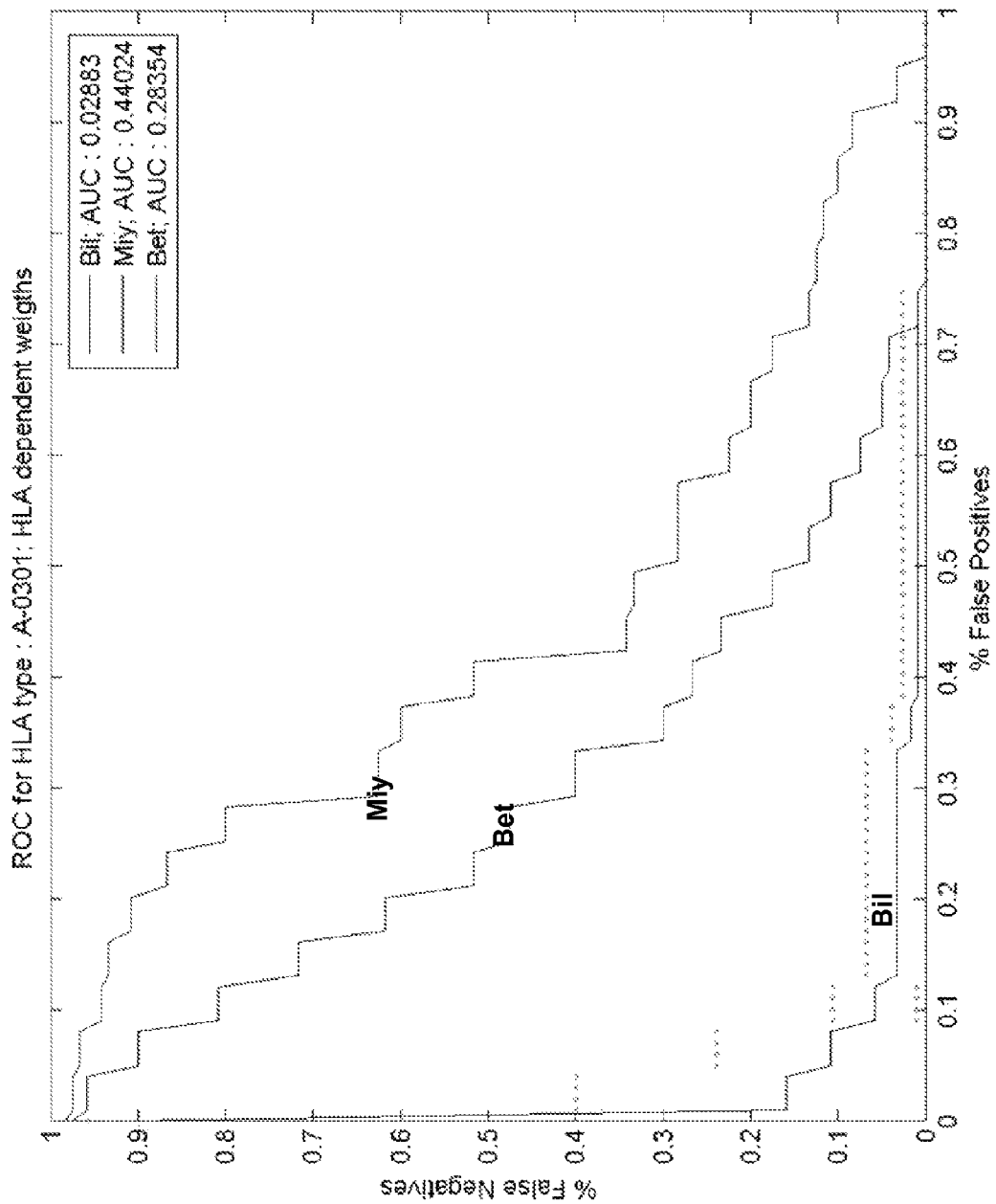
Figure 10E:
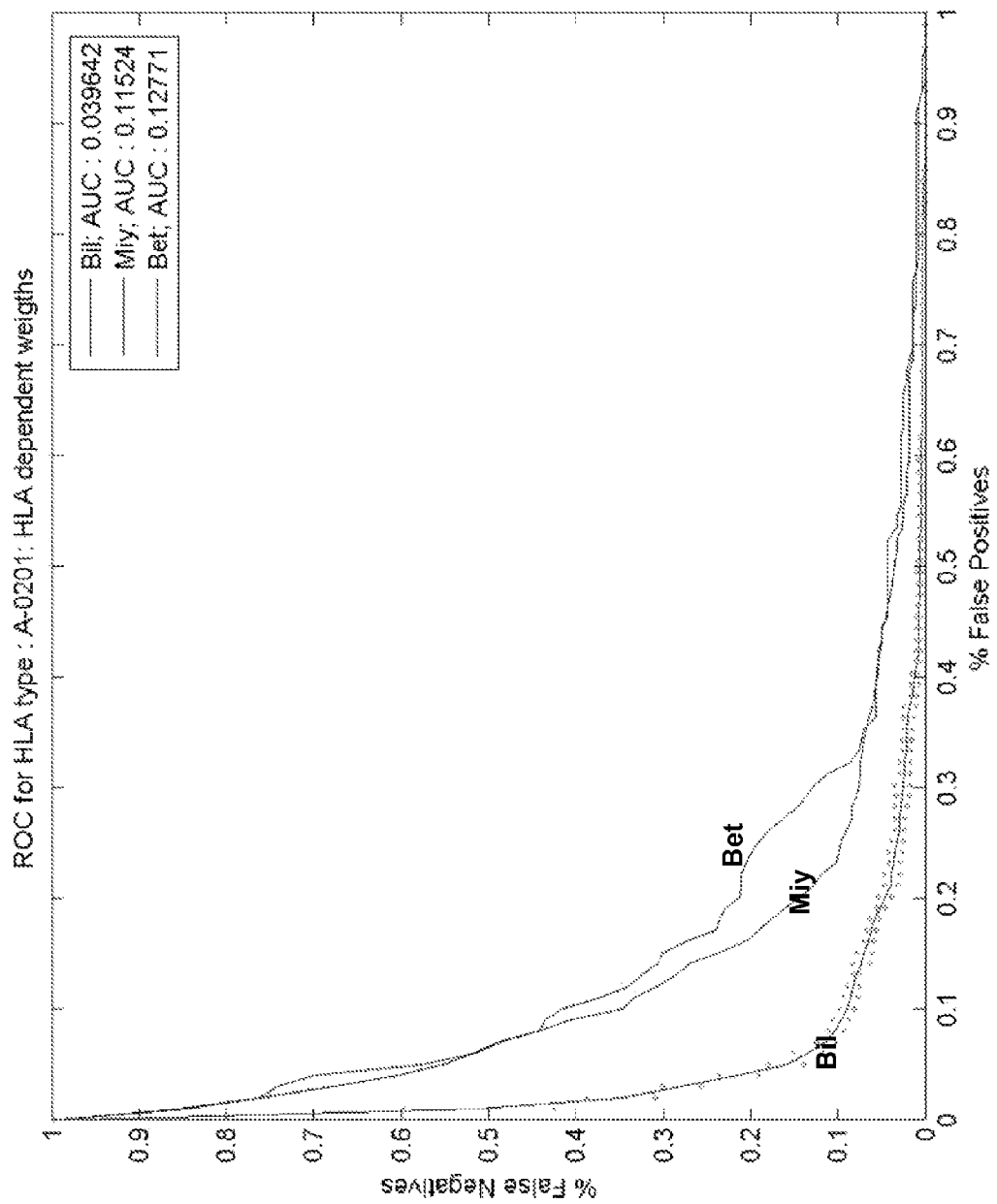
Figure 11A:
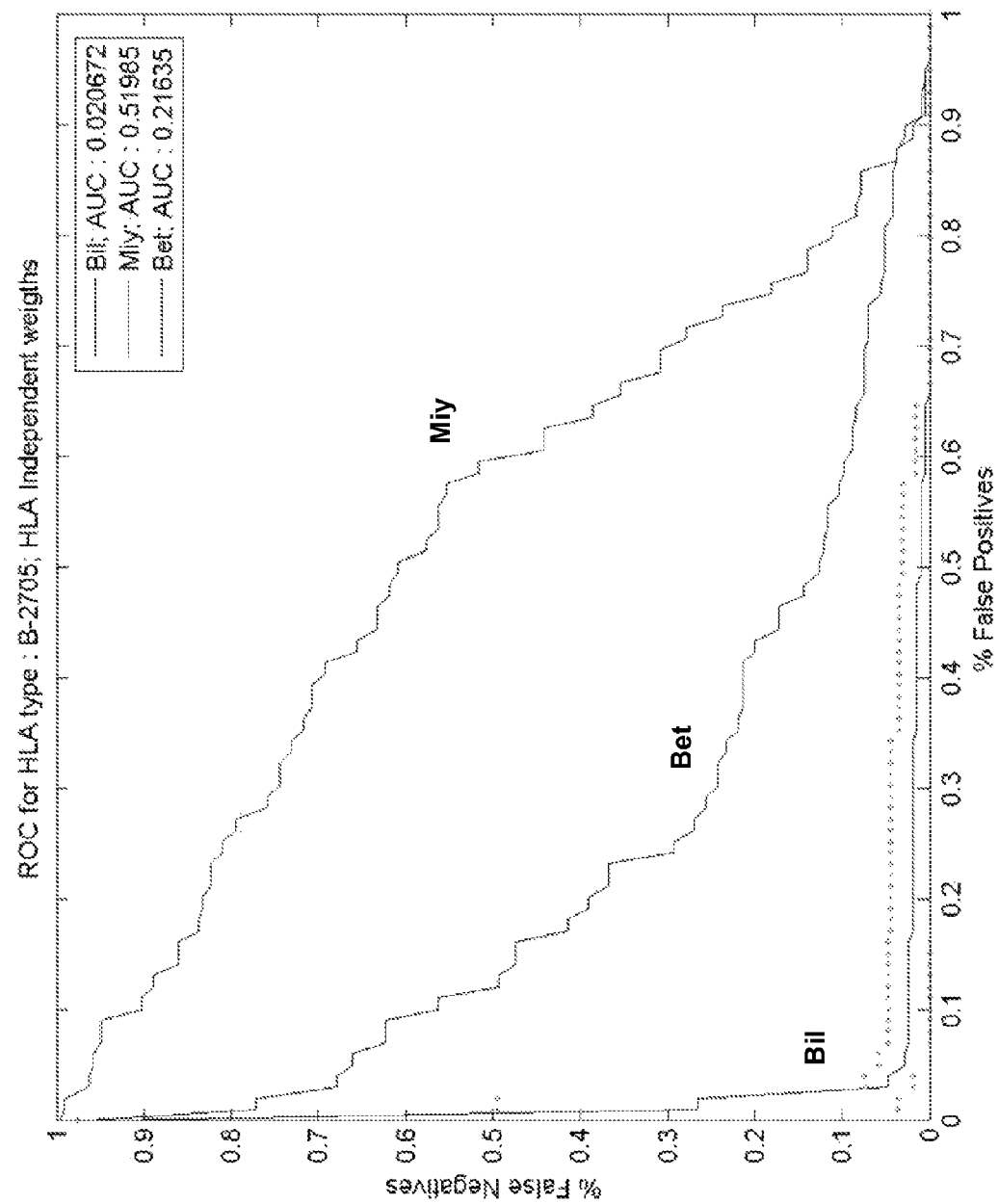
FIGS. 11a-d show ROC curves comparing the performance of a bilinear predictor having MHC-independent weights (Bil) to the standard threading approach employing two previously published pairwise potential matrices (Miy and Bet).
Figure 11B:
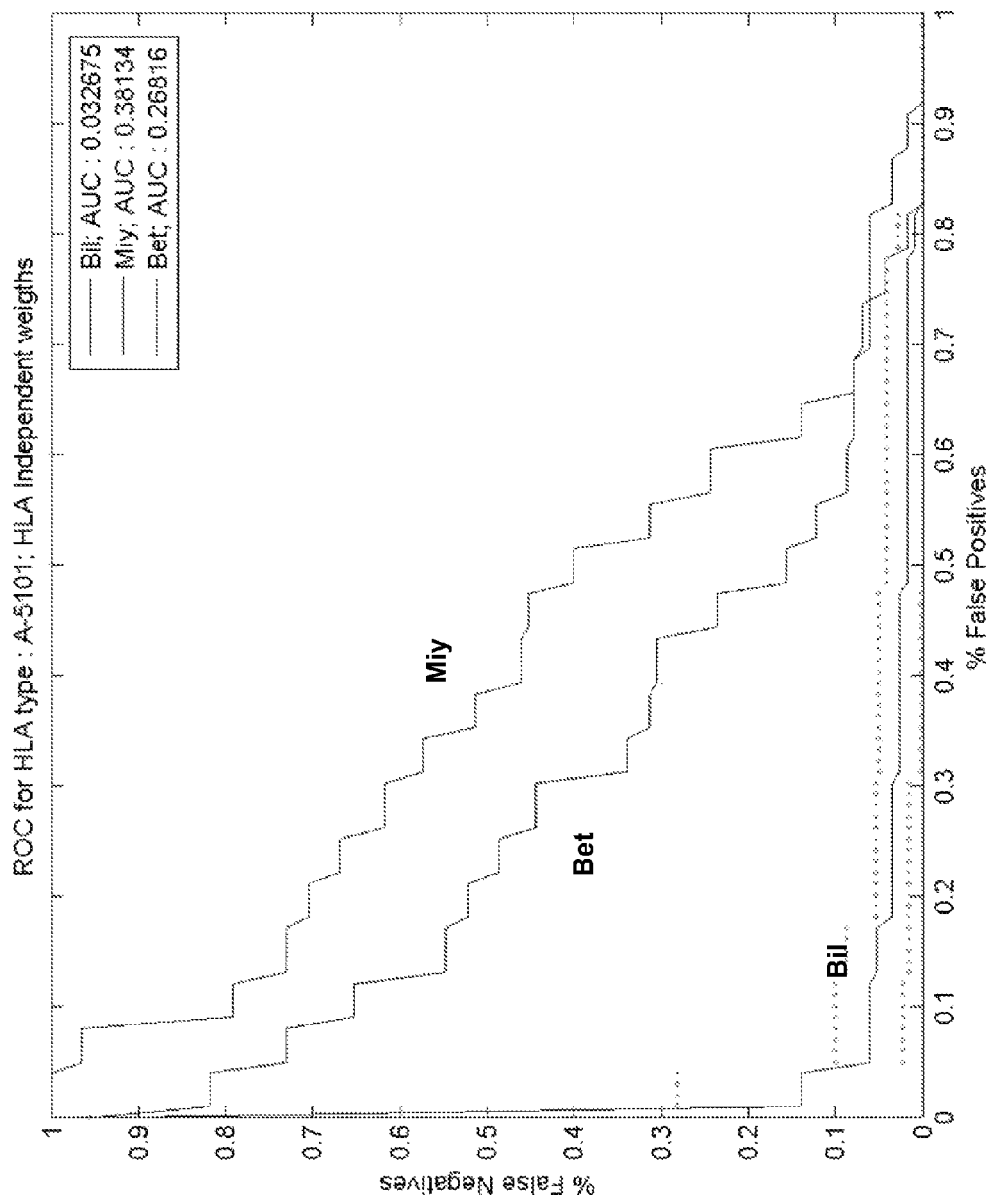
Figure 11C:
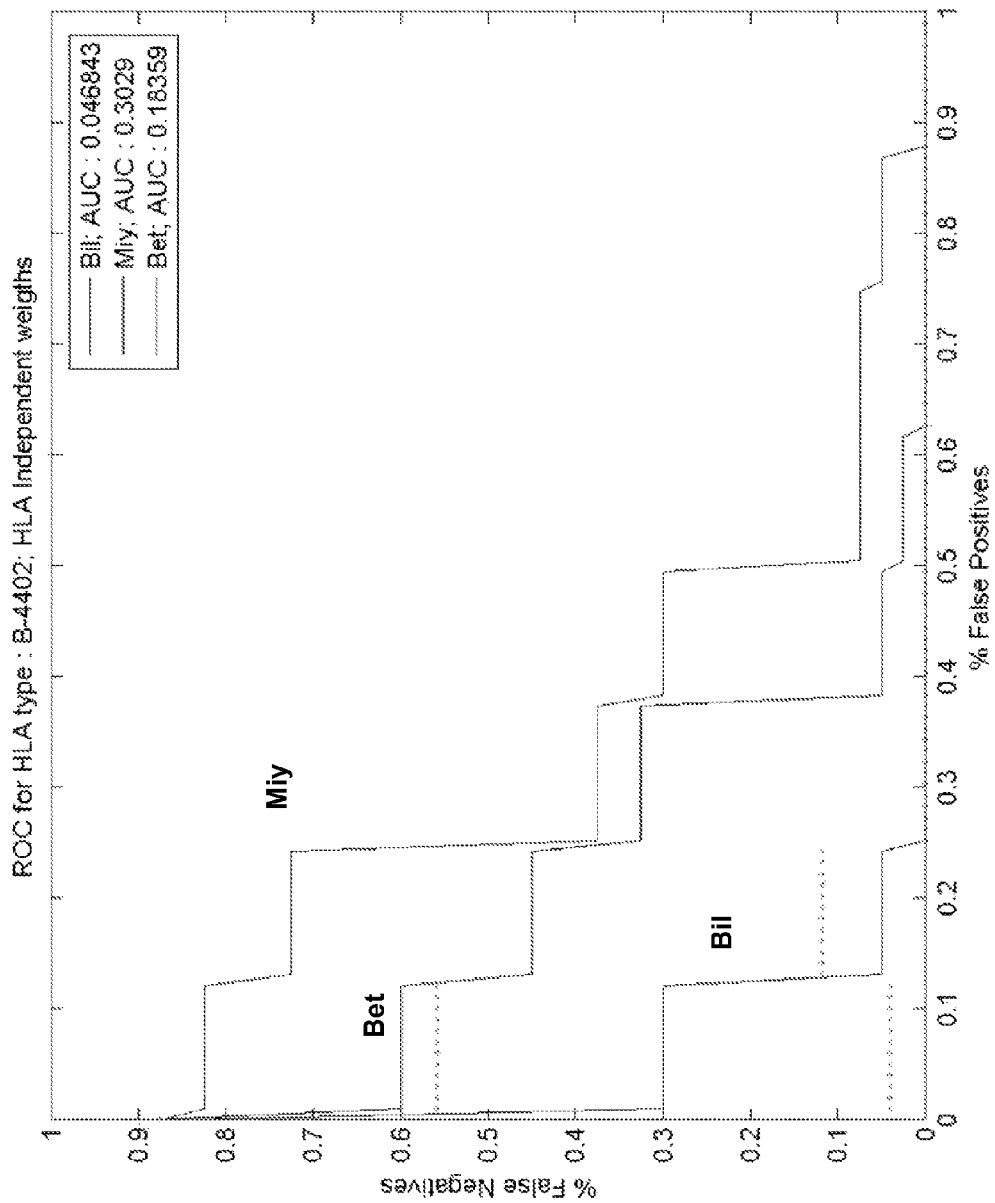
Figure 11D:
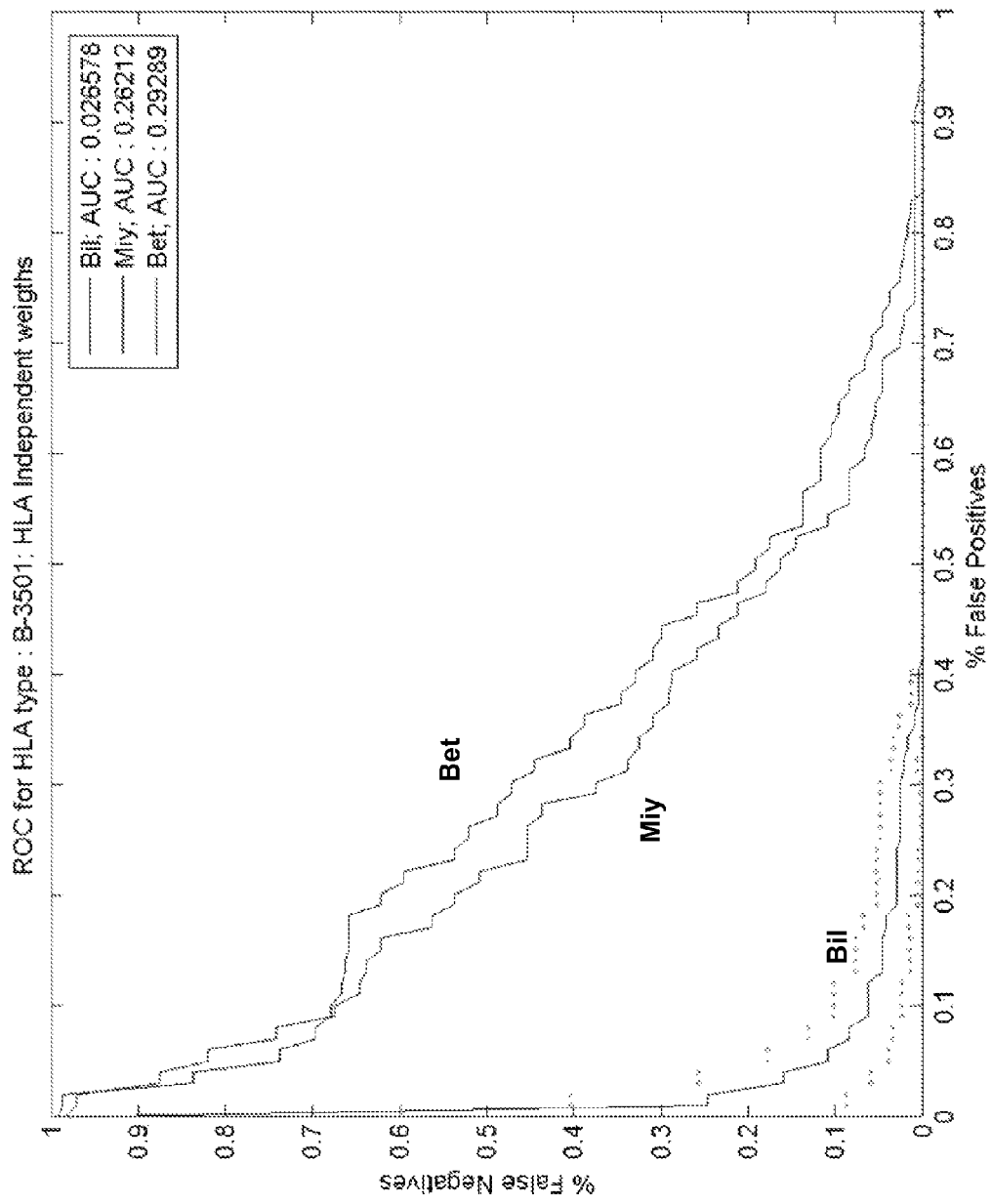
Figure 12A:
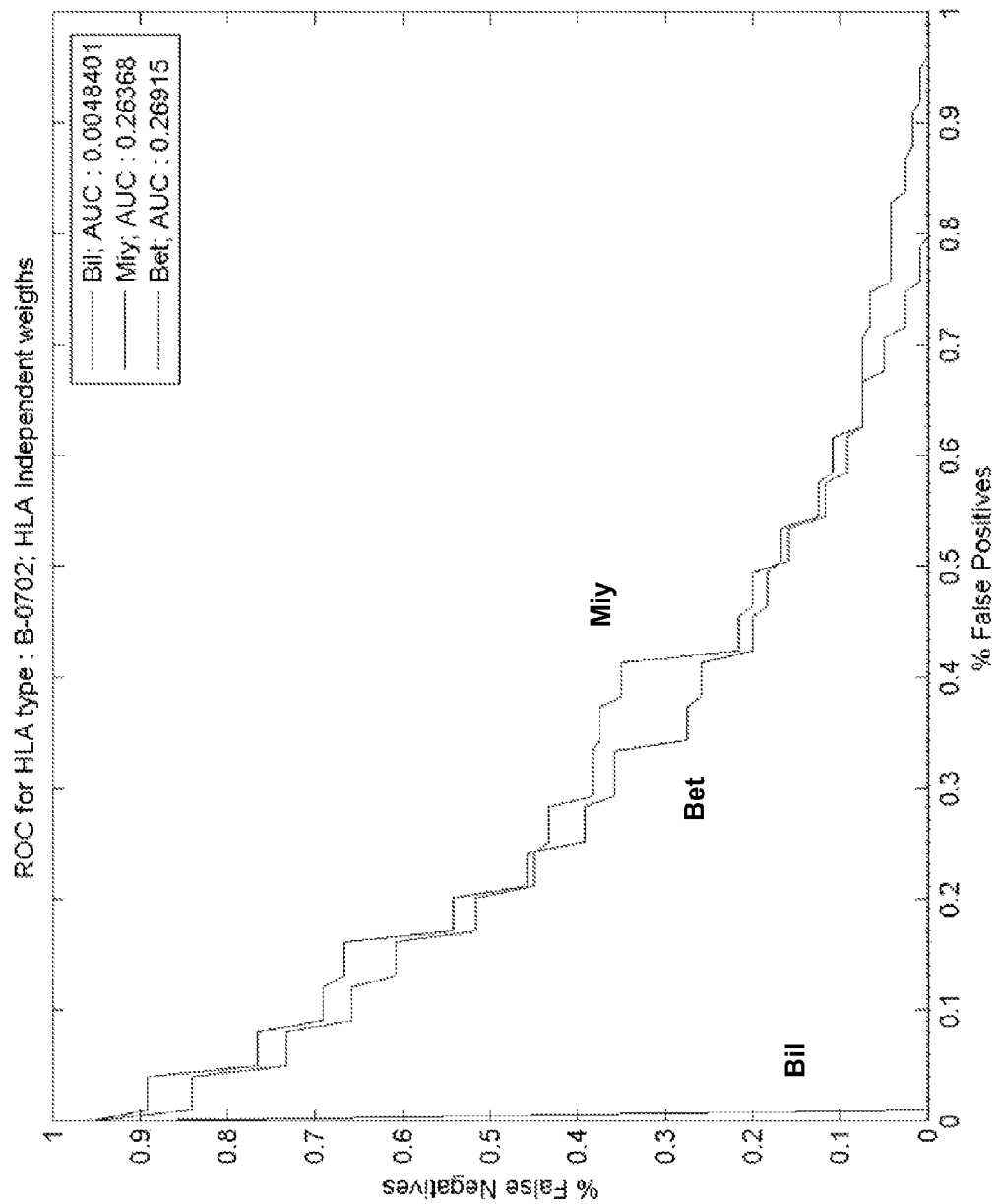
FIGS. 12a-e show ROC curves comparing the performance of a bilinear predictor having MHC-independent weights (Bil) to the standard threading approach employing two previously published pairwise potential matrices (Miy and Bet).
Figure 12B:
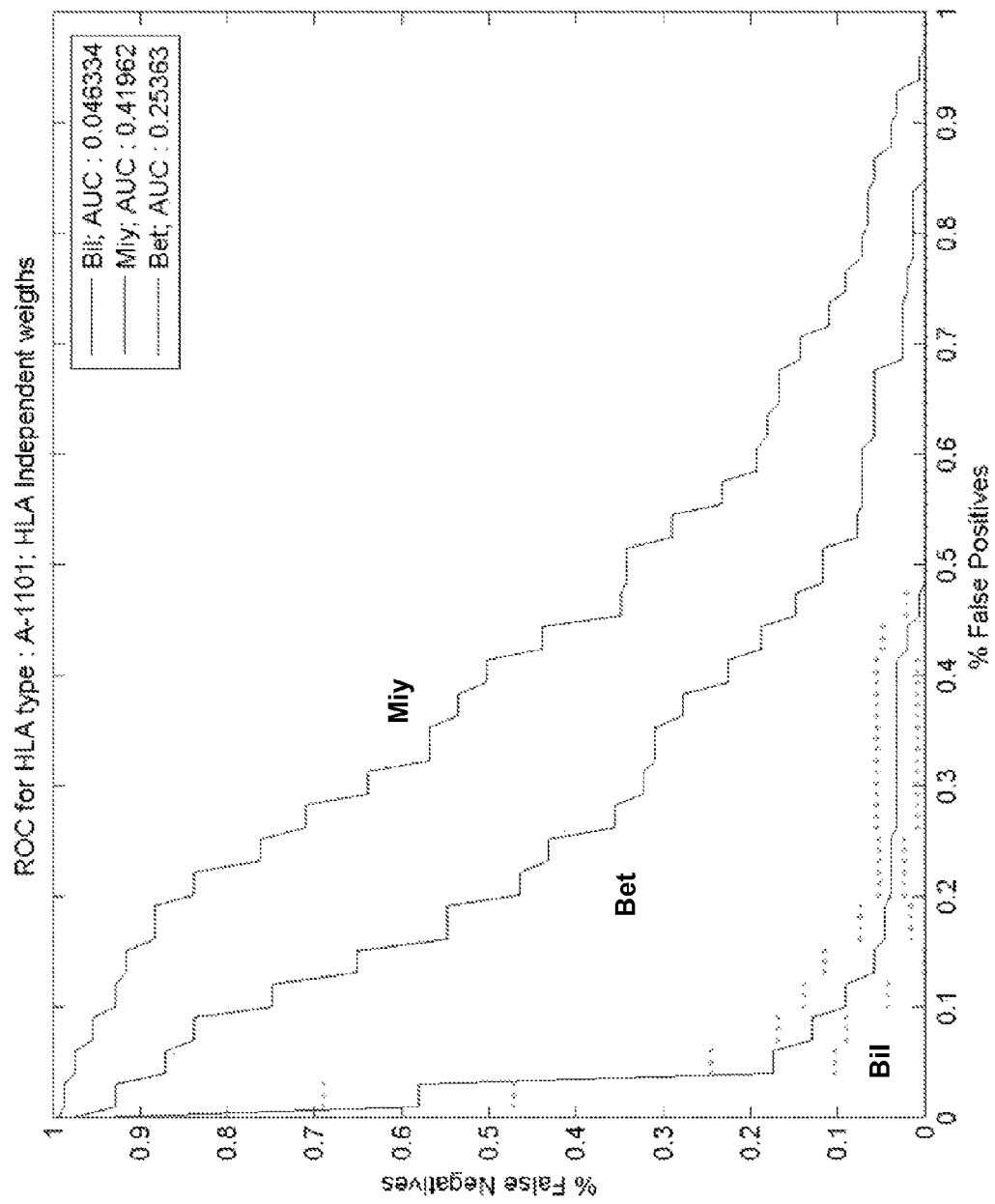
Figure 12C:
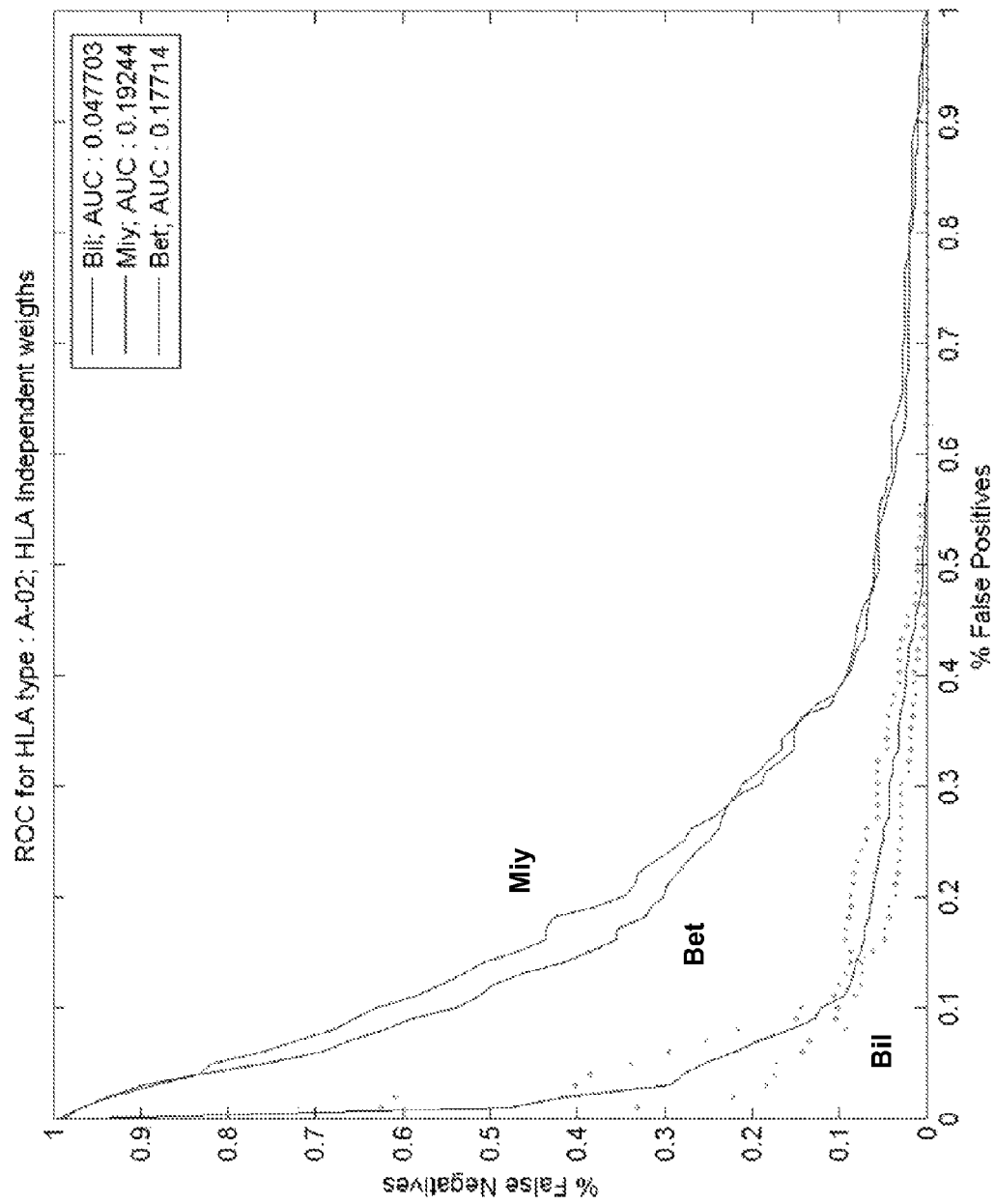
Figure 12D:
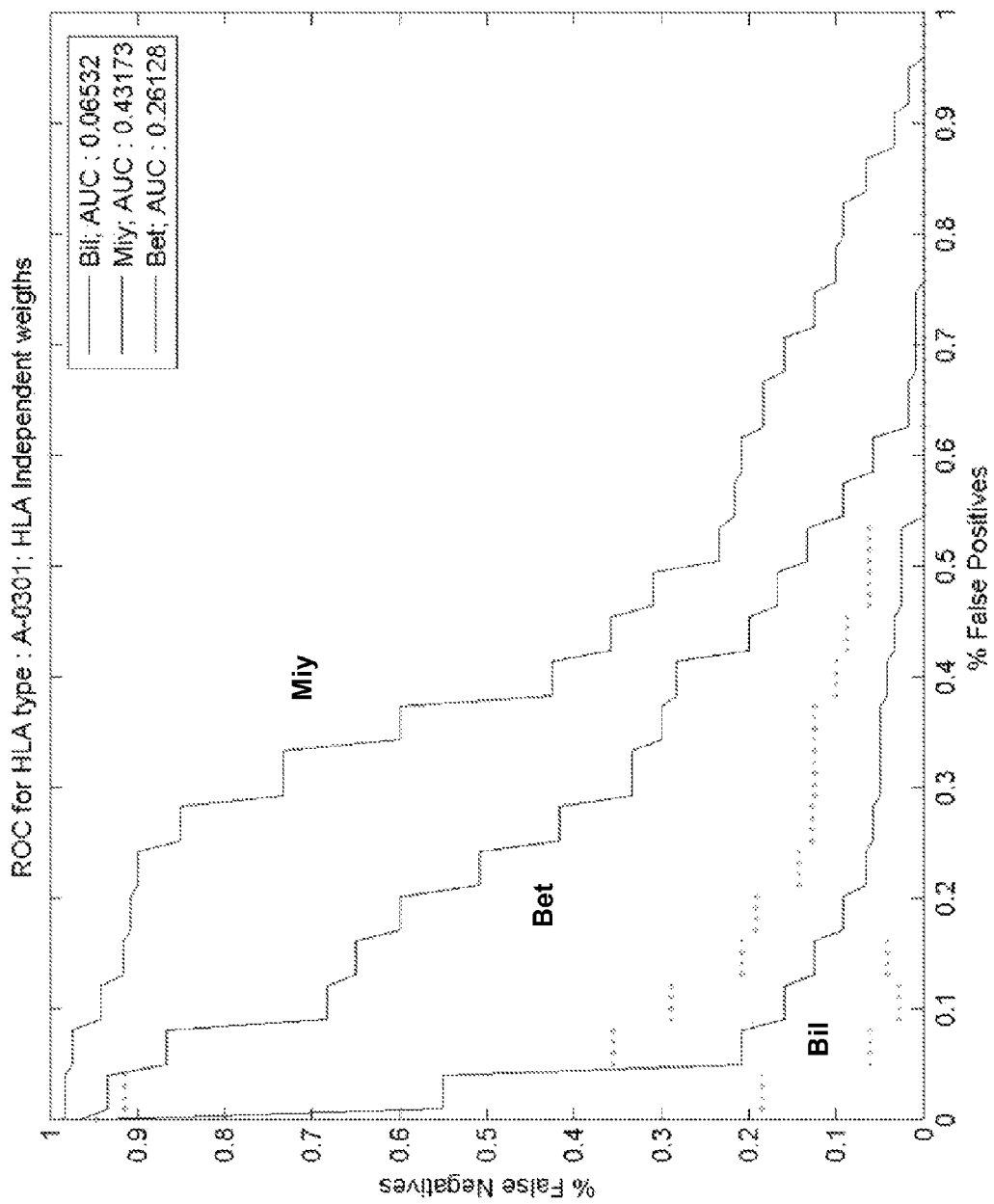
Figure 12E:
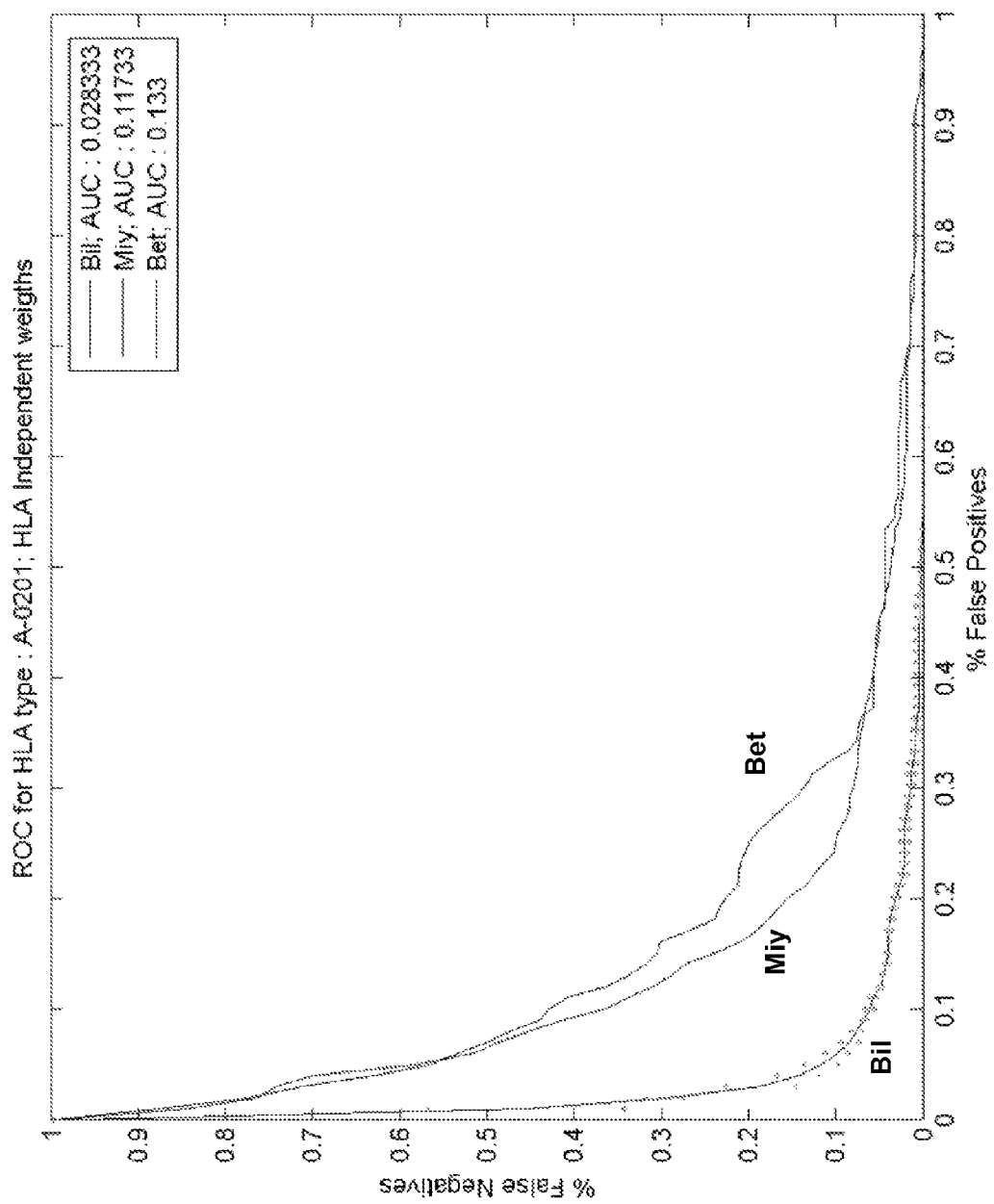
Figure 13A:
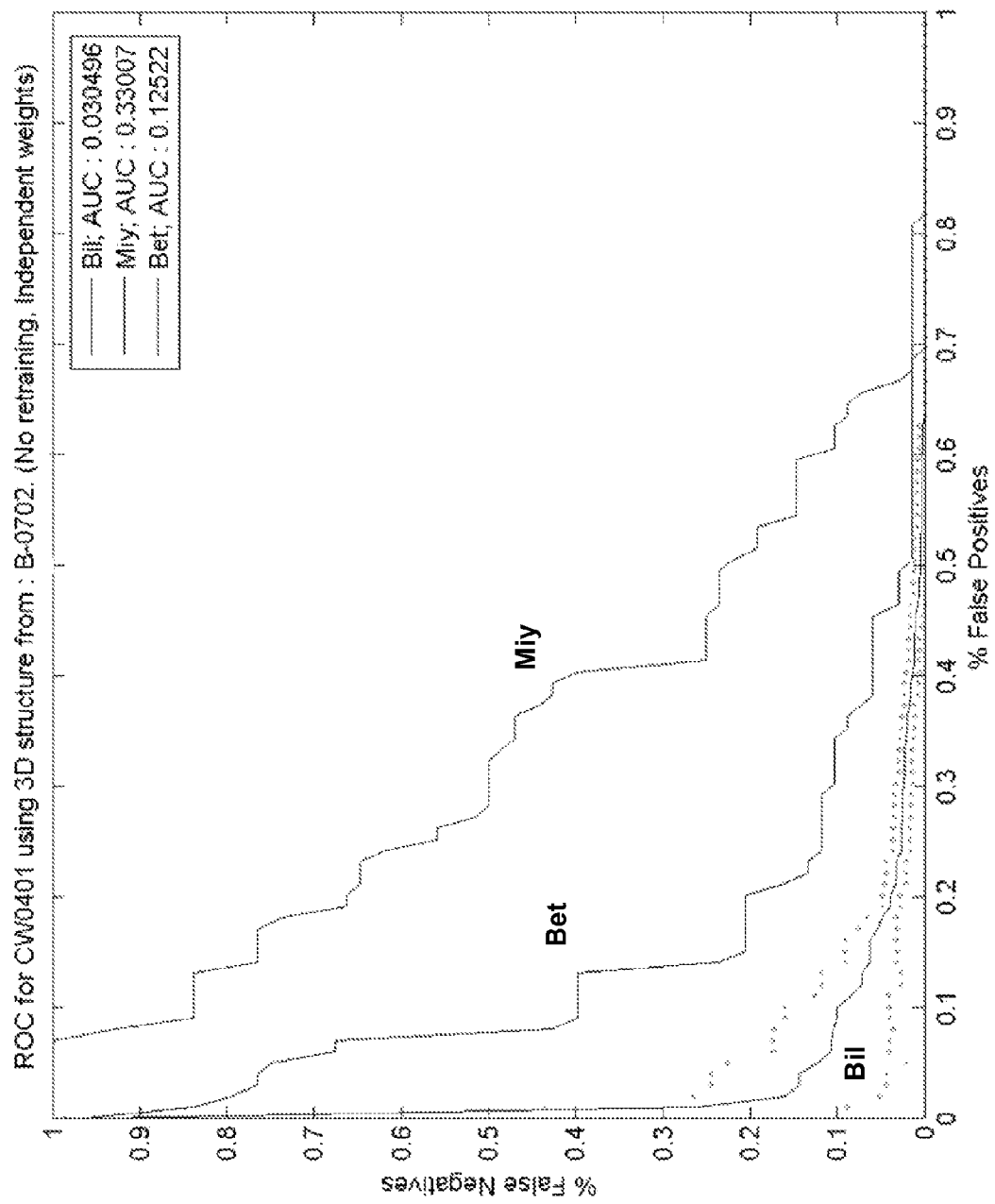
FIGS. 13a-d show ROC curves comparing the performance of a bilinear predictor having MHC-specific weights (Bil) trained on data from different MHC molecules to the standard threading approach employing two previously published pairwise potential matrices (Miy and Bet).
Figure 13B:
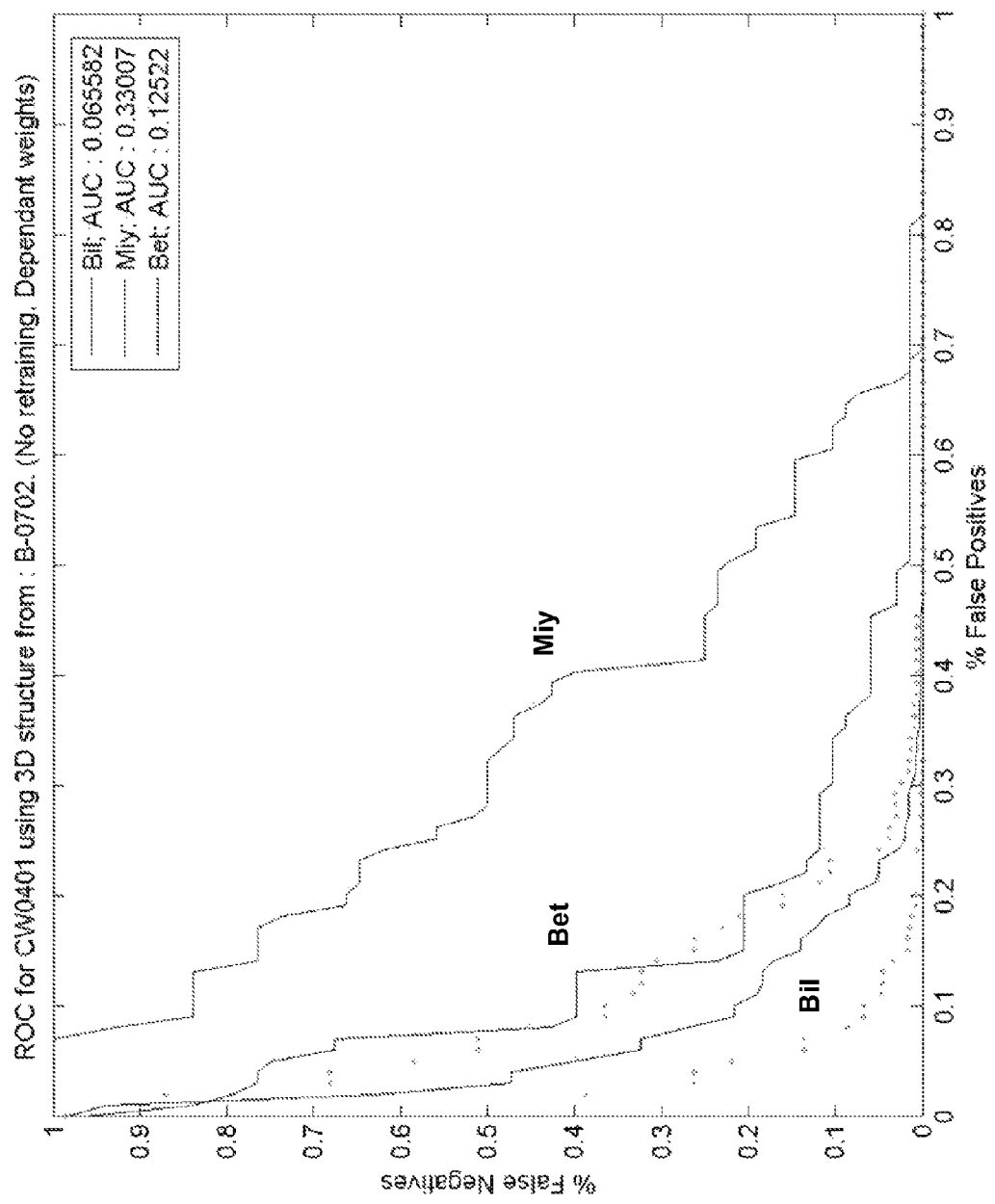
Figure 13C:
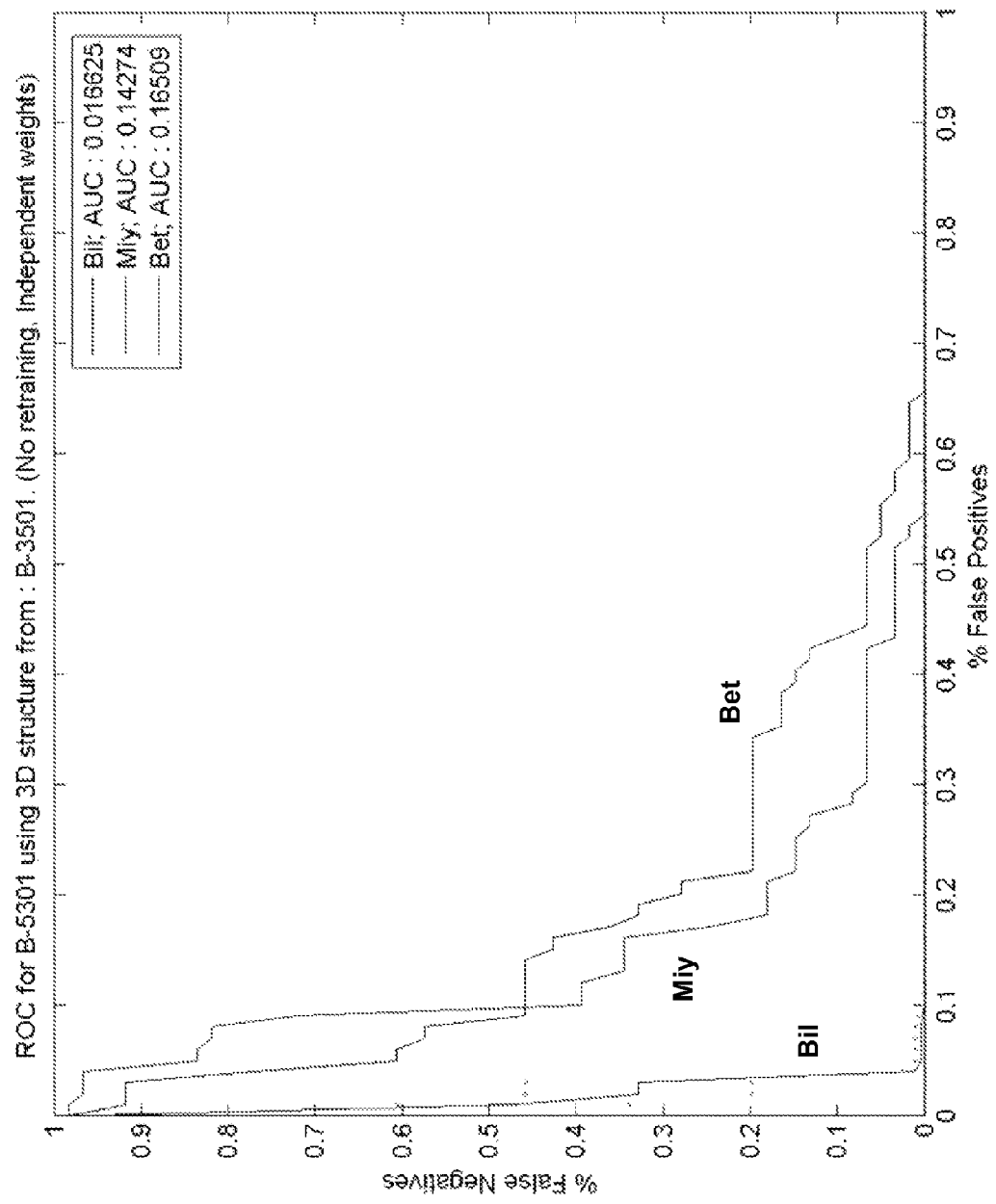
Figure 13D:
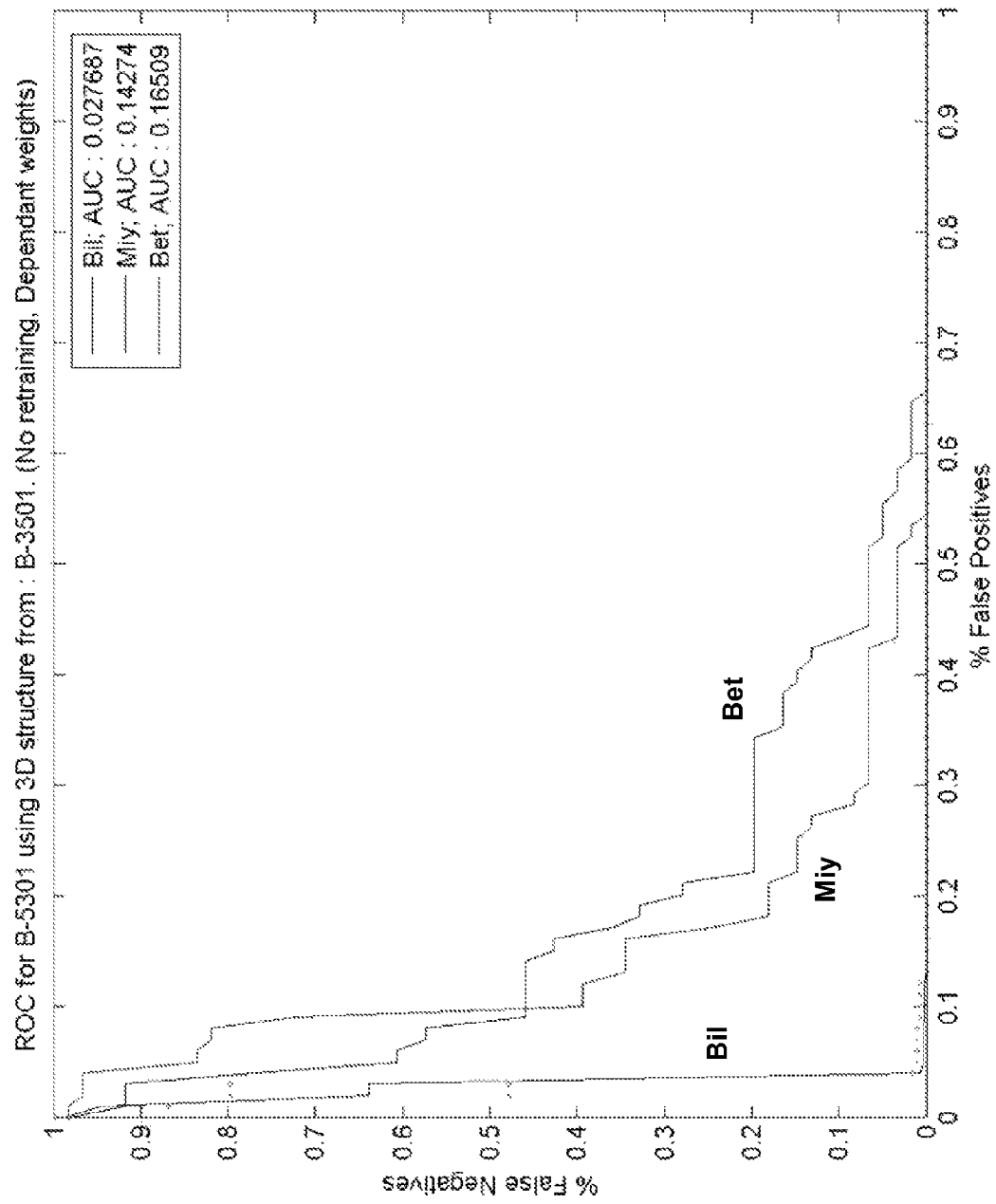
Figure 14A:
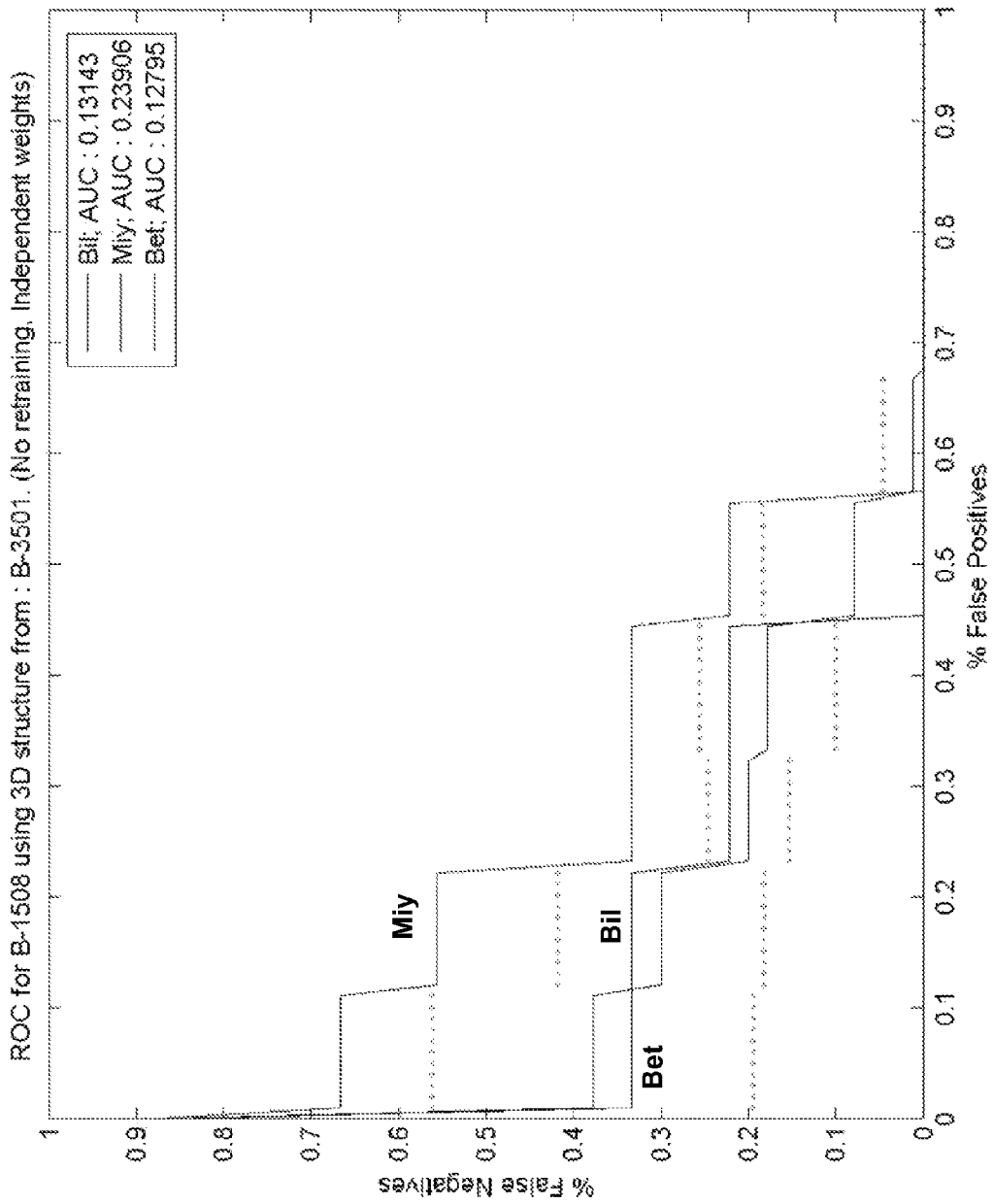
FIGS. 14a-d show ROC curves comparing the performance of a bilinear predictor having MHC-independent weights (Bil) trained on data from different MHC molecules to the standard threading approach employing two previously published pairwise potential matrices (Miy and Bet).
Figure 14B:
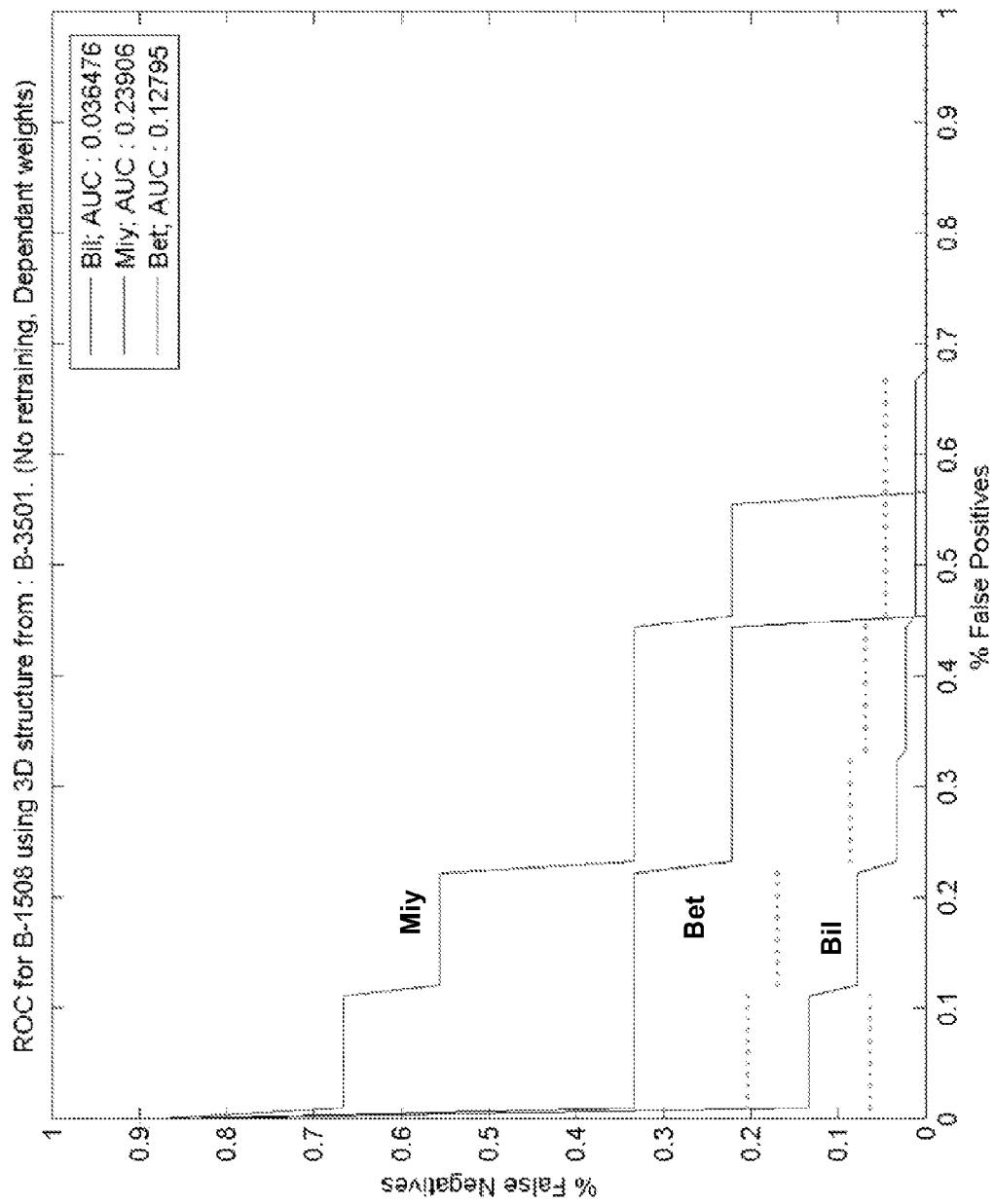
Figure 14C:
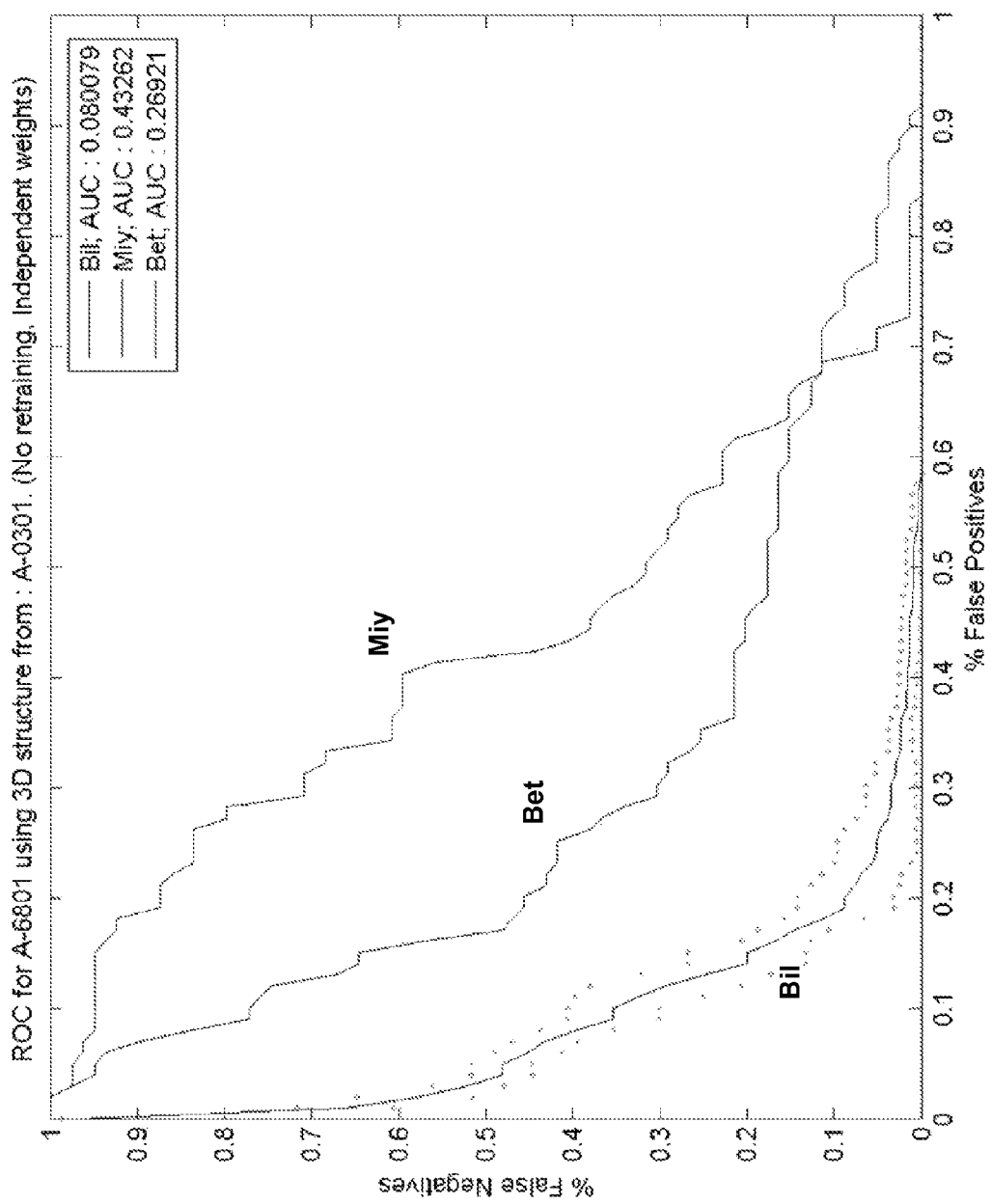
Figure 14D:
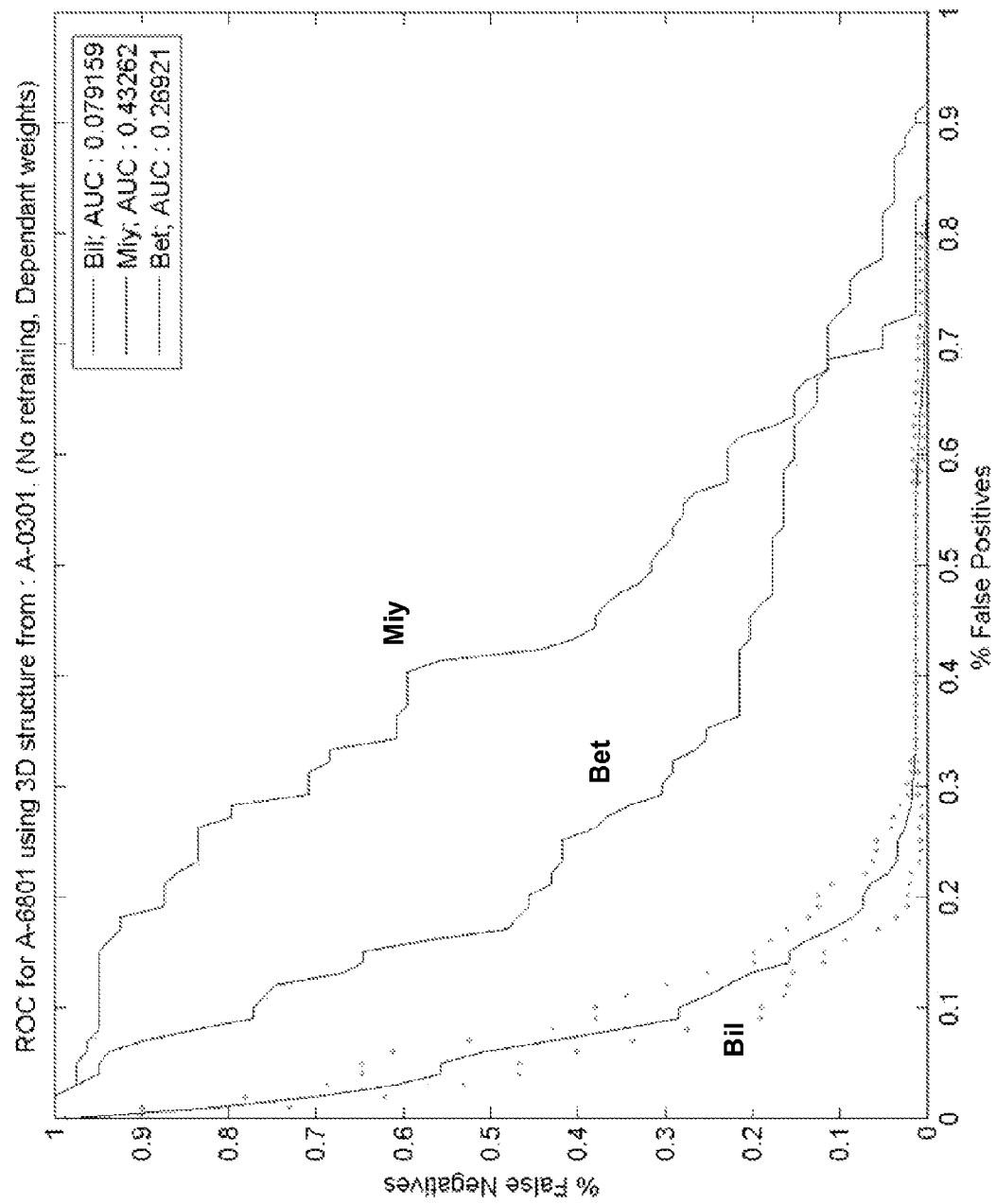
Figure 15A:
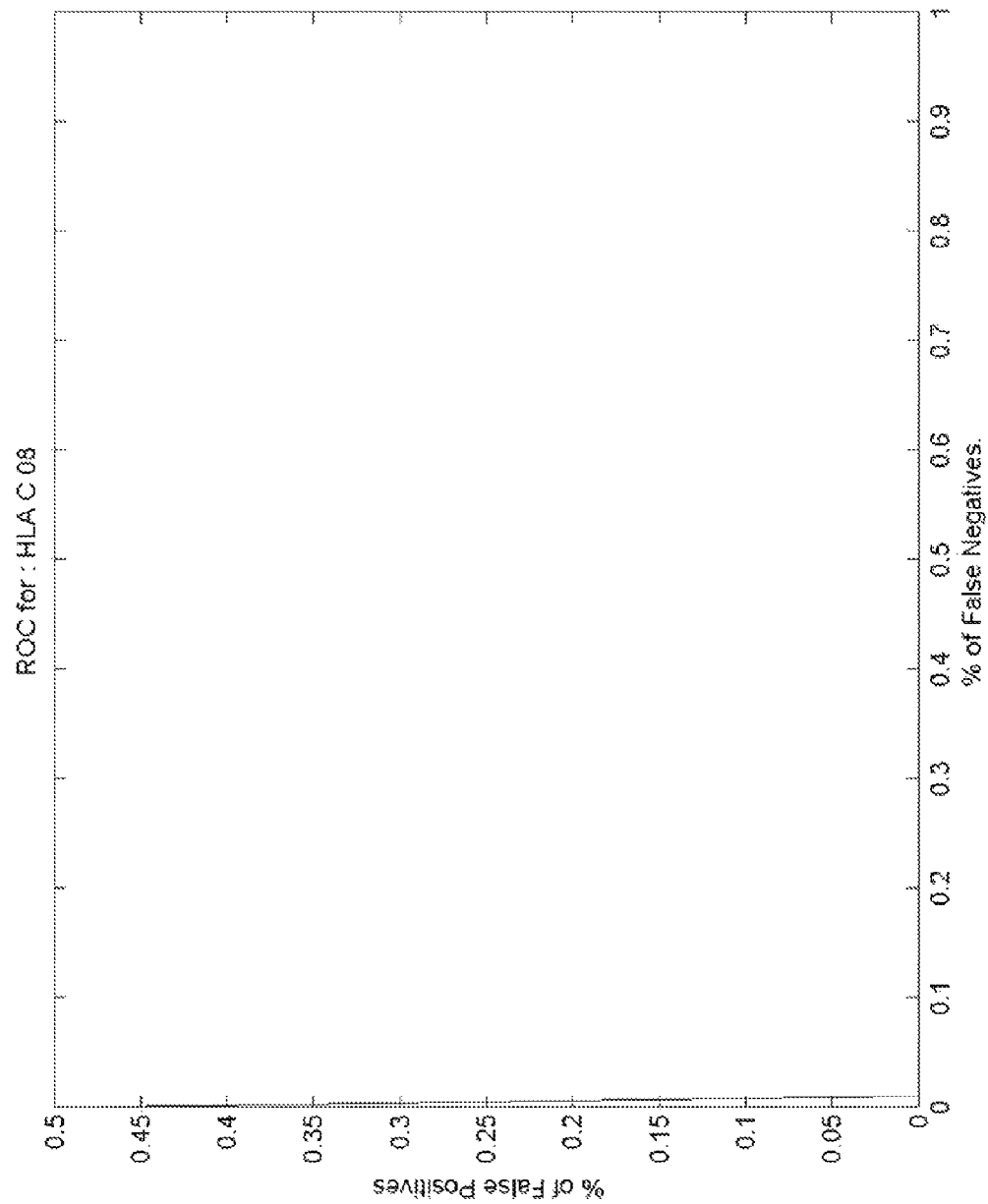
FIGS. 15a-f show ROC curves demonstrating the performance of an adaptive threading predictor trained on data from over 50 MHC molecules.
Figure 15B:
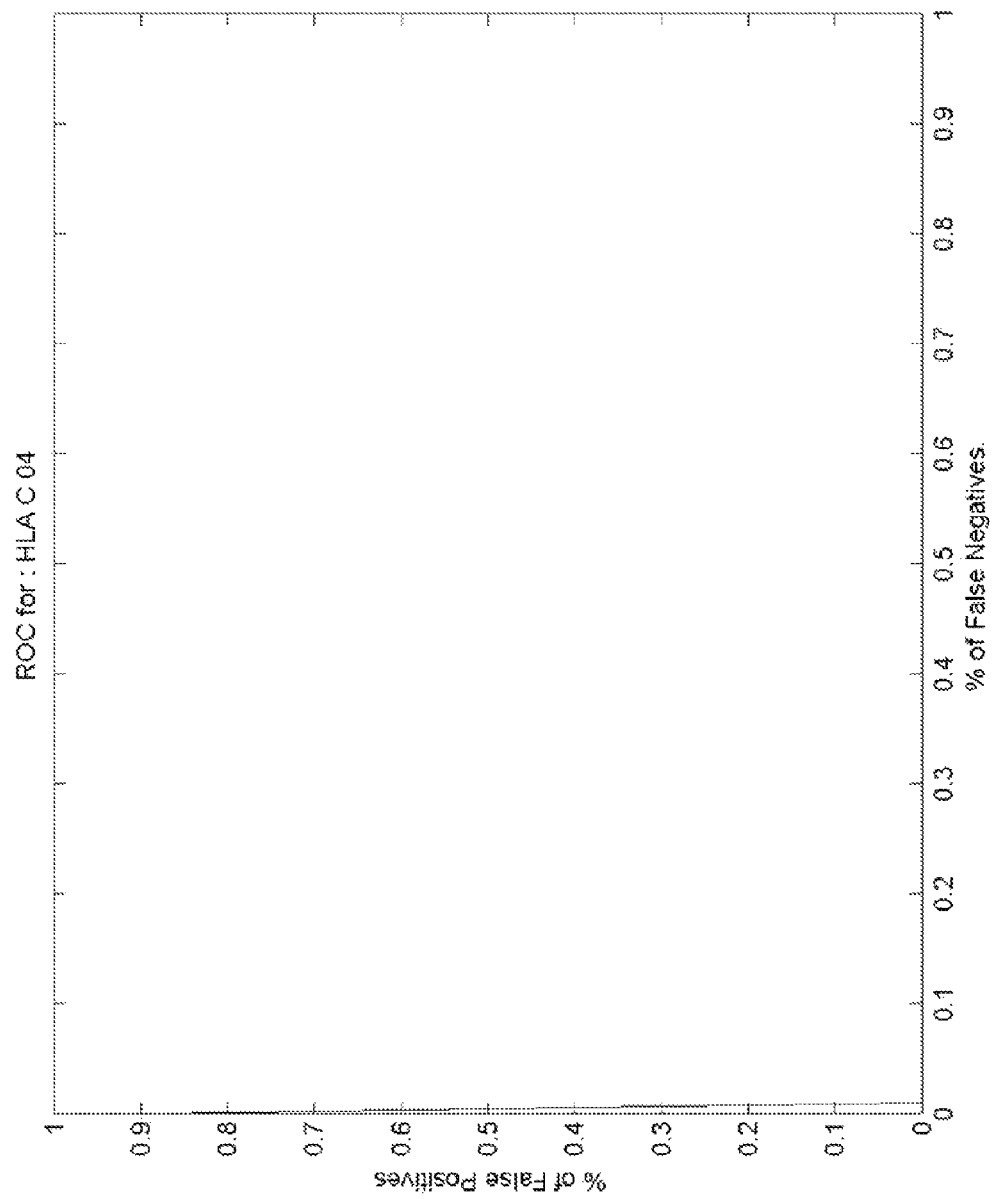
Figure 15C:
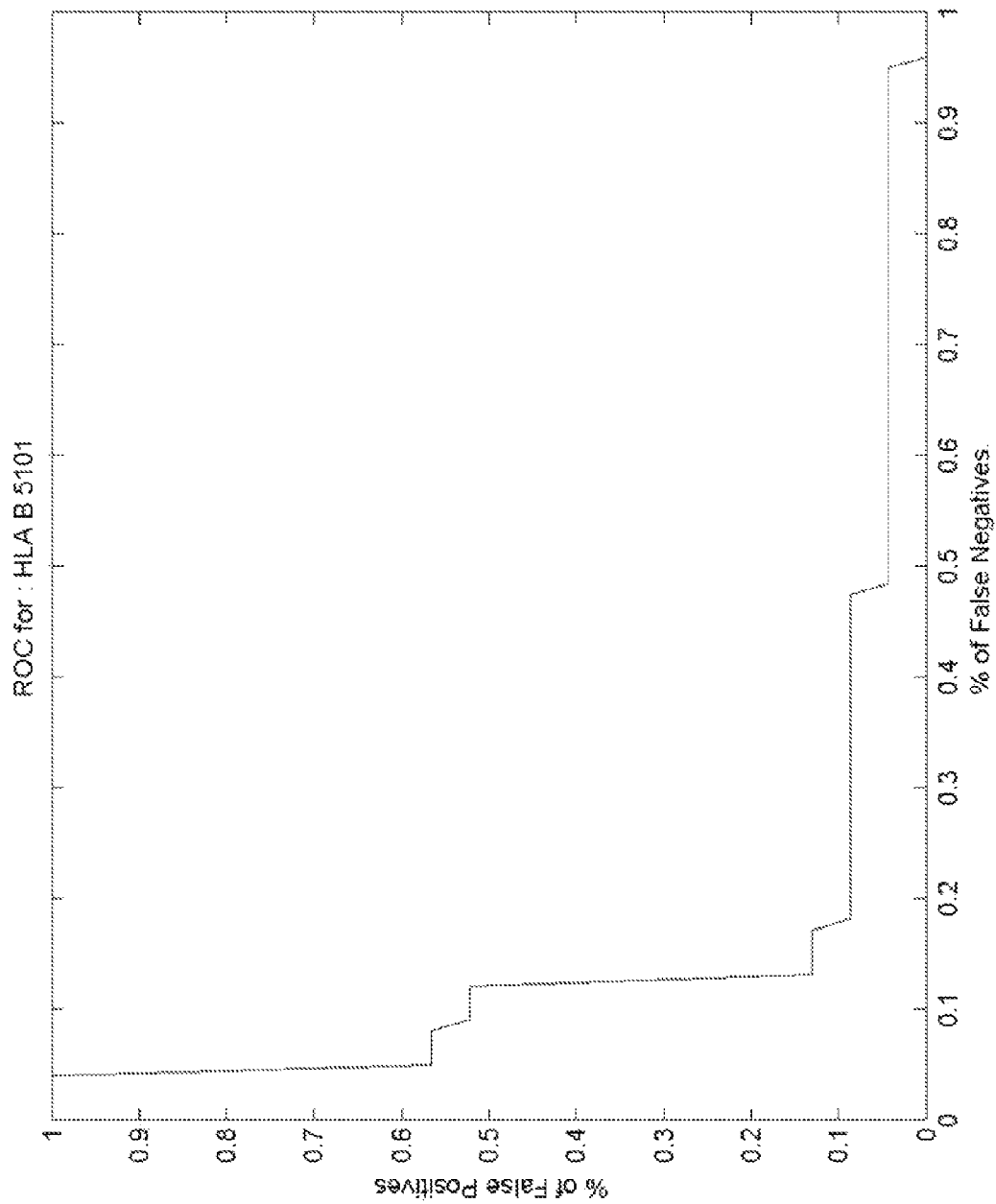
Figure 15D:
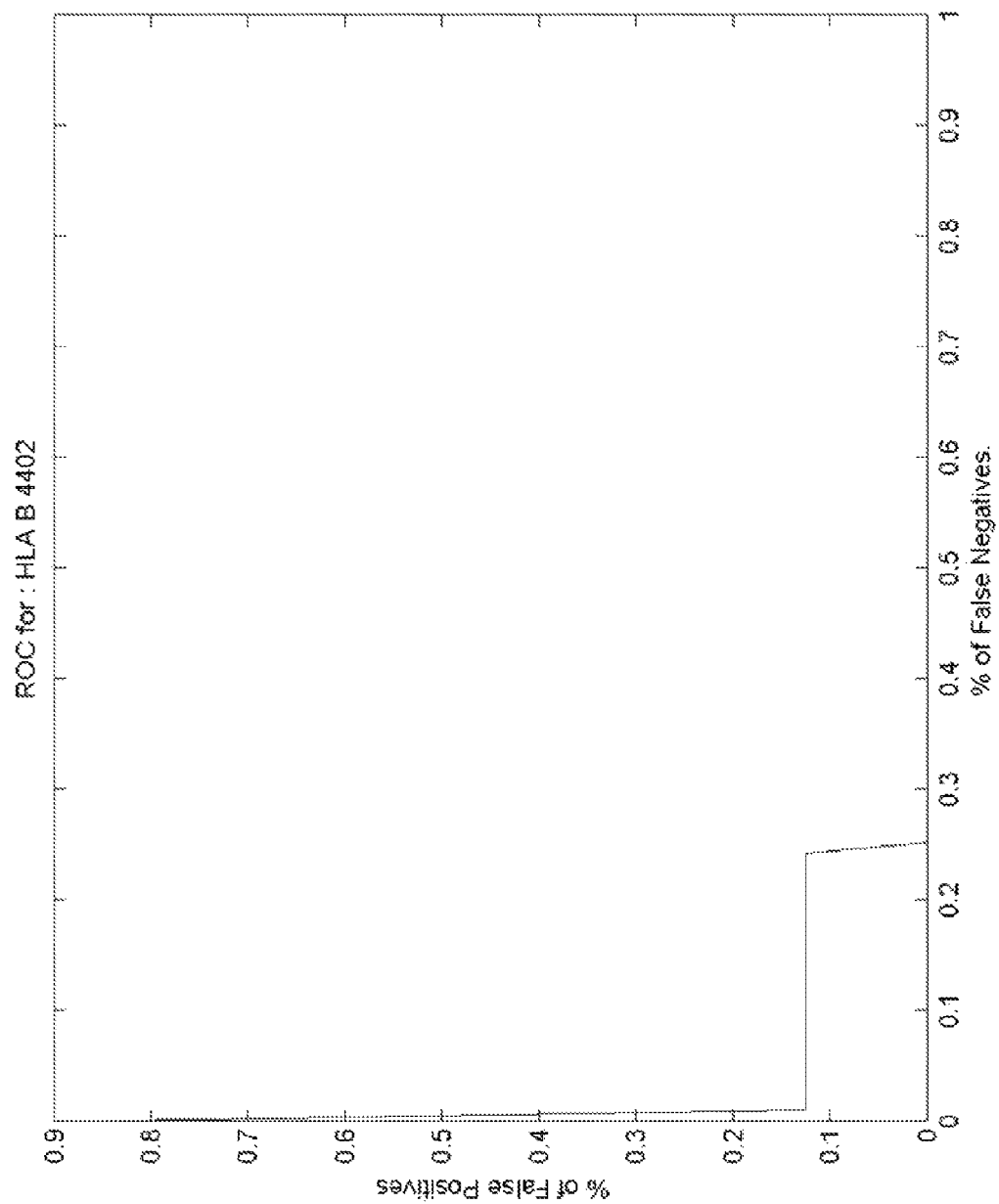
Figure 15E:
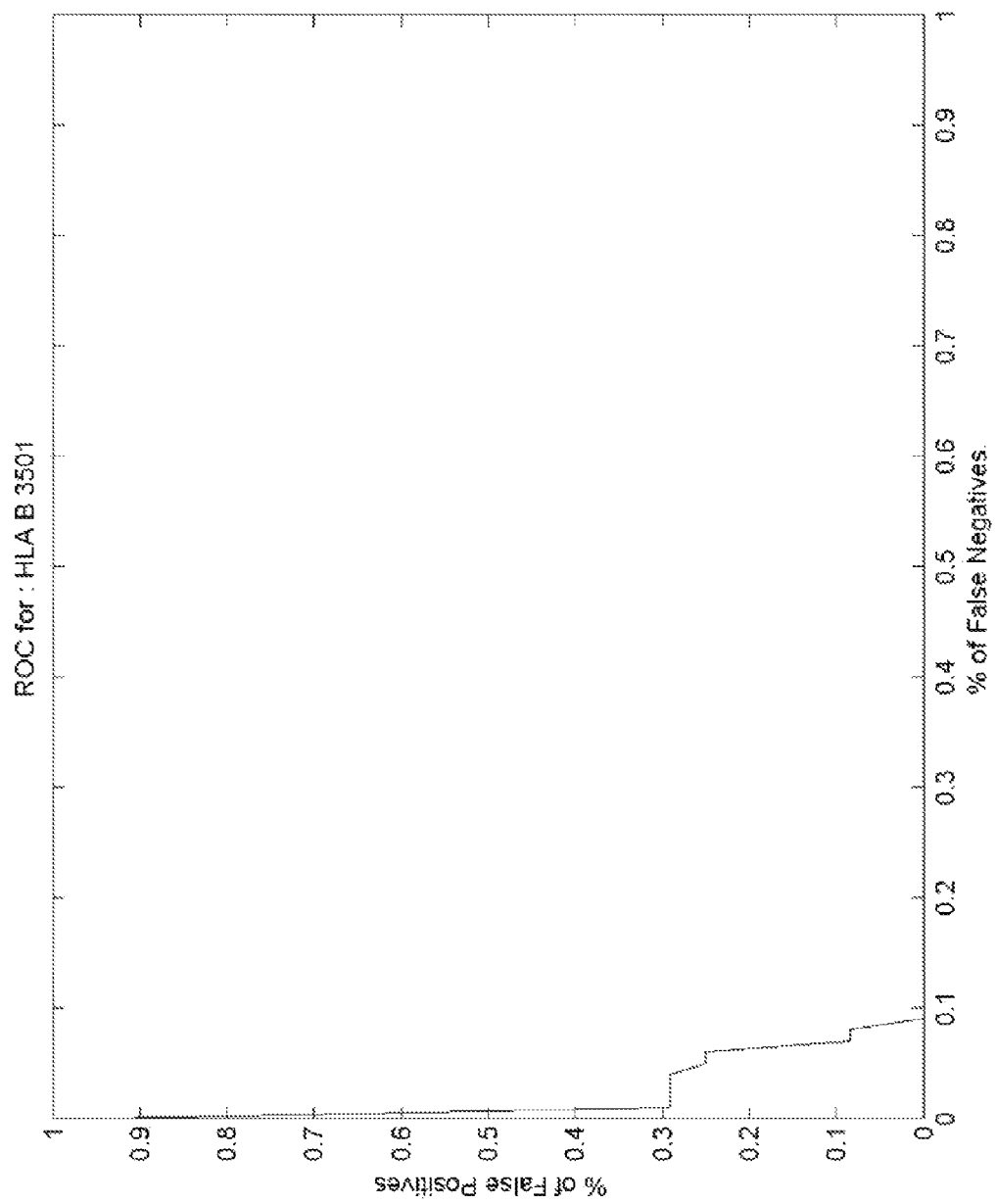
Figure 15F:
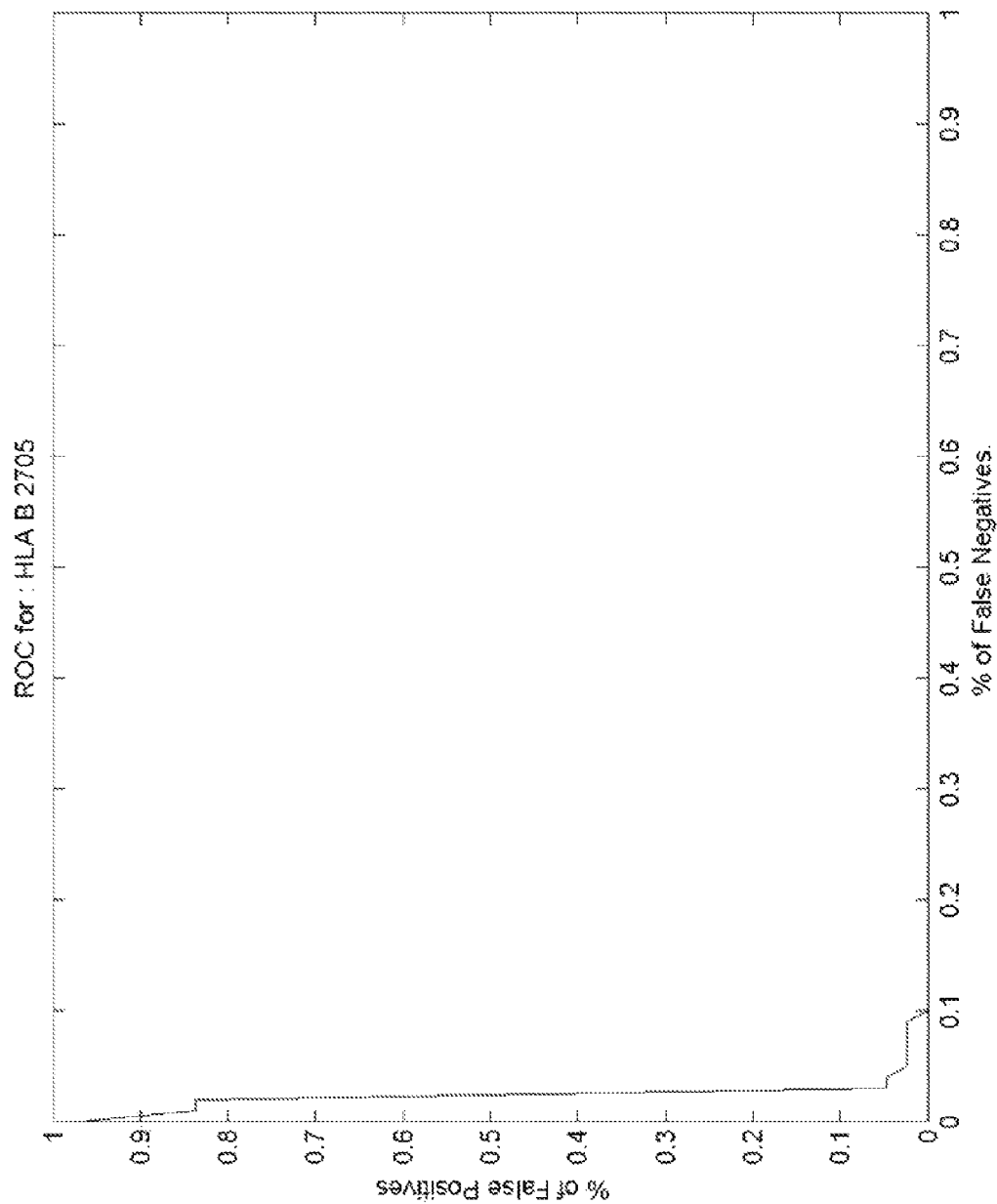
Figure 16A:
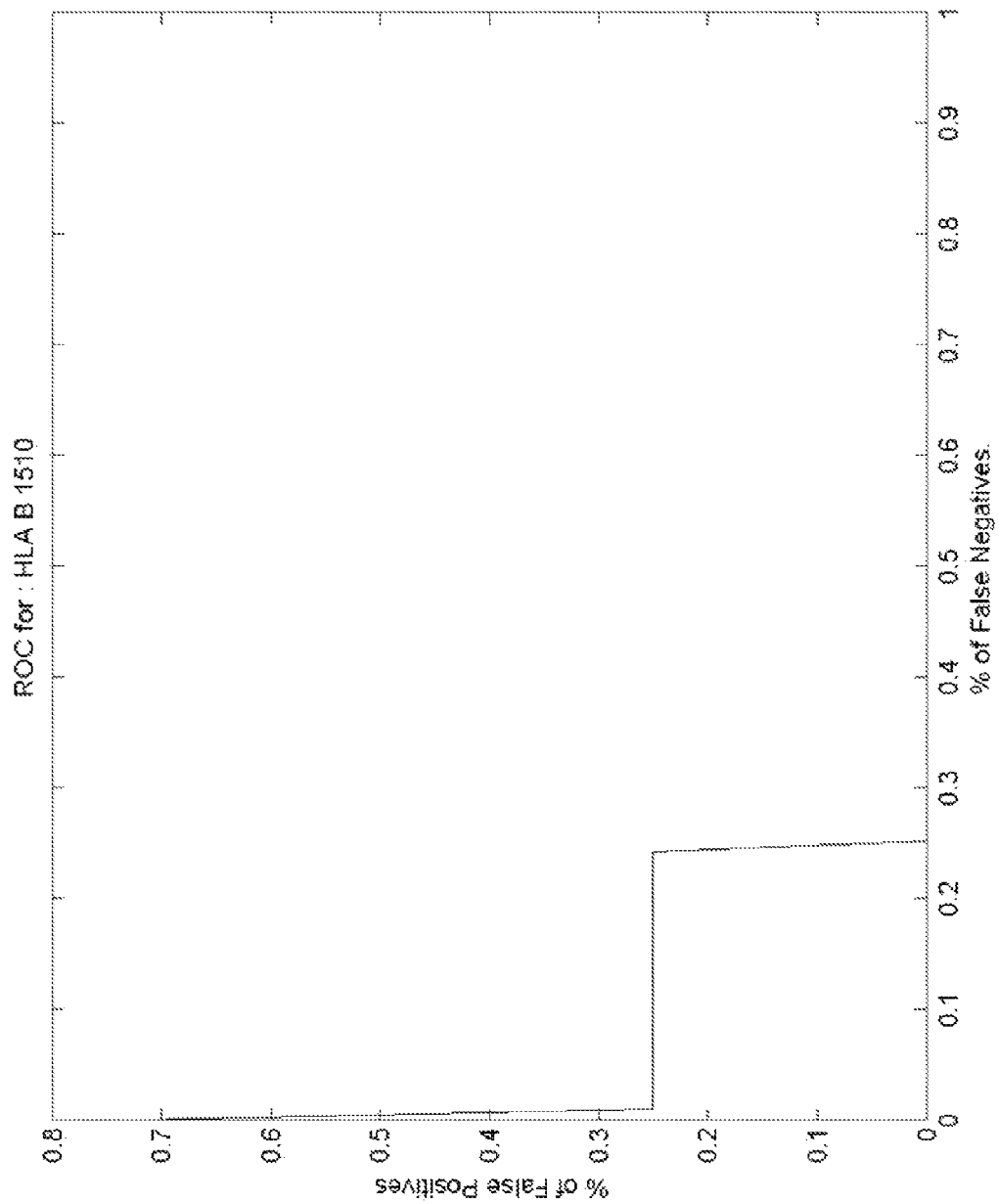
FIGS. 16a-f show ROC curves demonstrating the performance of an adaptive threading predictor trained on data from over 50 MHC molecules.
Figure 16B:
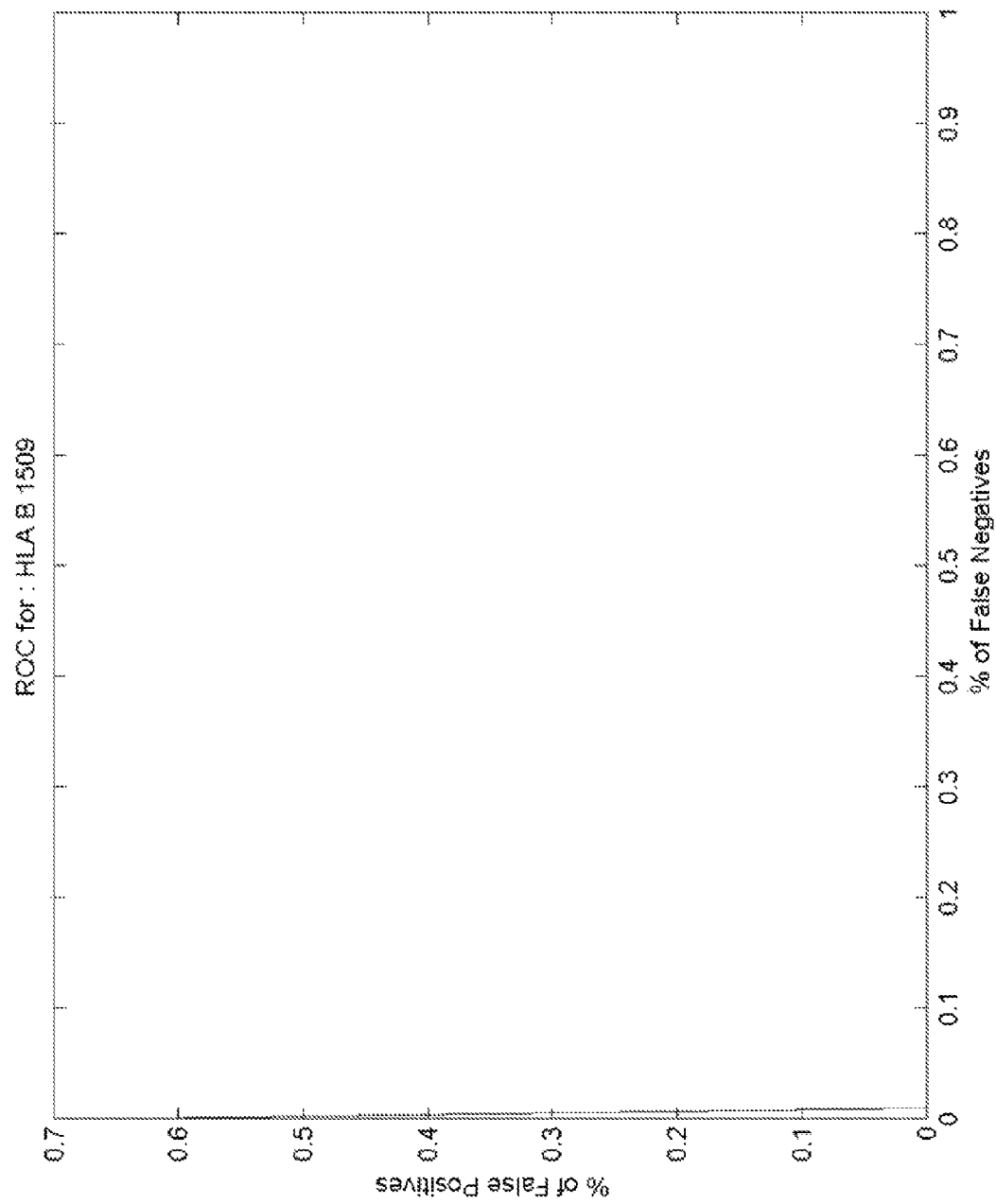
Figure 16C:
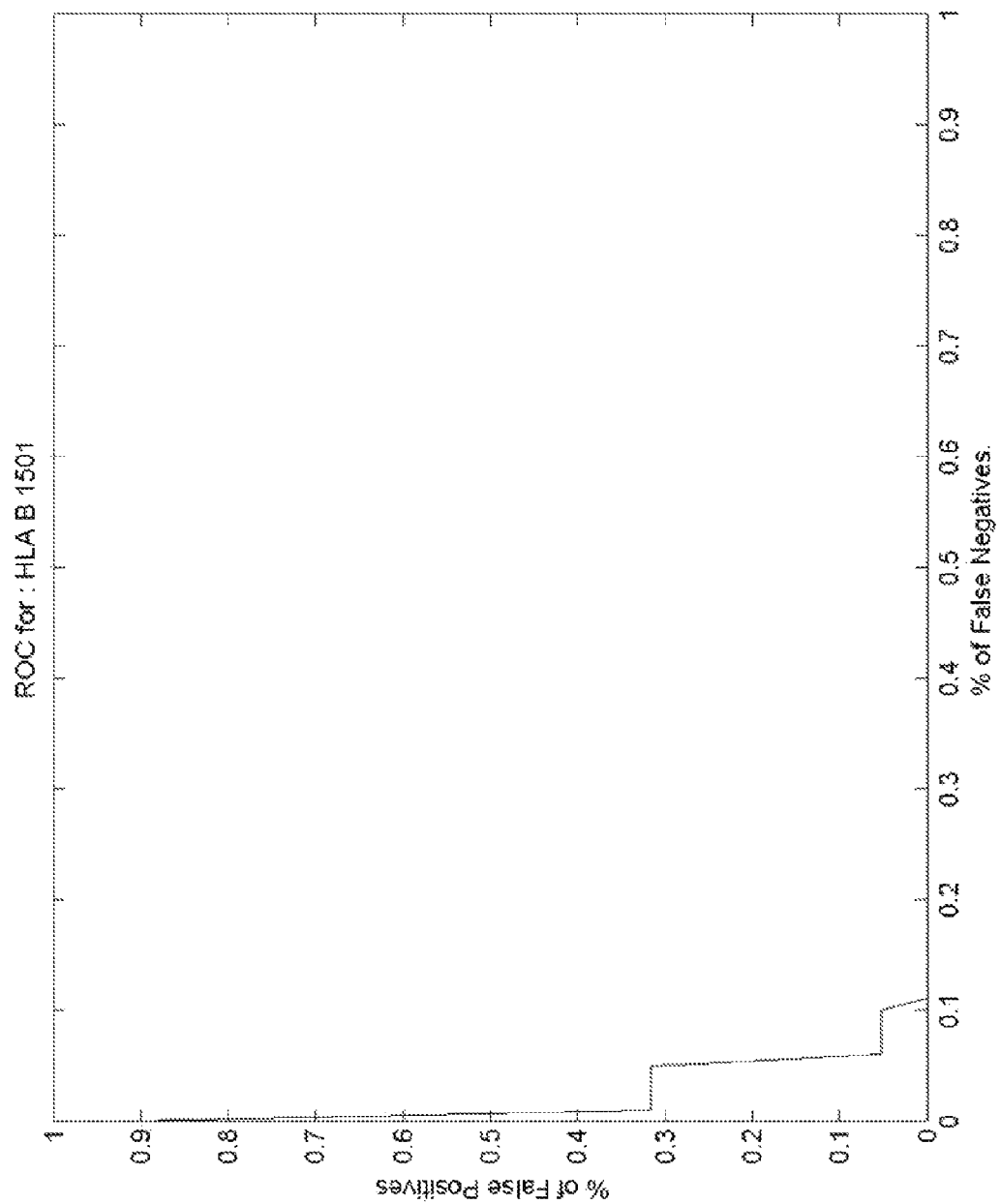
Figure 16D:
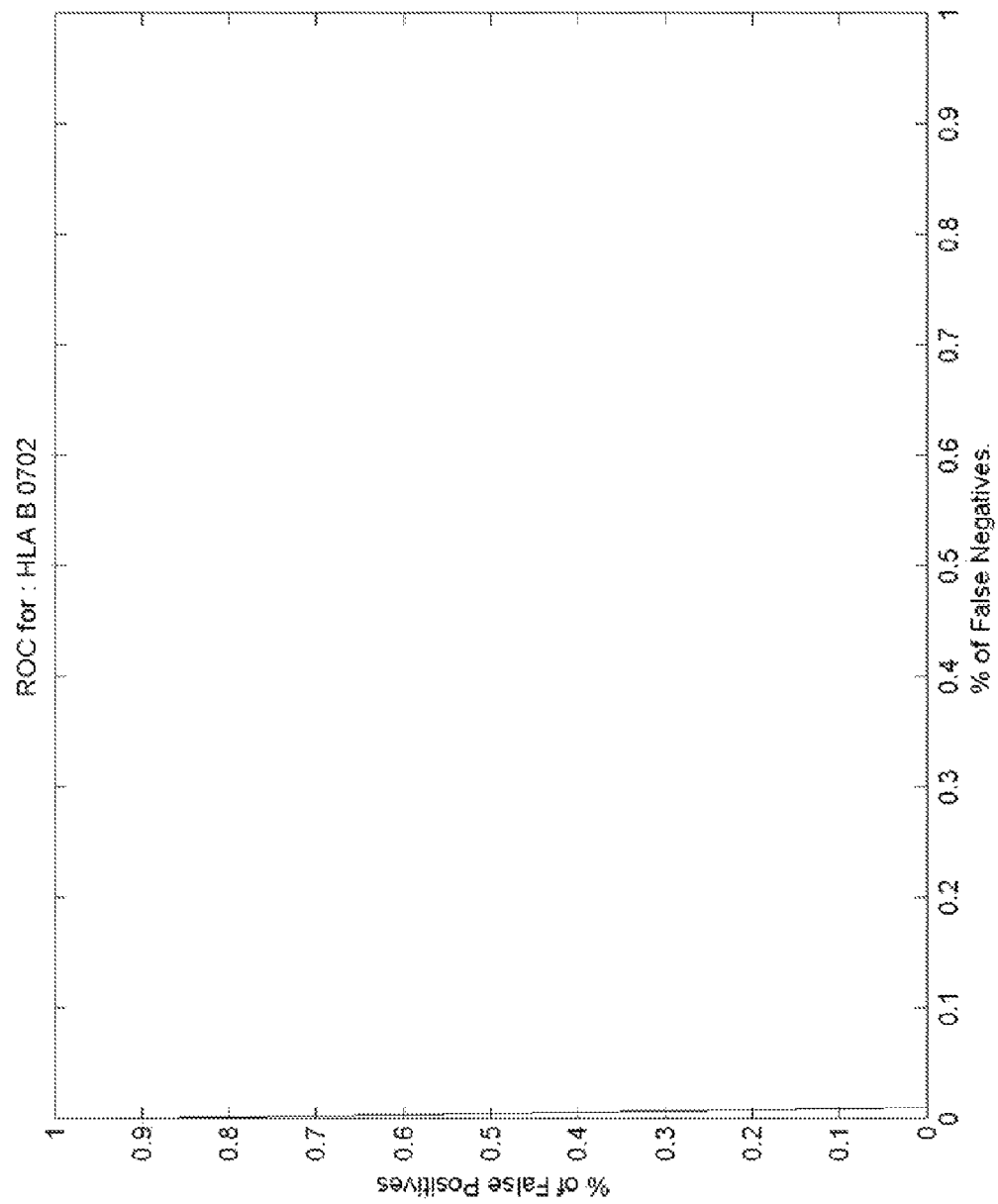
Figure 16E:
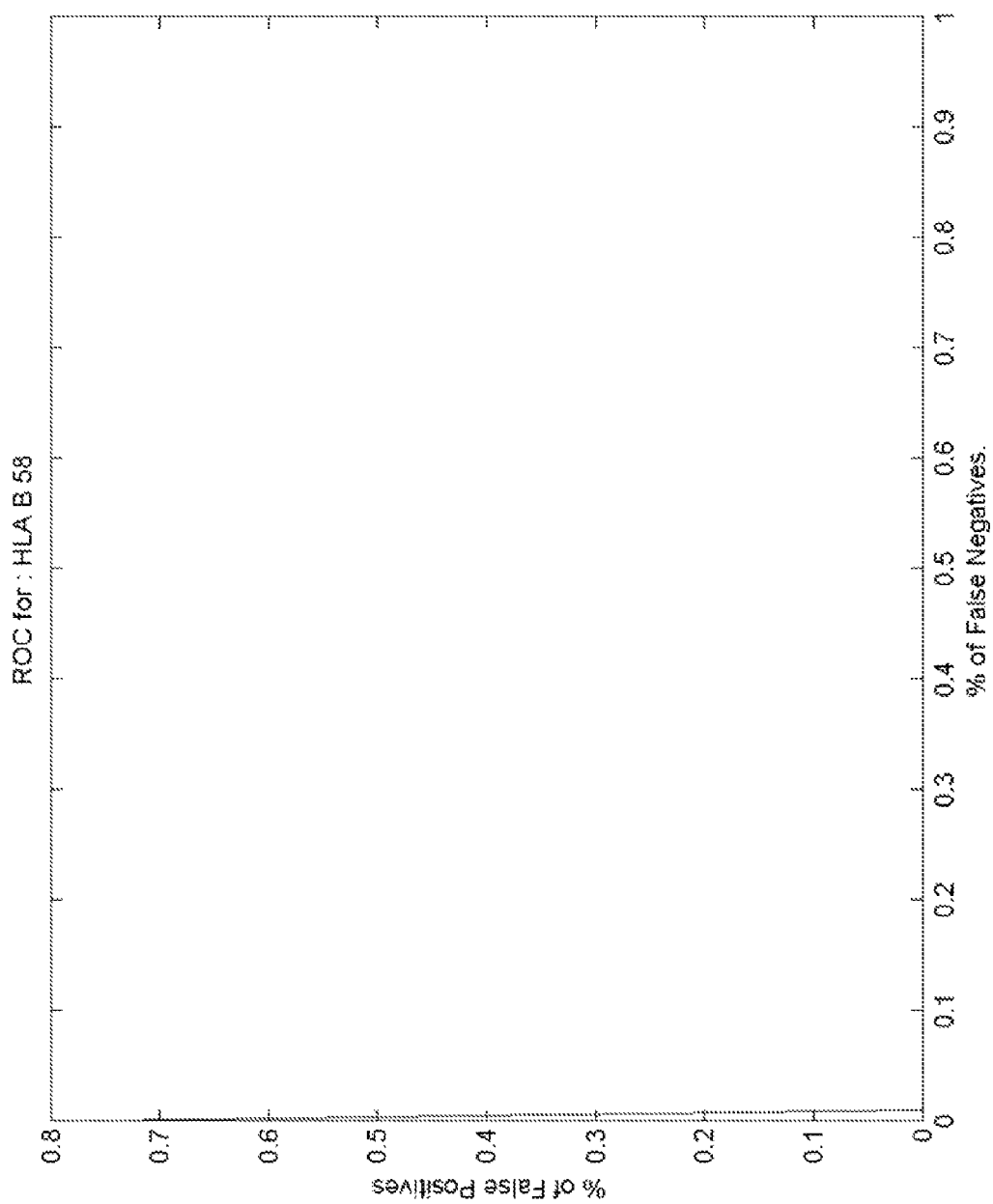
Figure 16F:
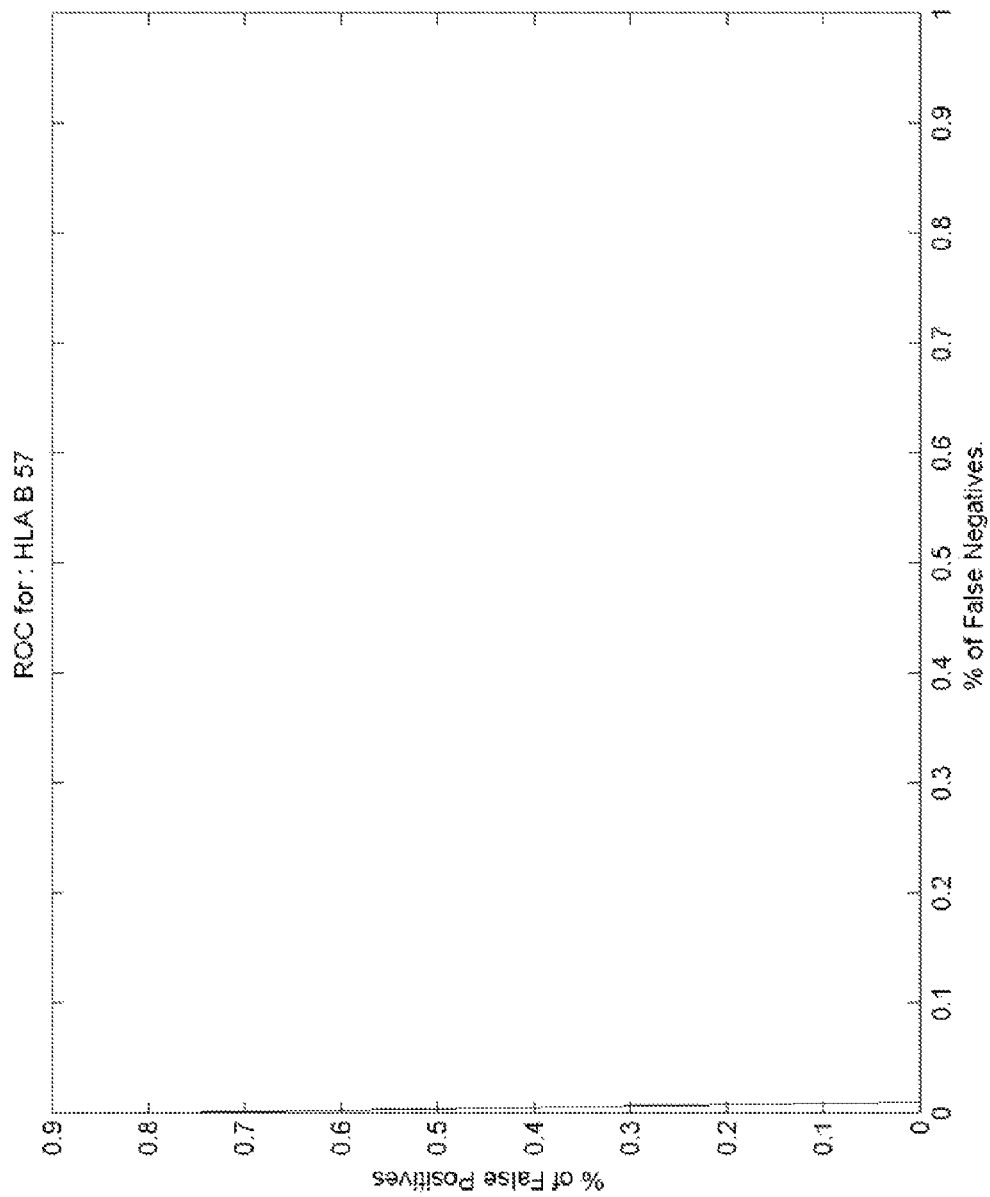
Figure 17A:
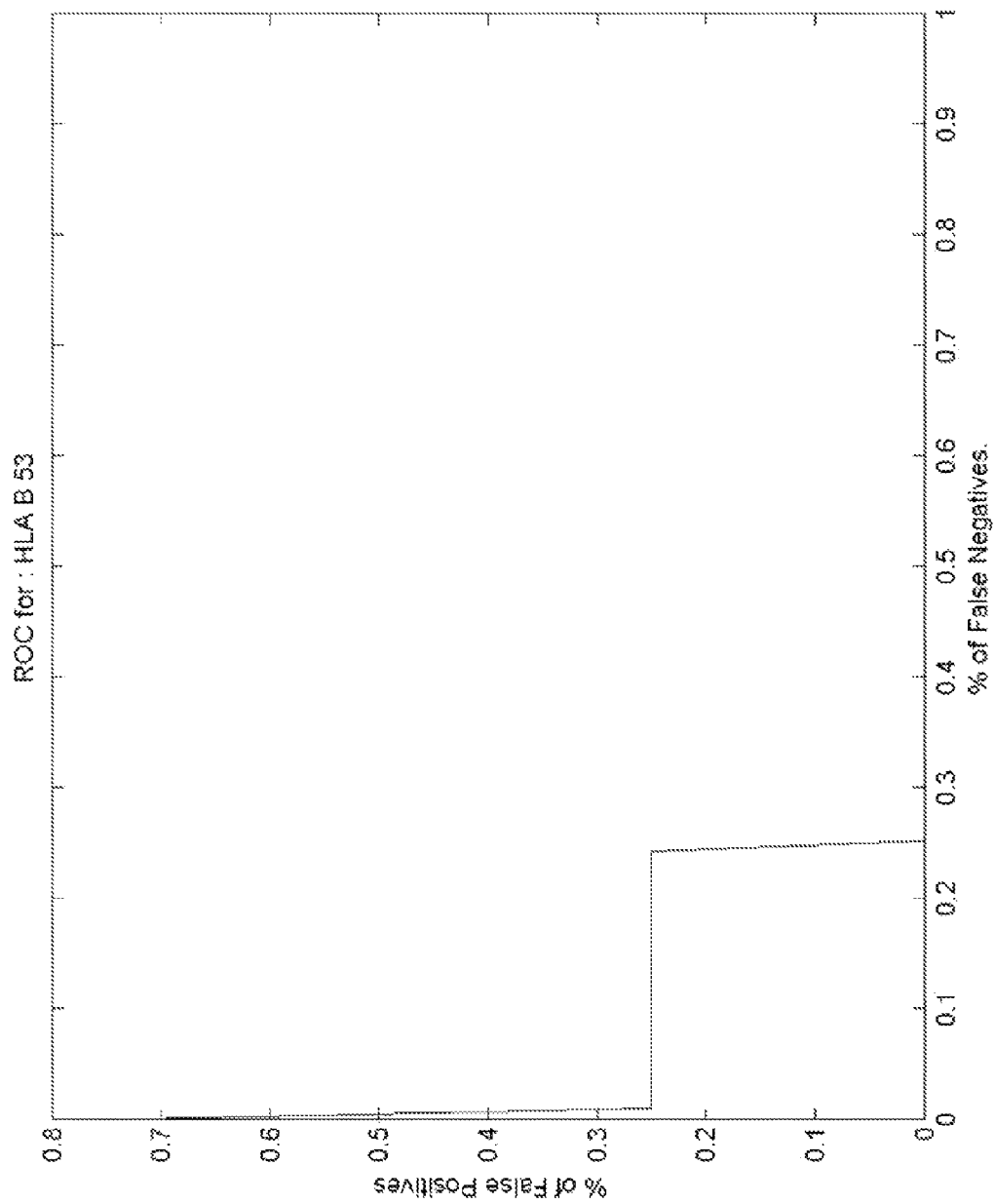
FIGS. 17a-f show ROC curves demonstrating the performance of an adaptive threading predictor trained on data from over 50 MHC molecules.
Figure 17B:
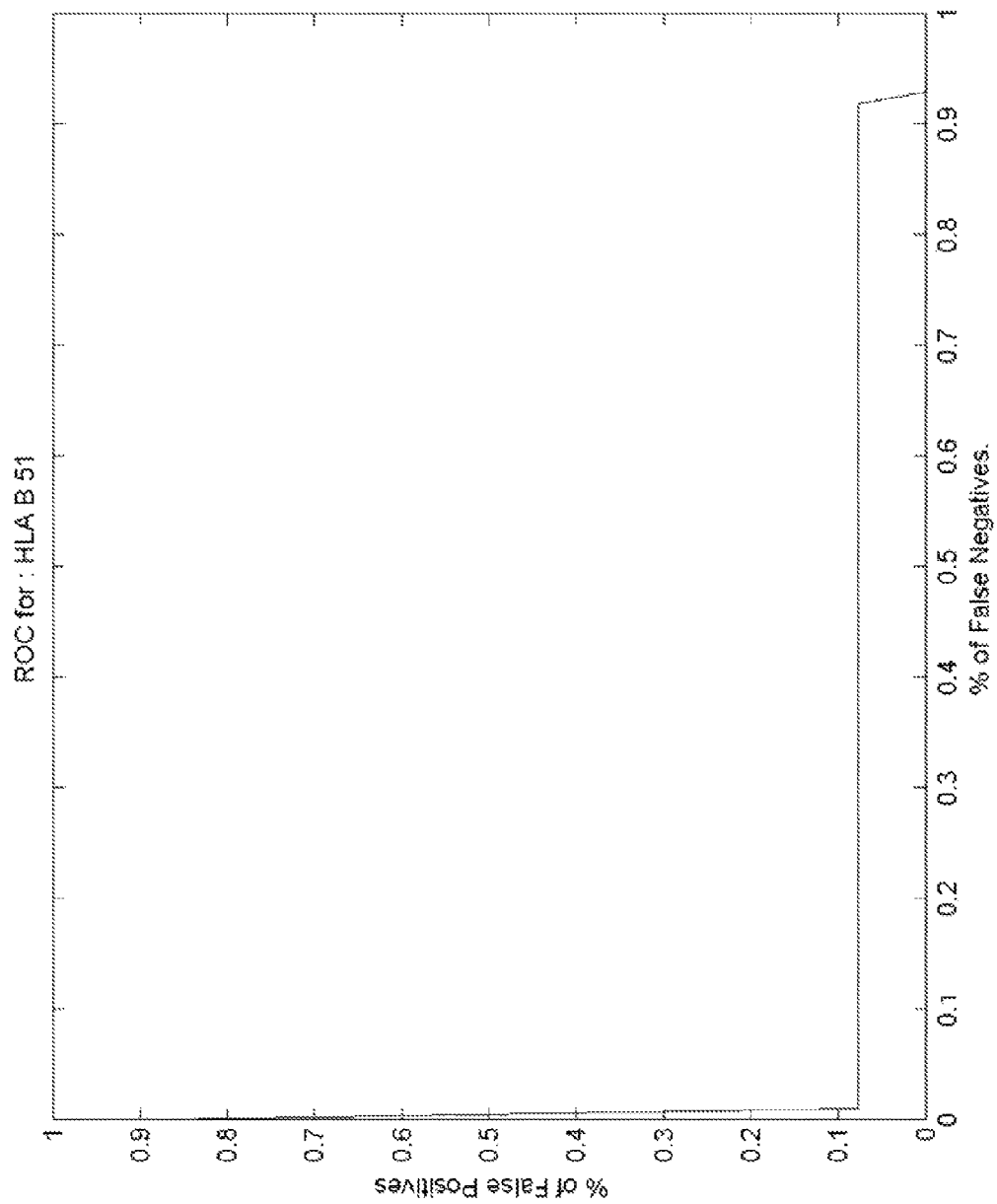
Figure 17C:
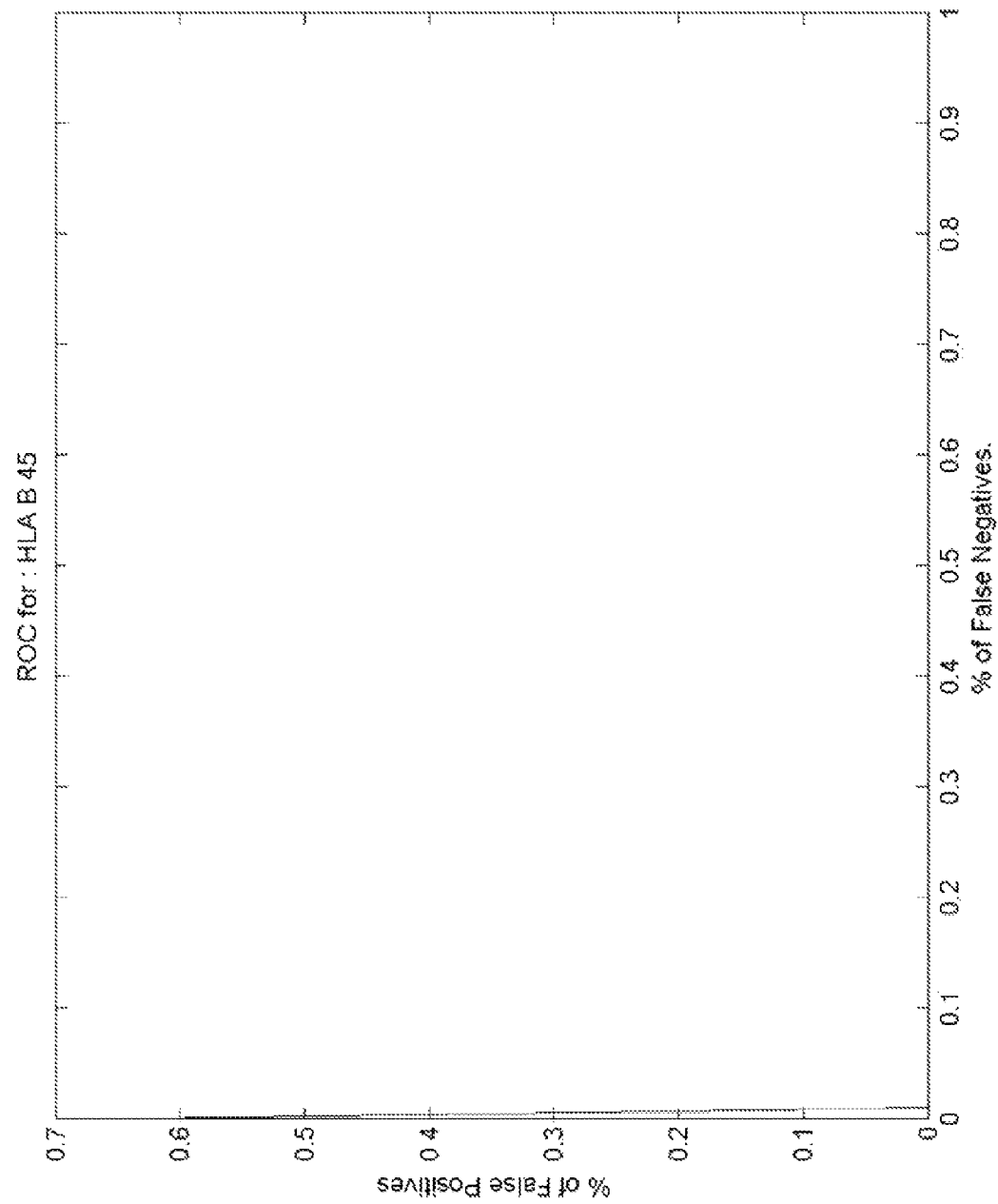
Figure 17D:
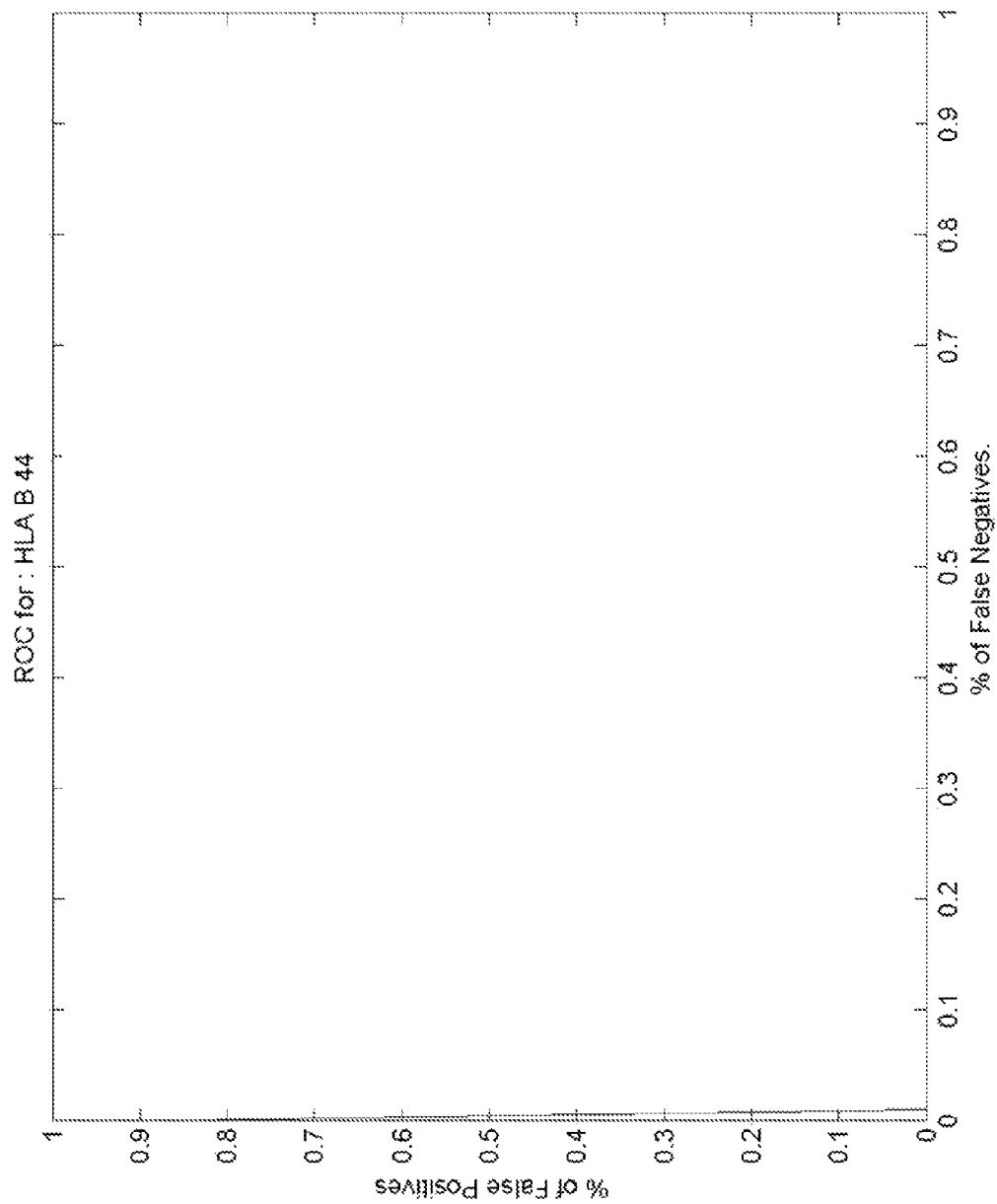
Figure 17E:
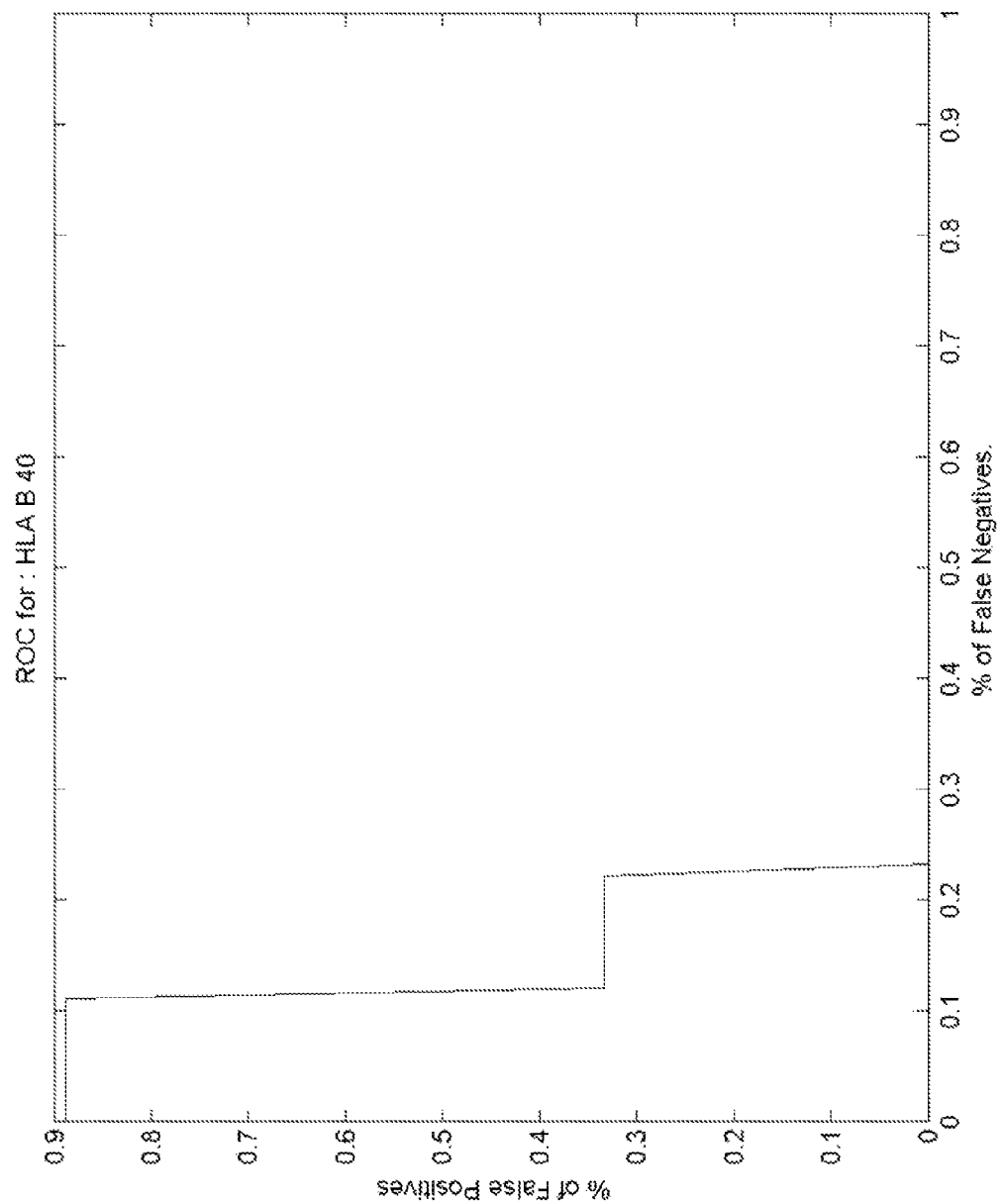
Figure 17F:
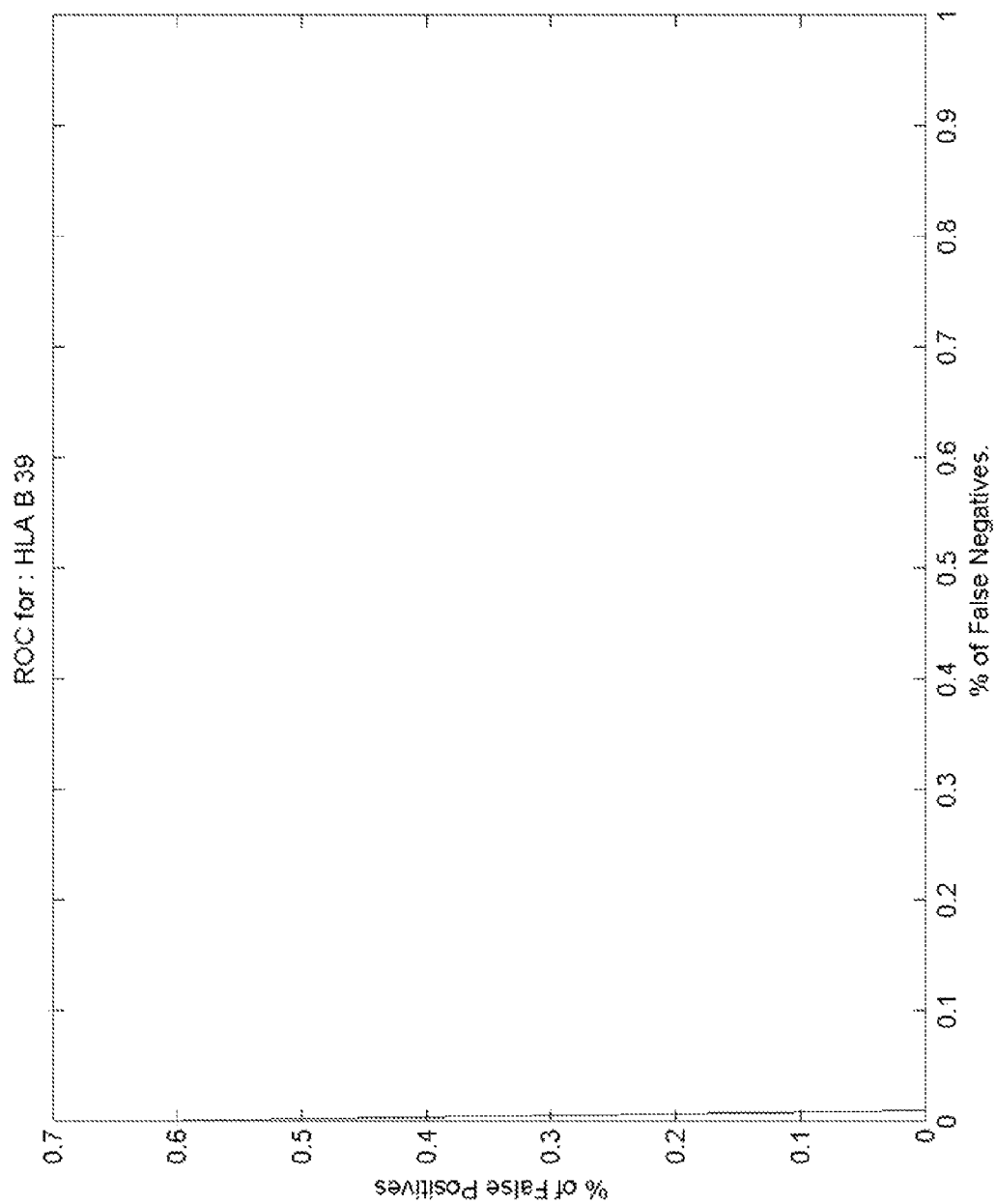
Figure 18B:
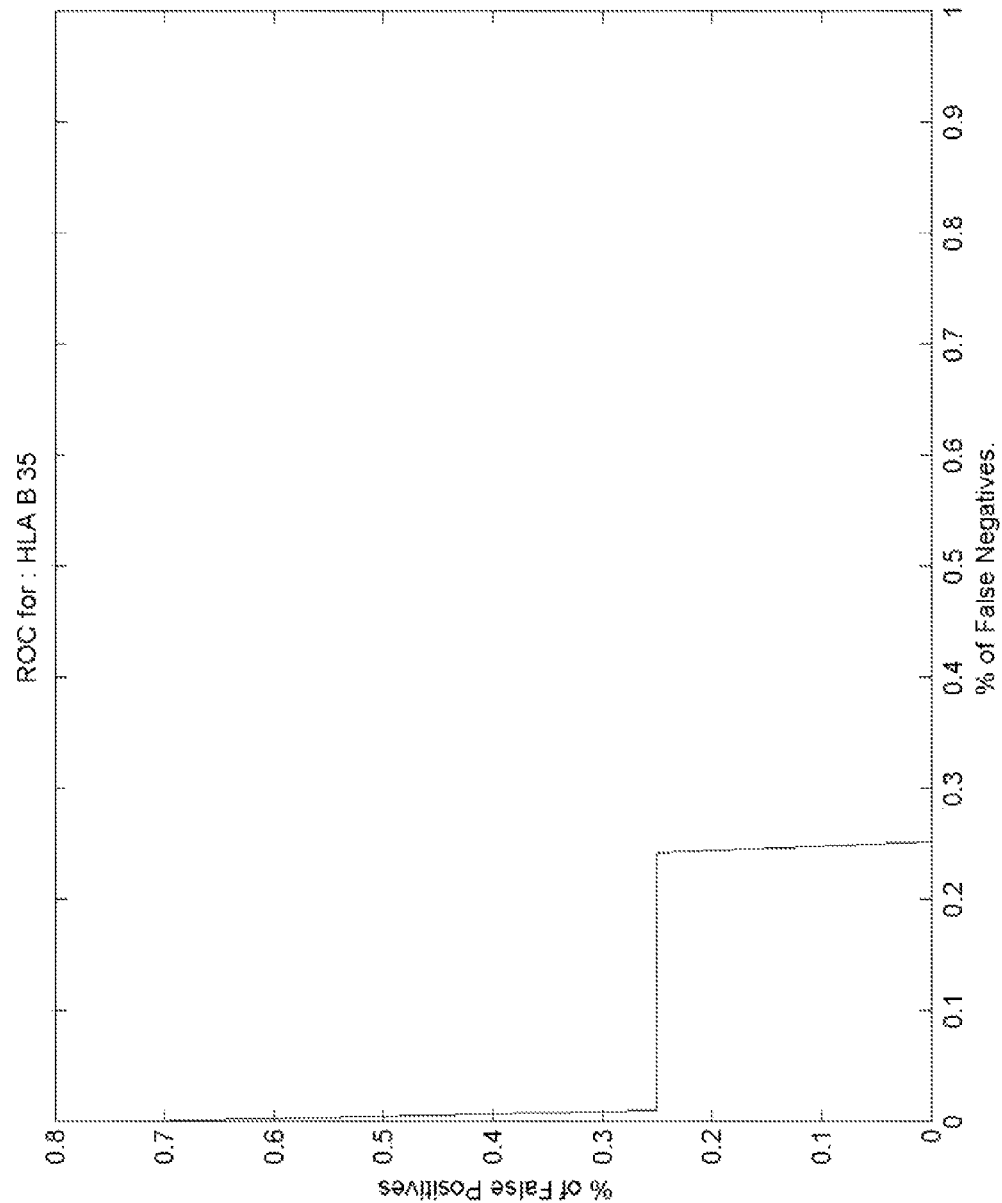
Figure 18C:
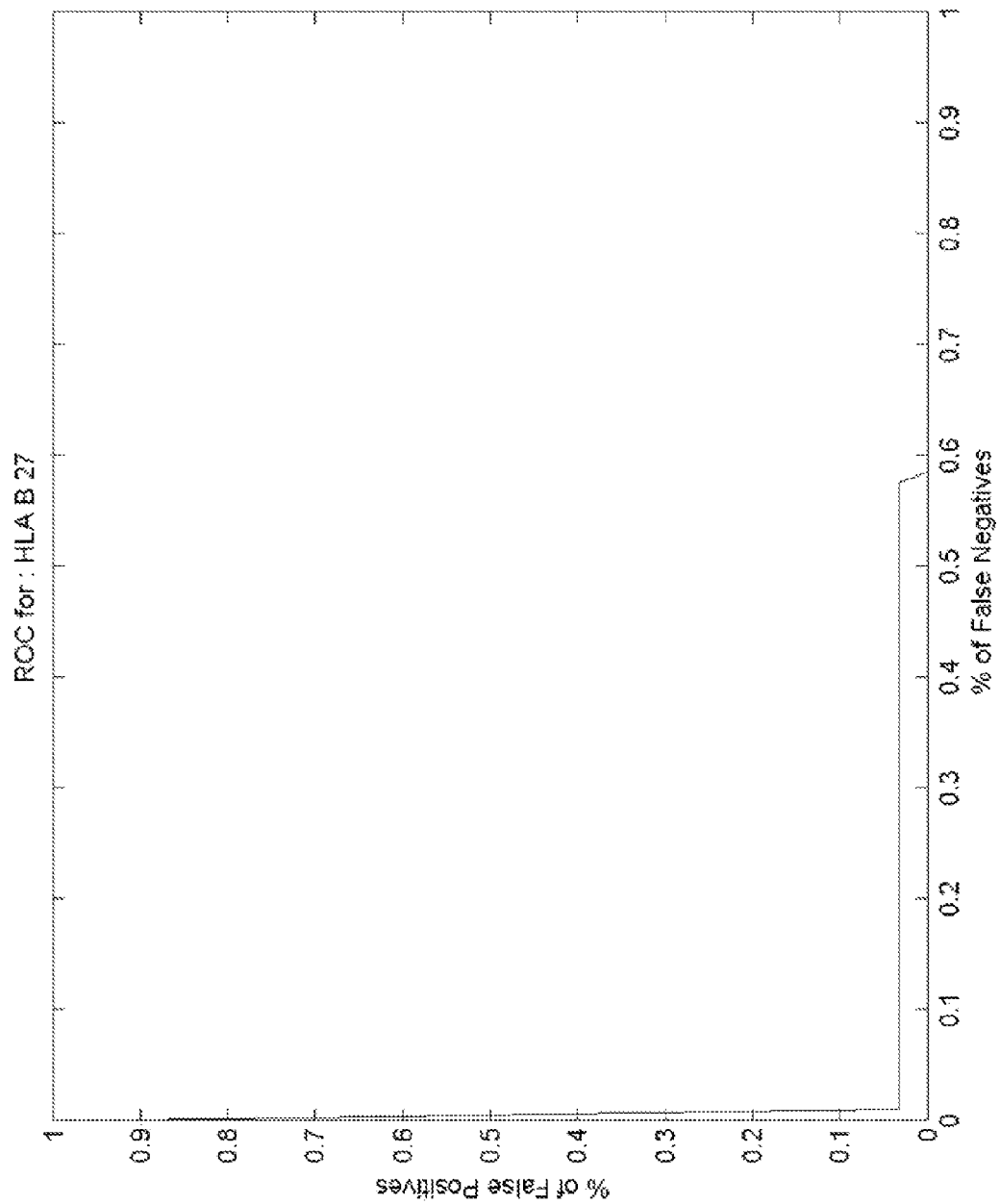
Figure 18D:
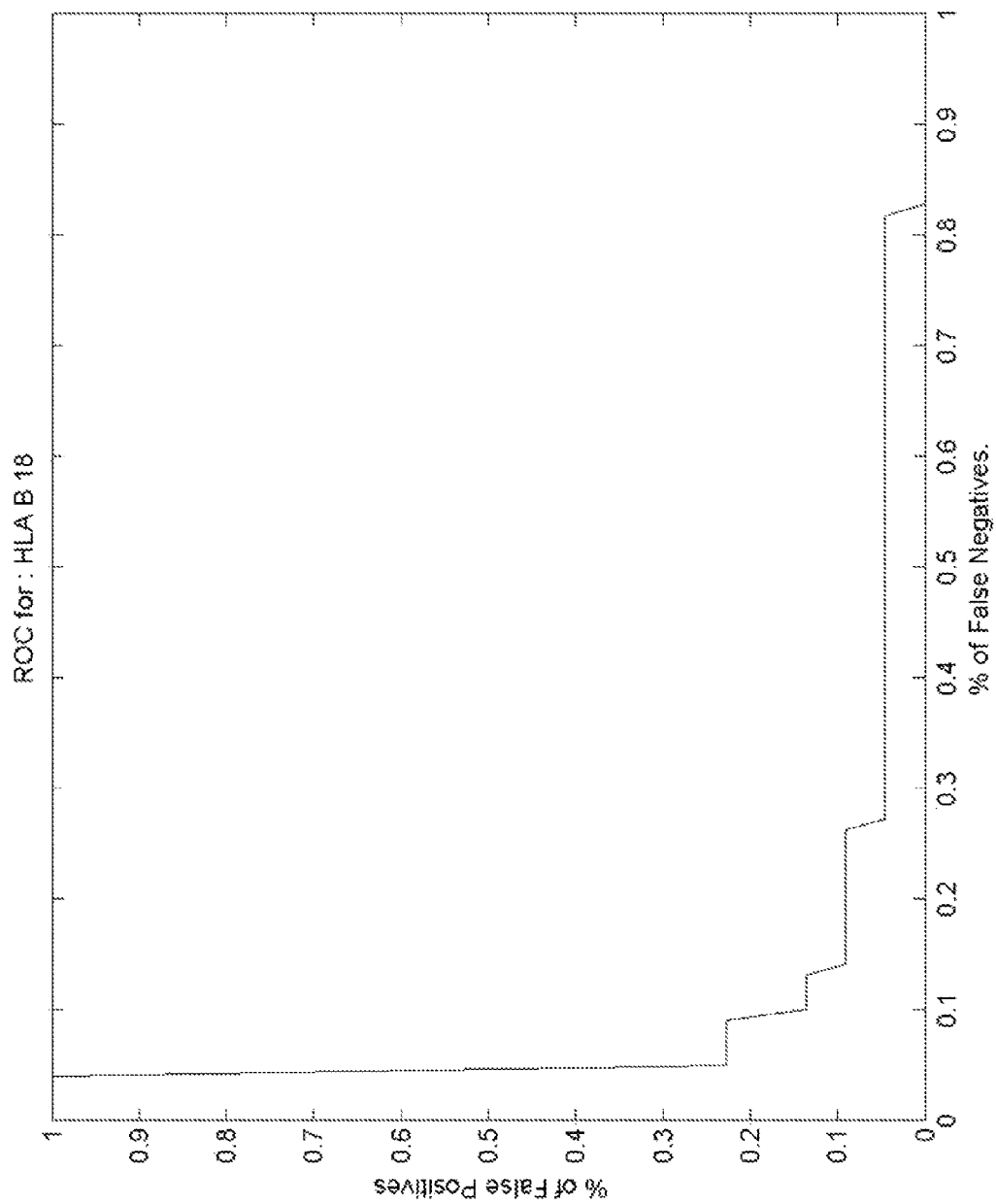
Figure 18E:
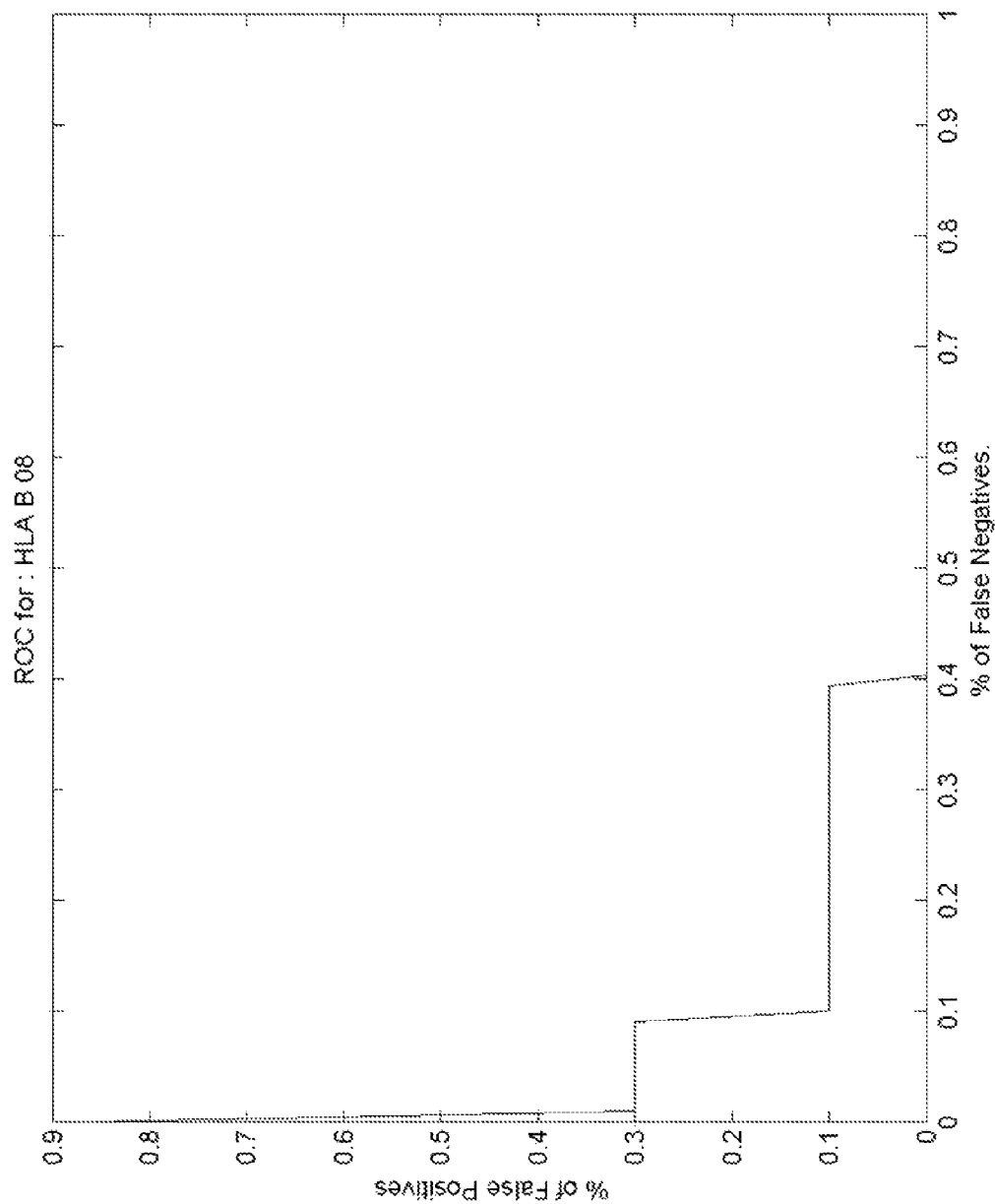
Figure 18F:
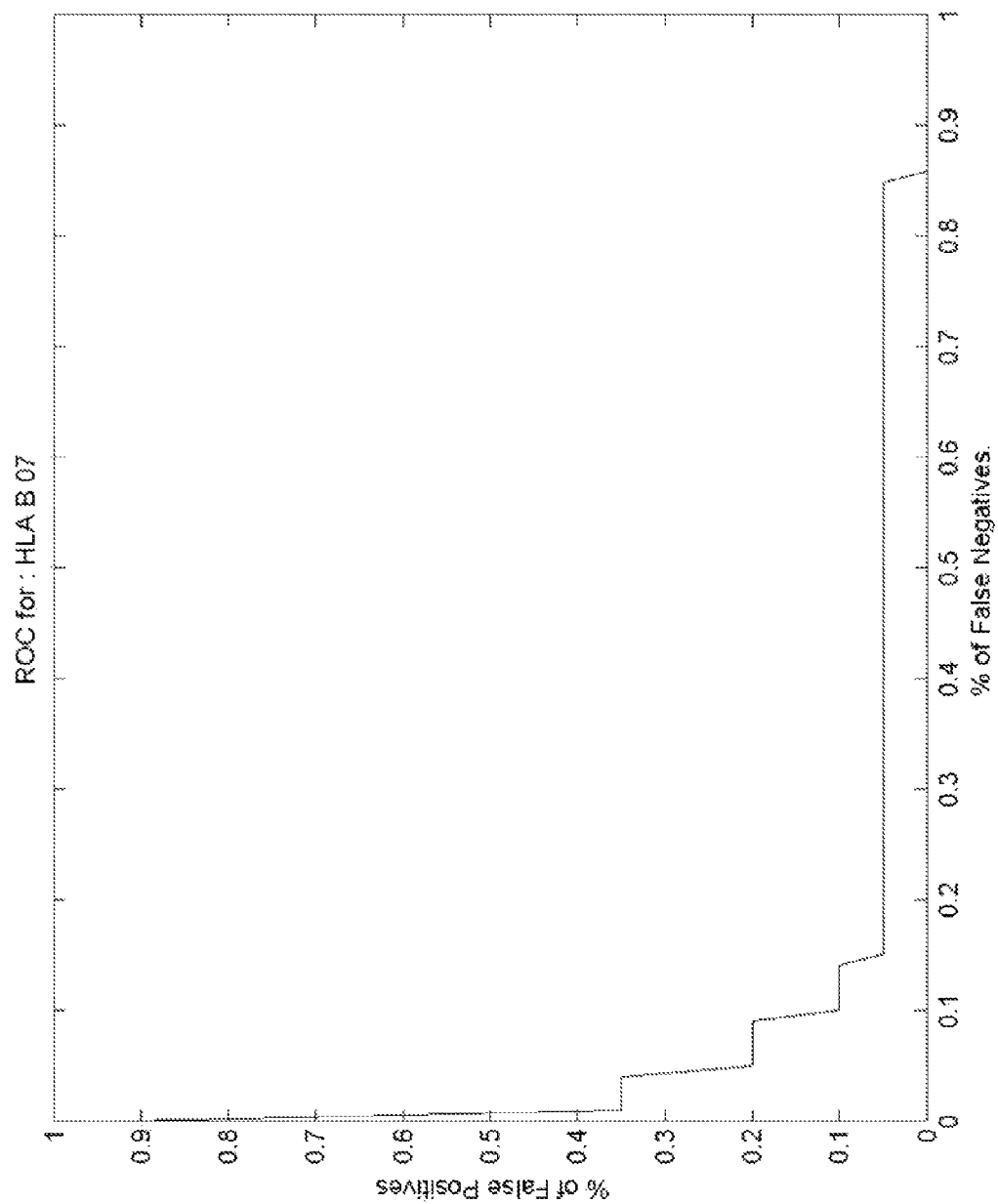
Figure 19A:
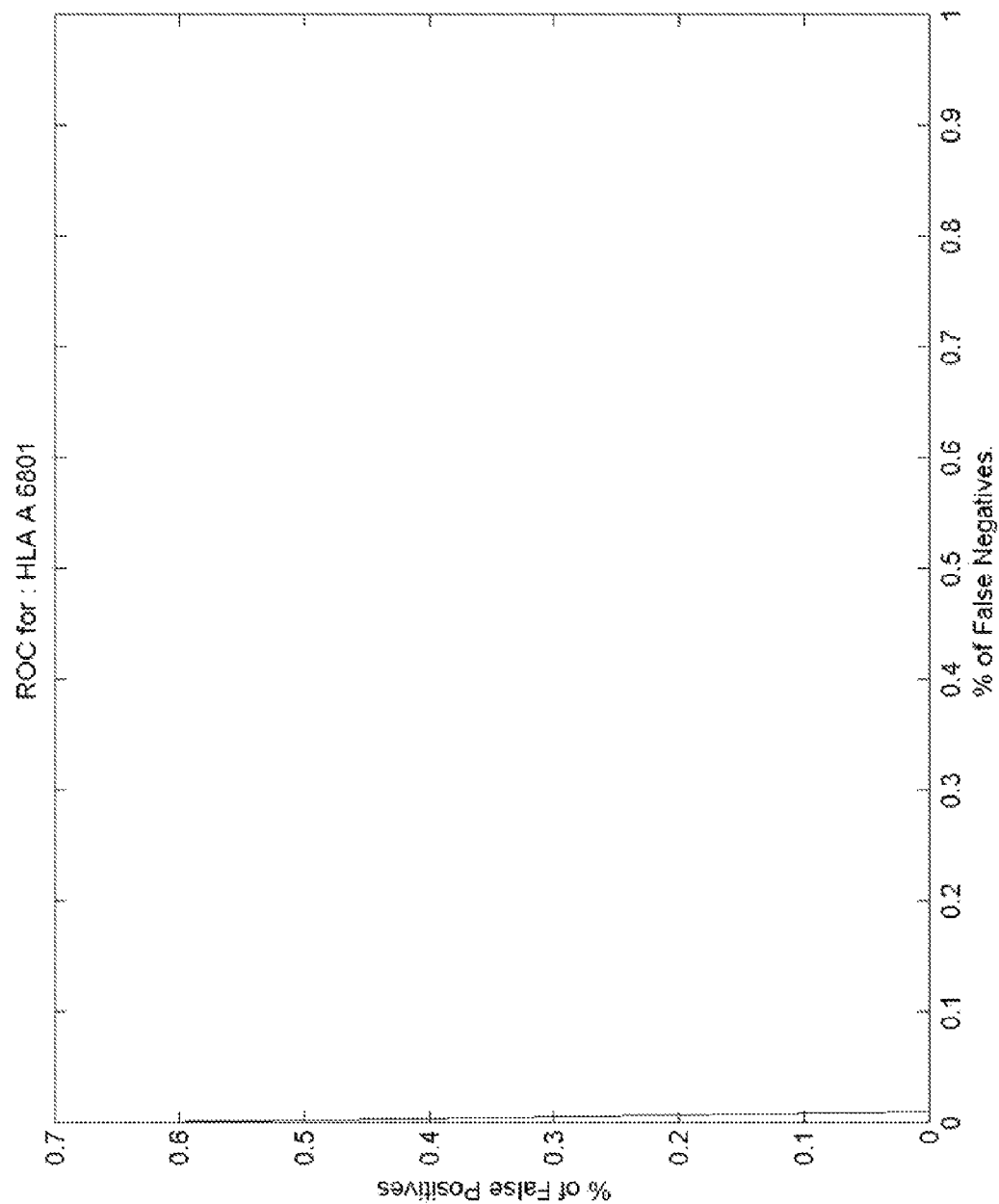
FIGS. 19a-f show ROC curves demonstrating the performance of an adaptive threading predictor trained on data from over 50 MHC molecules.
Figure 19B:
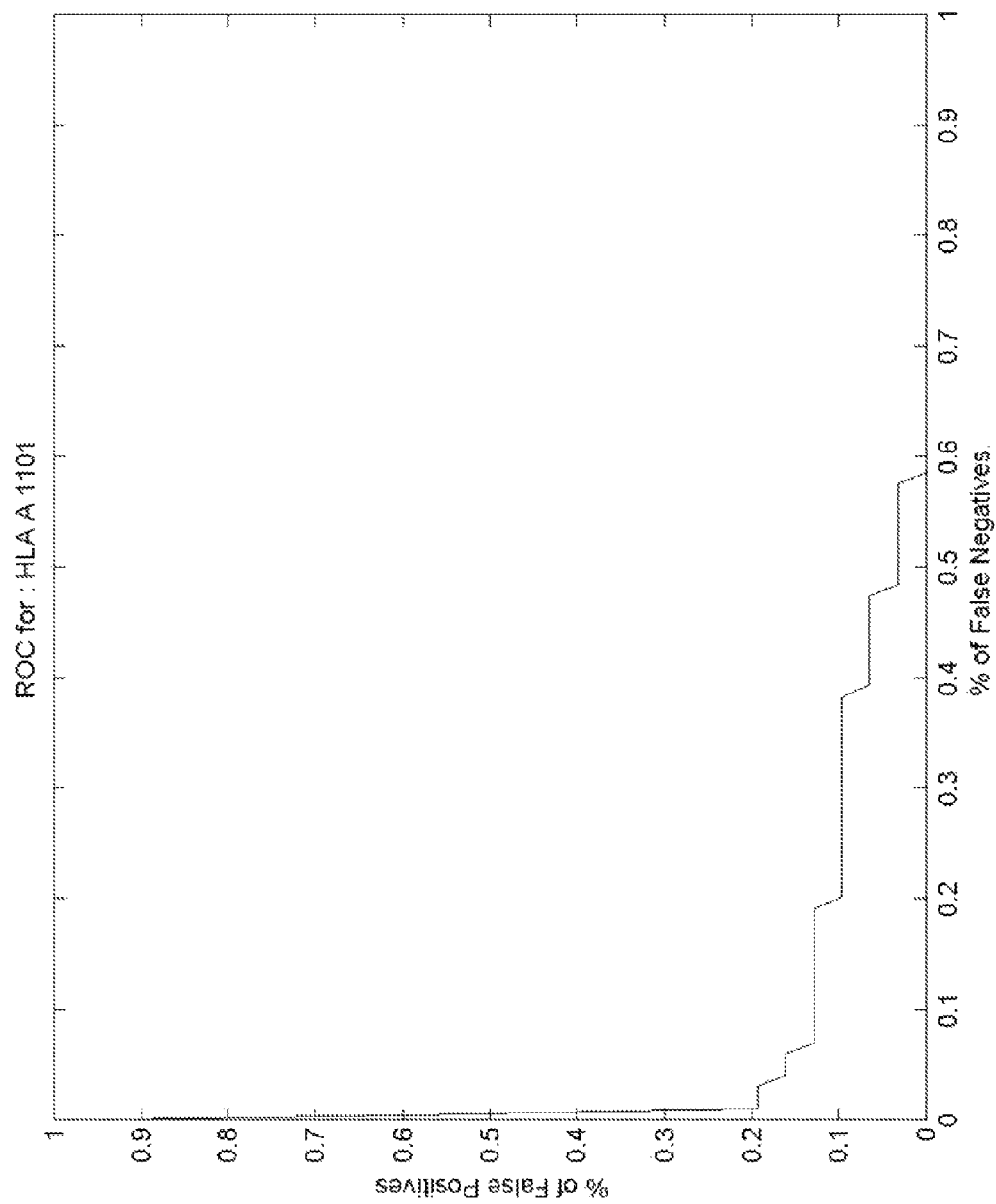
Figure 19C:
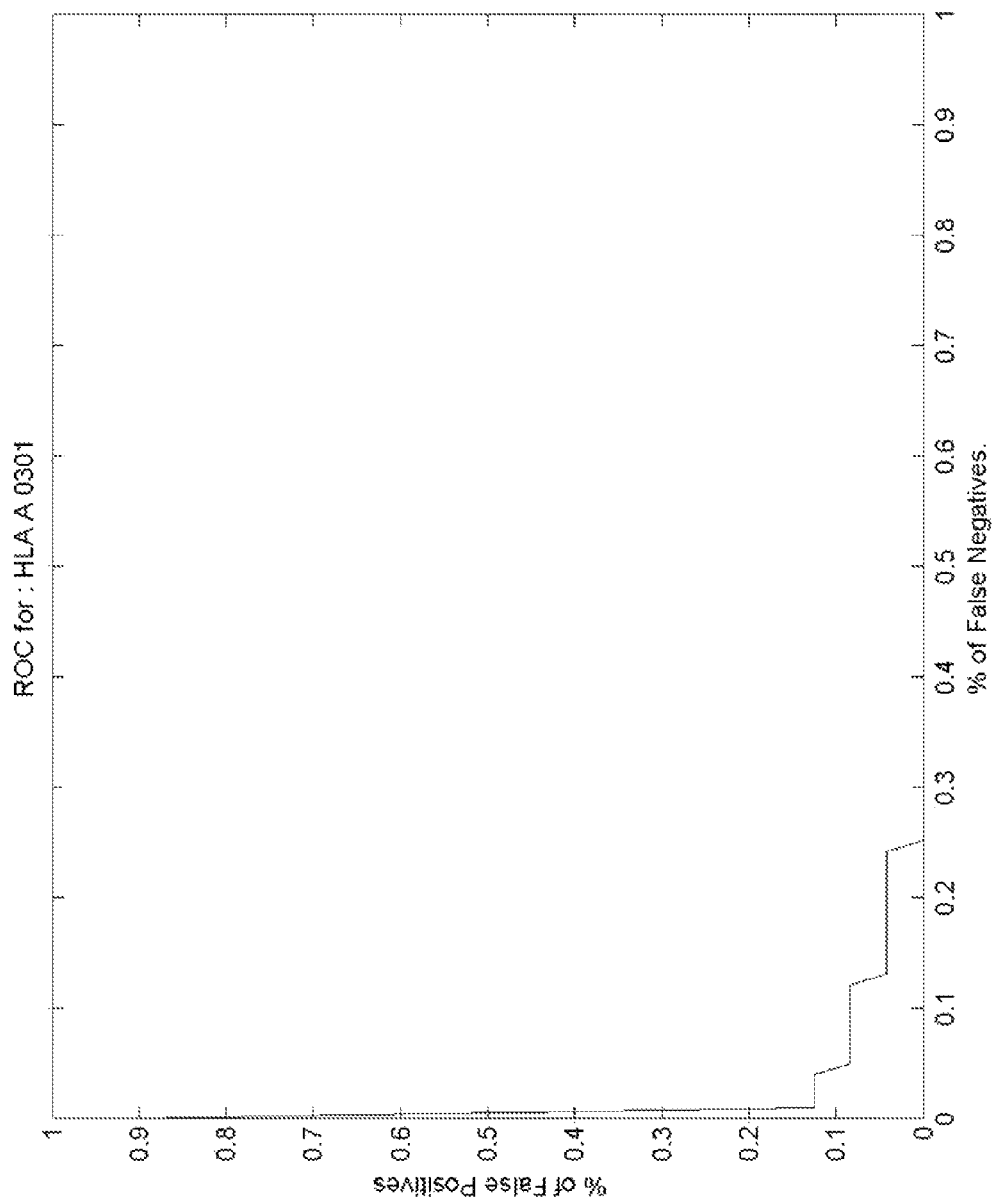
Figure 19D:
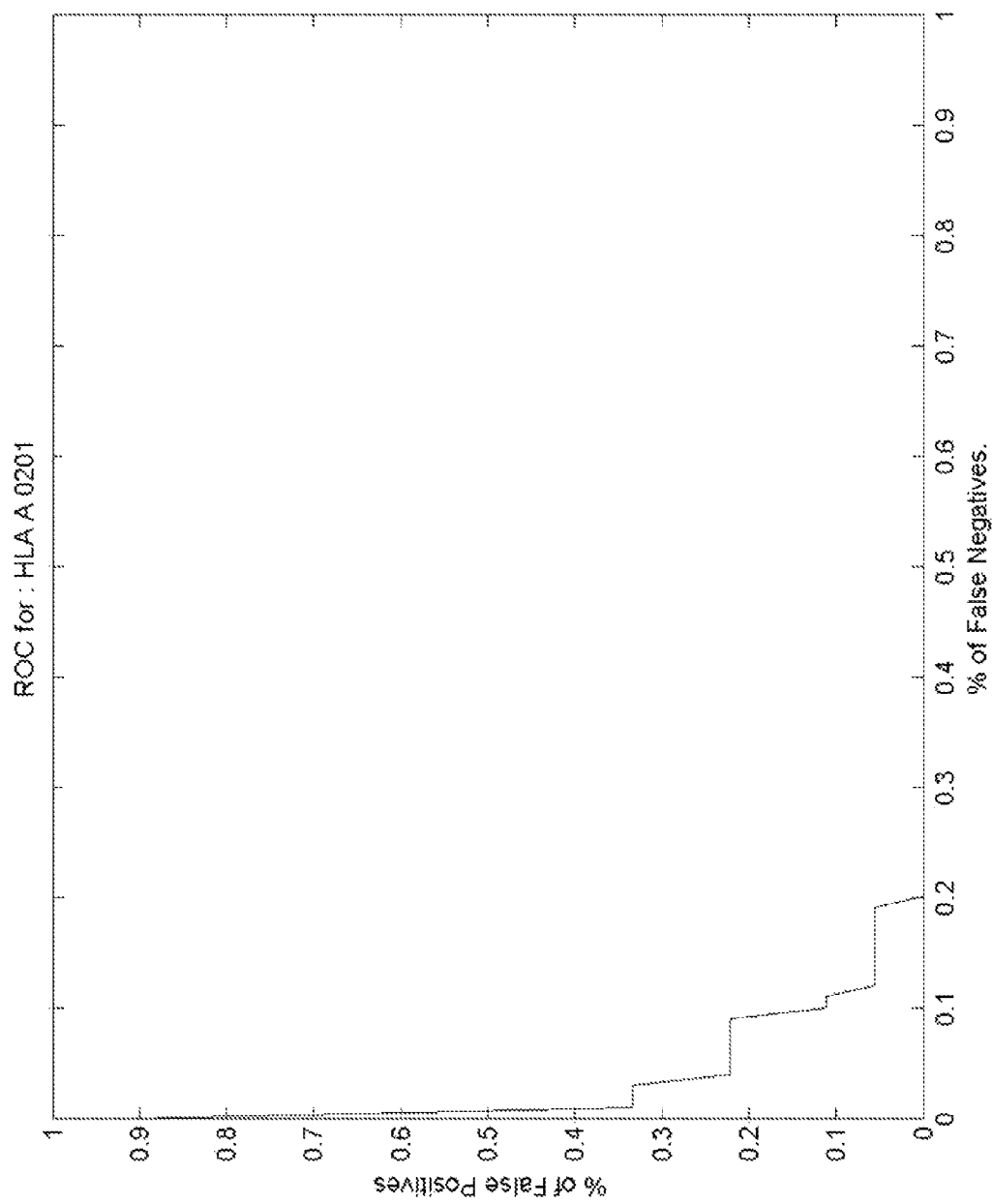
Figure 19E:
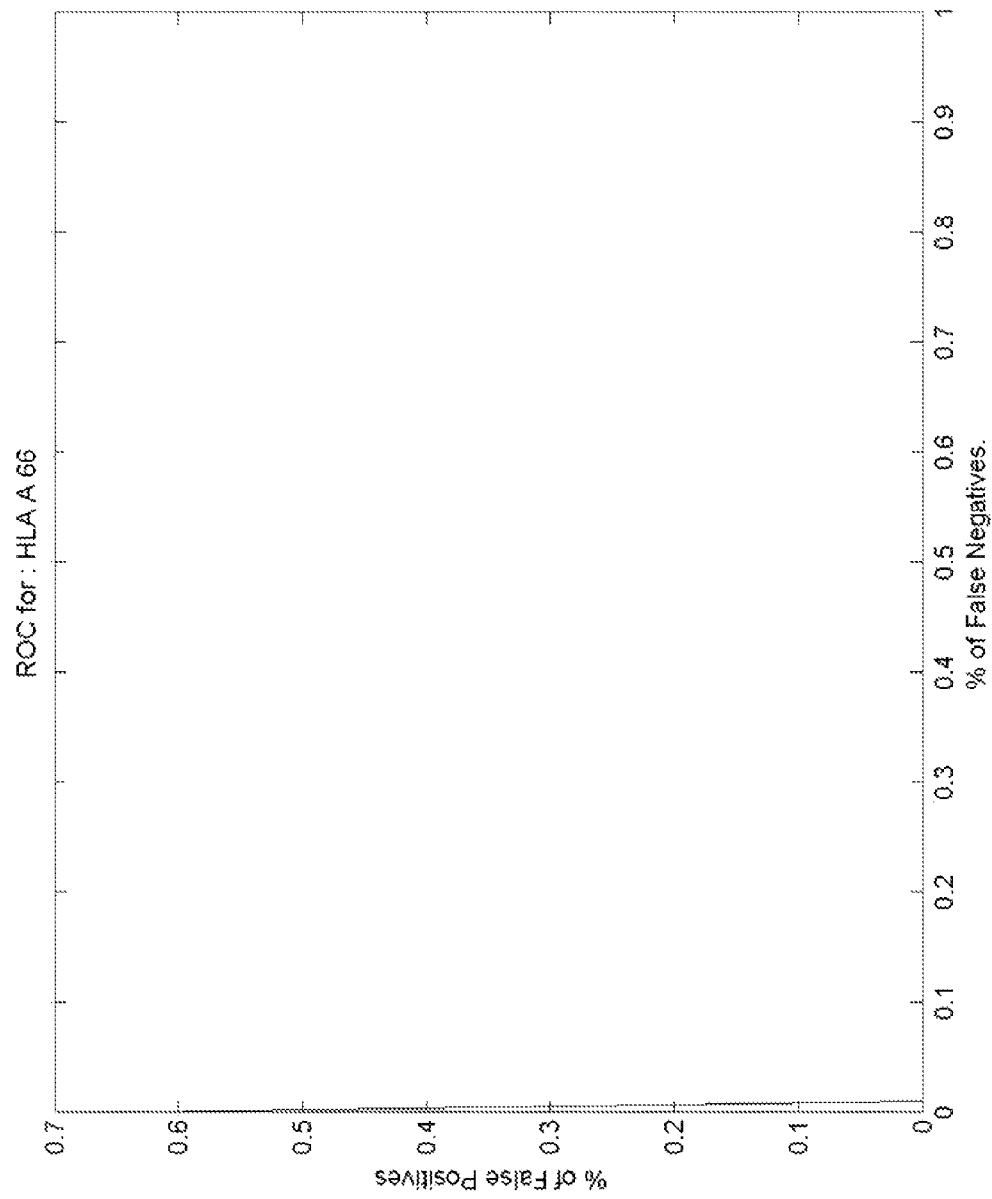
Figure 19F:
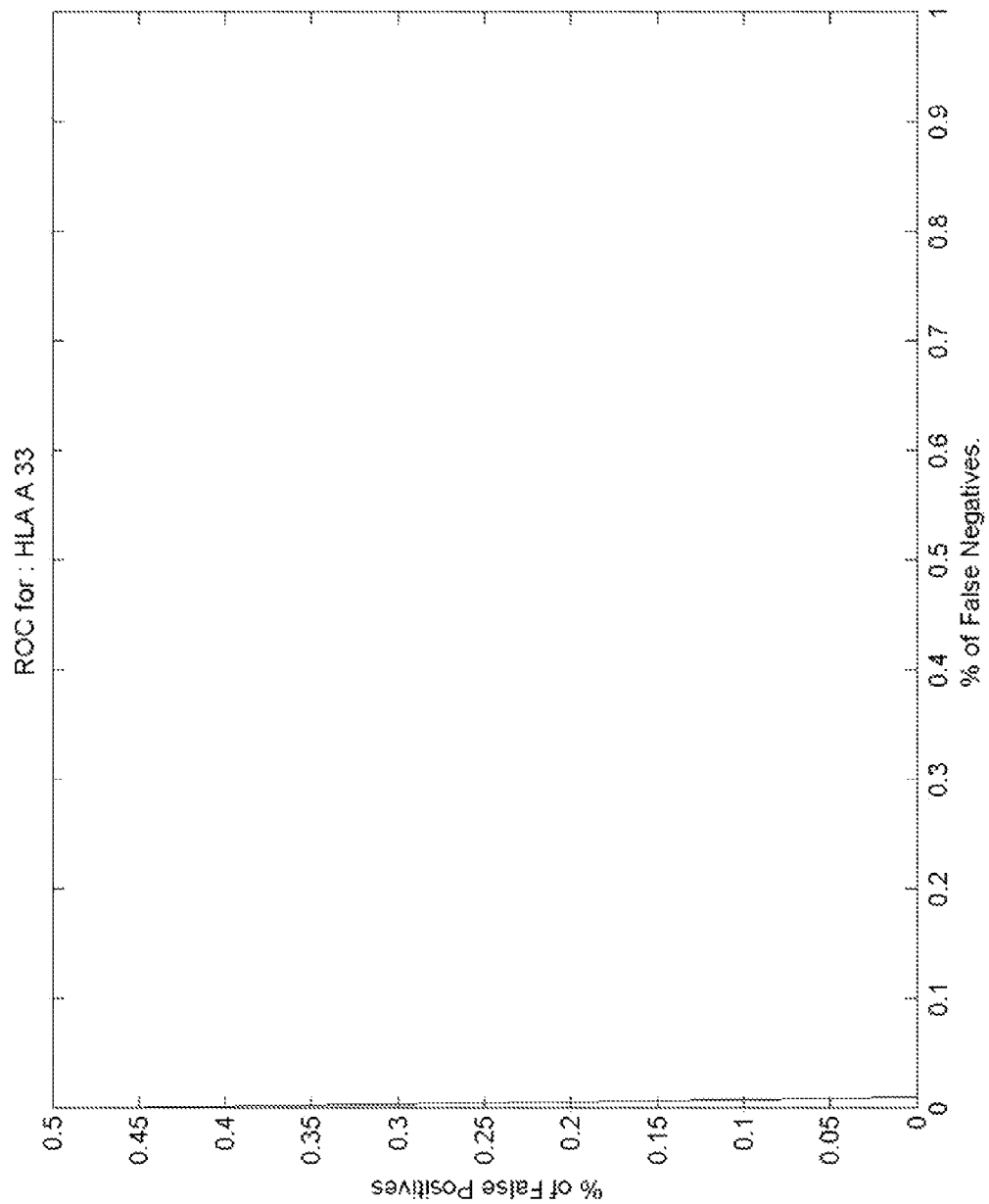
Figure 20A:
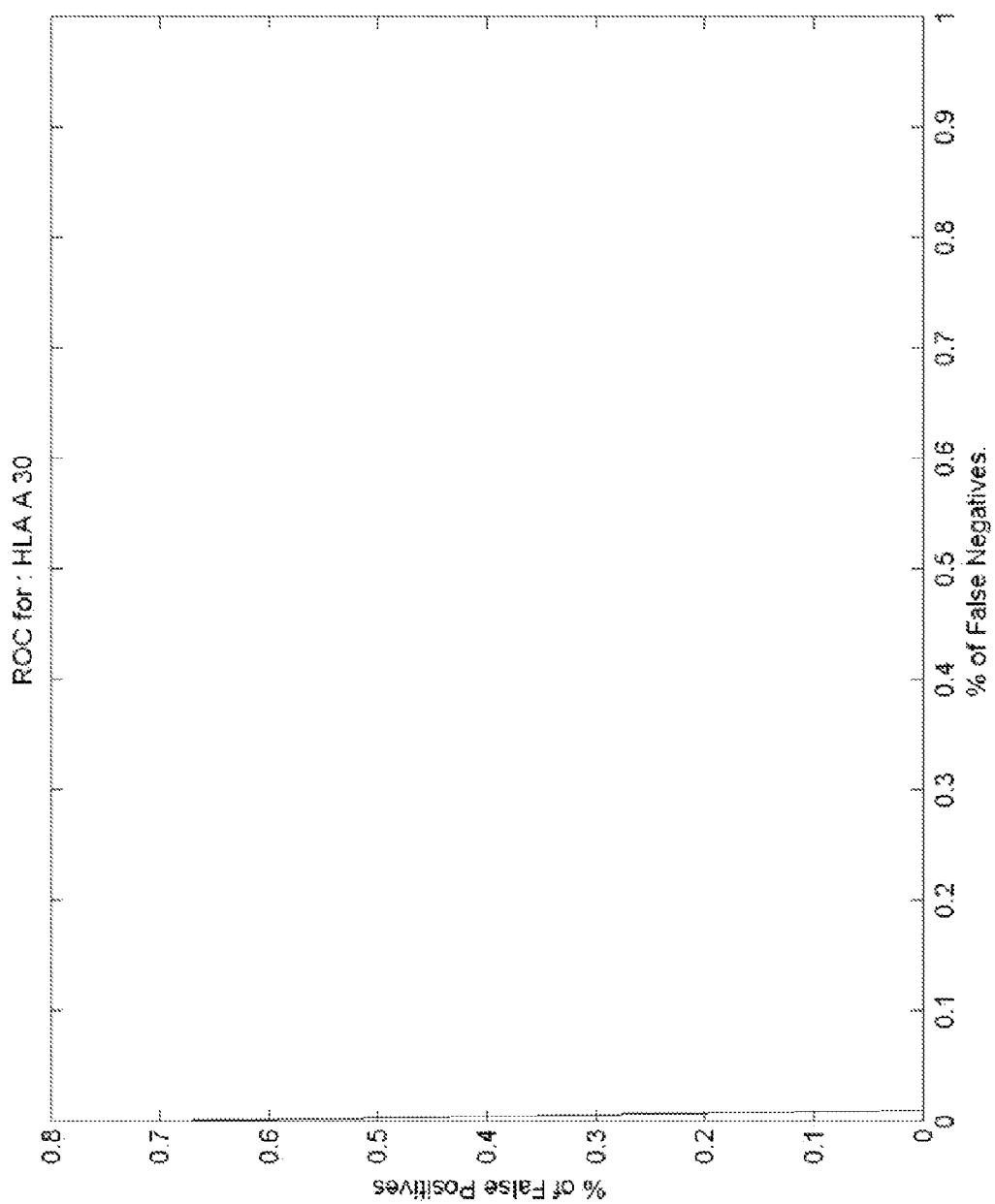
FIGS. 20a-f show ROC curves demonstrating the performance of an adaptive threading predictor trained on data from over 50 MHC molecules.
Figure 20B:
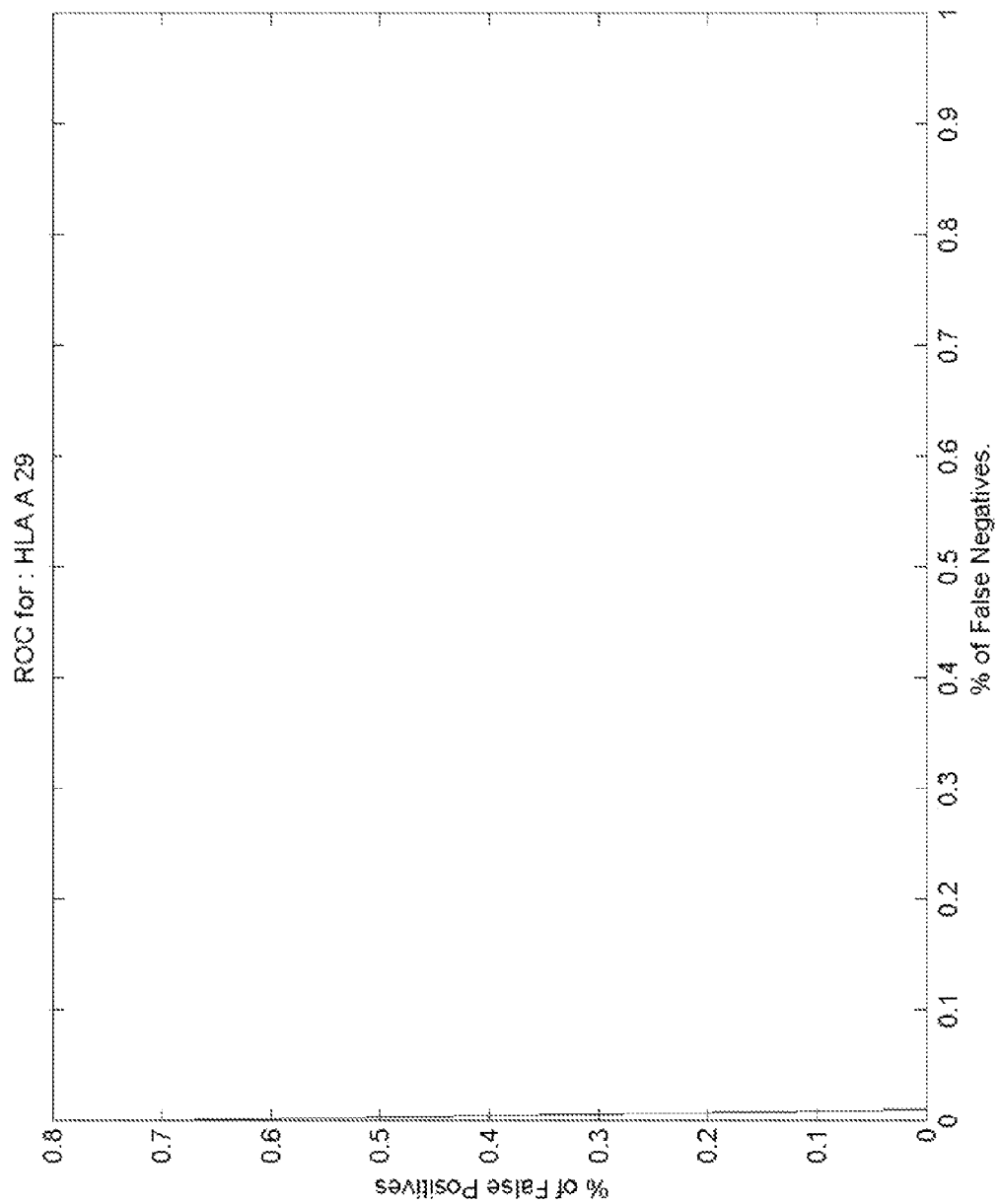
Figure 20C:
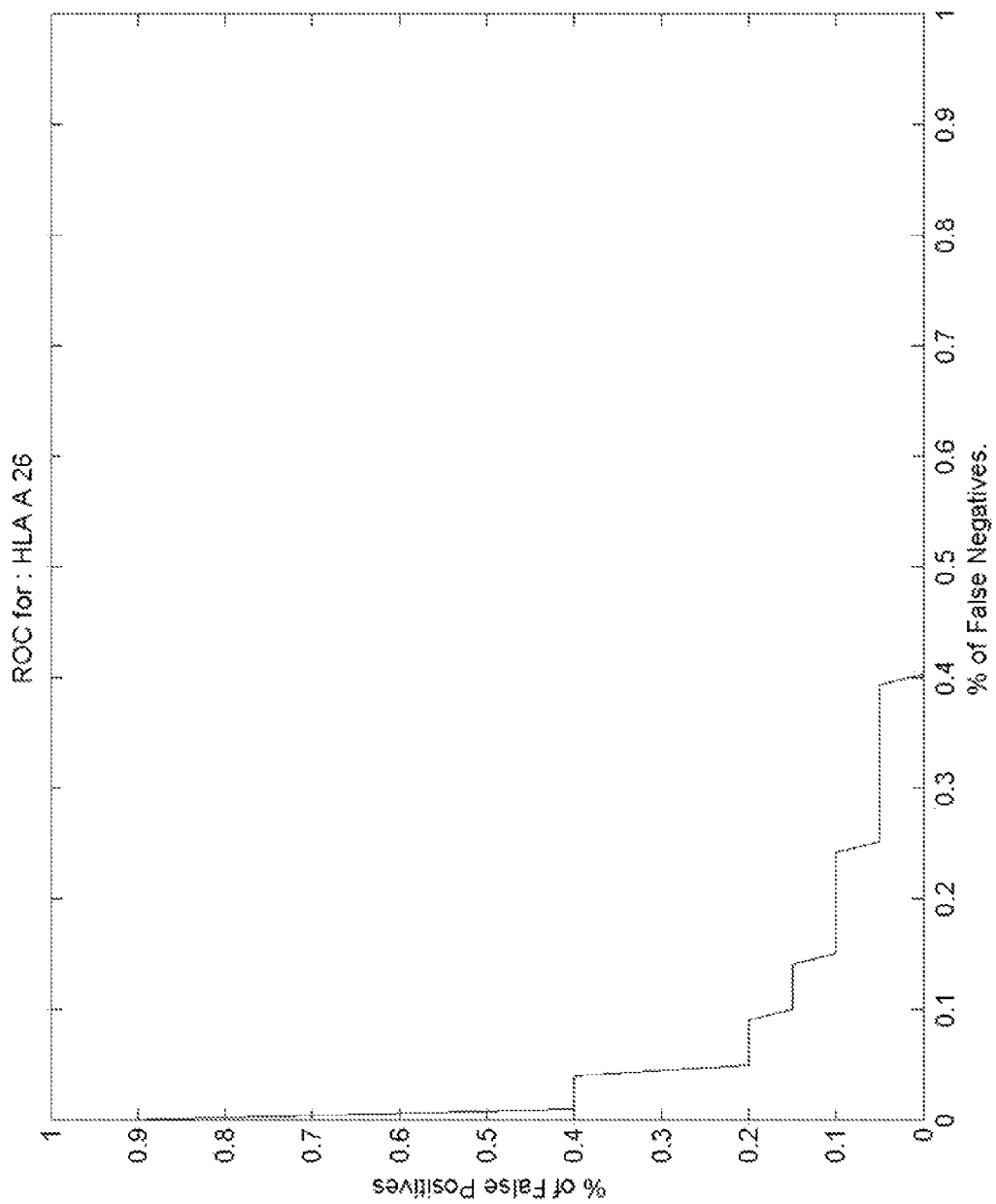
Figure 20D:
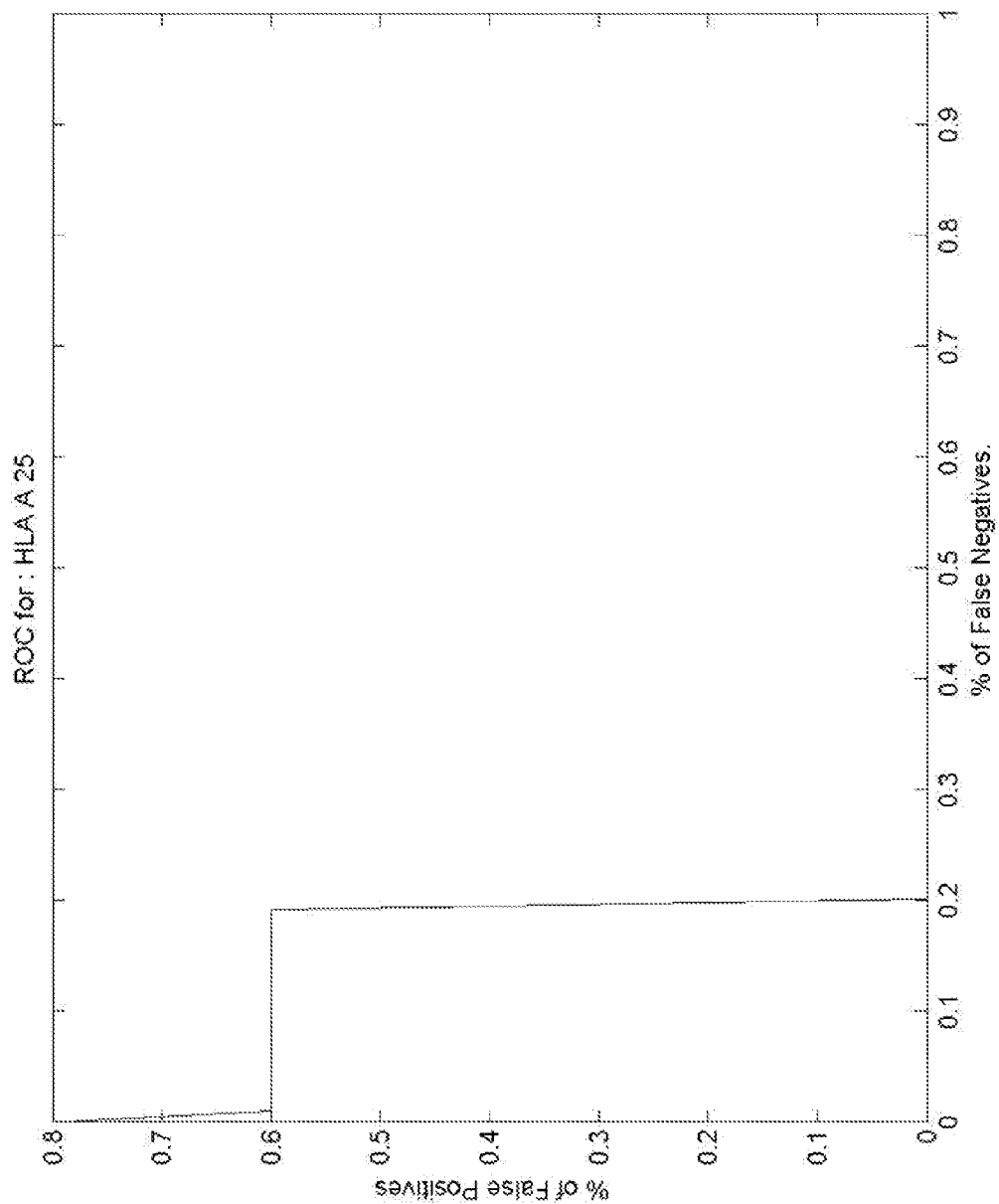
Figure 20E:
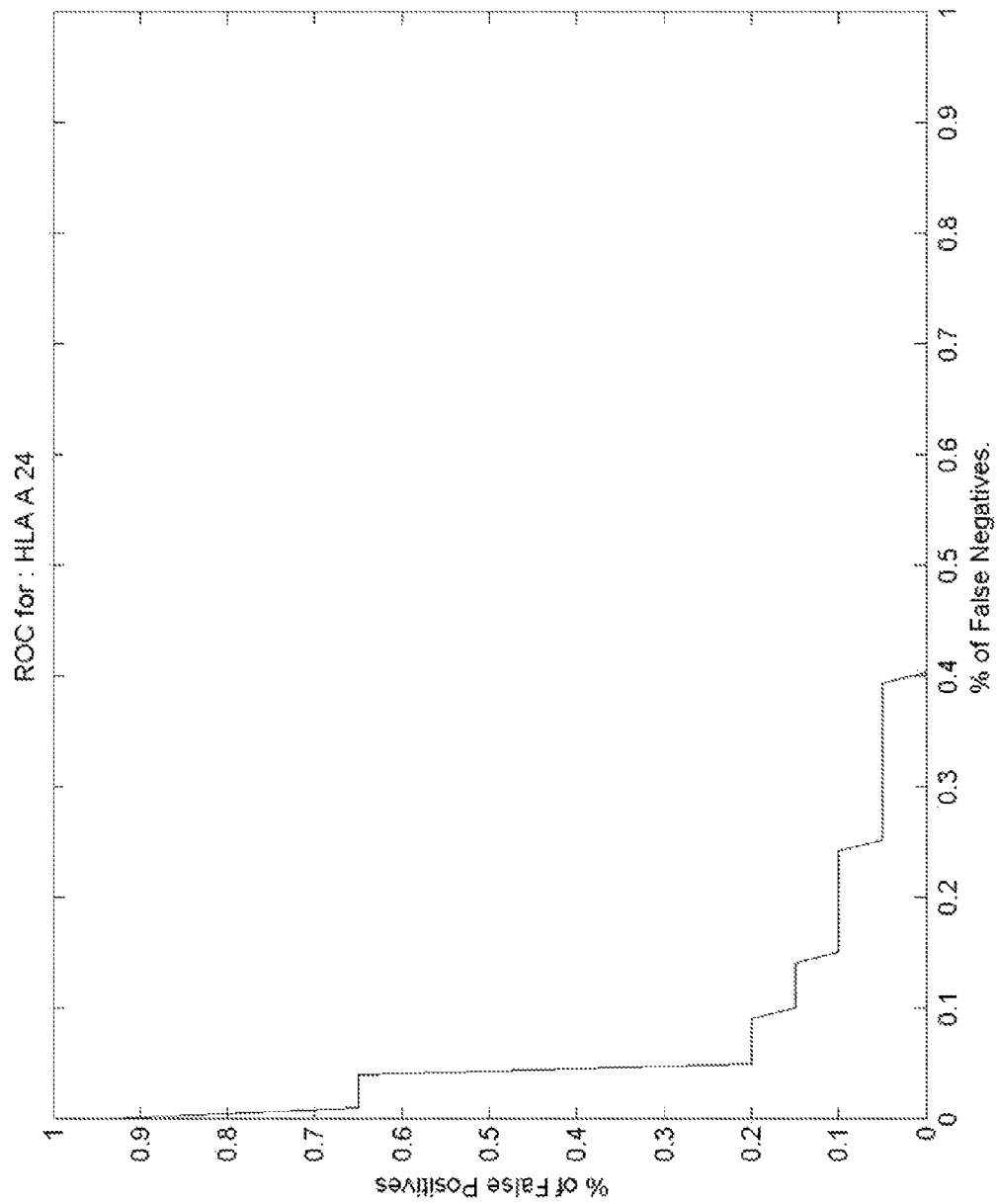
Figure 20F:
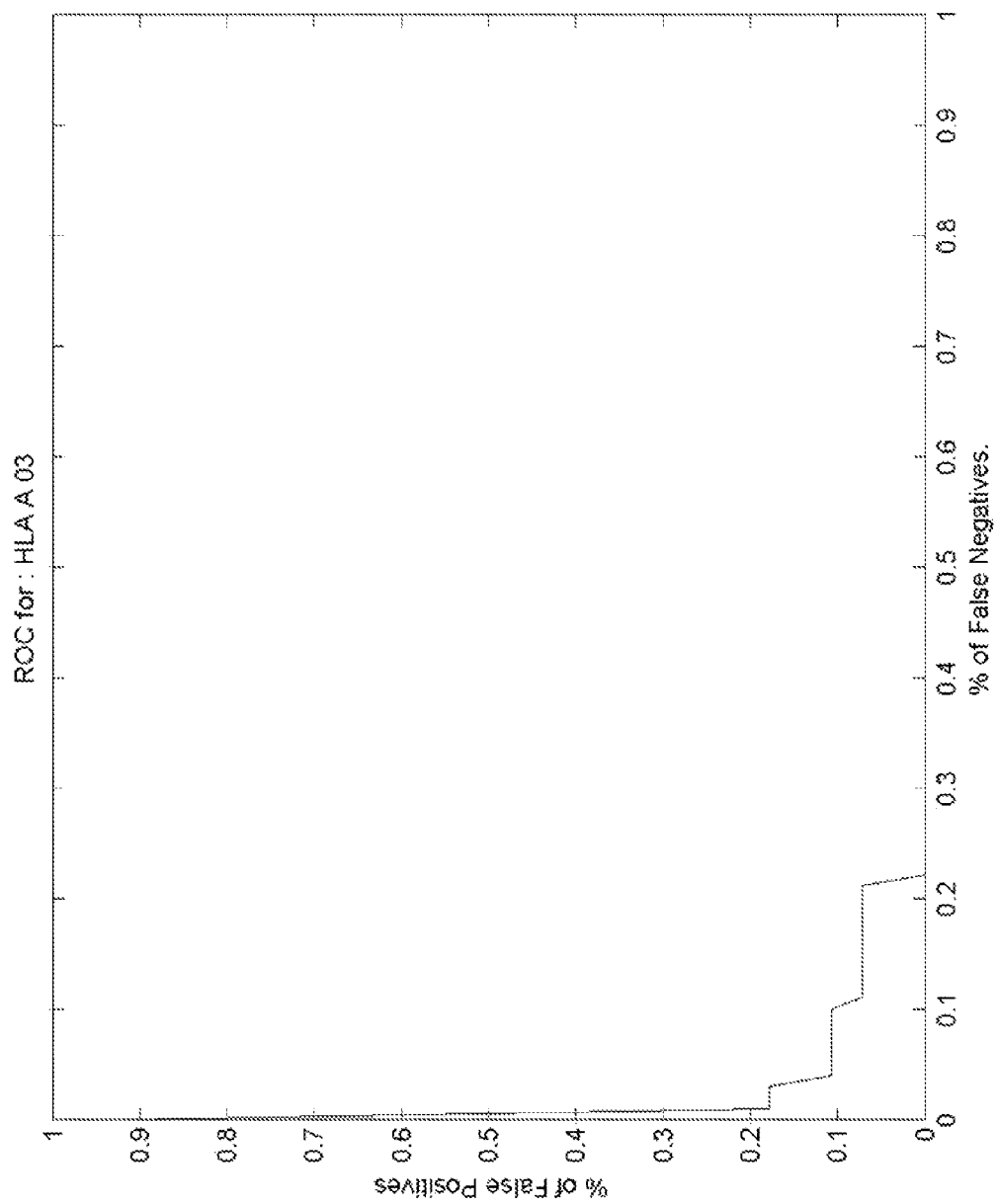
Figure 21A:
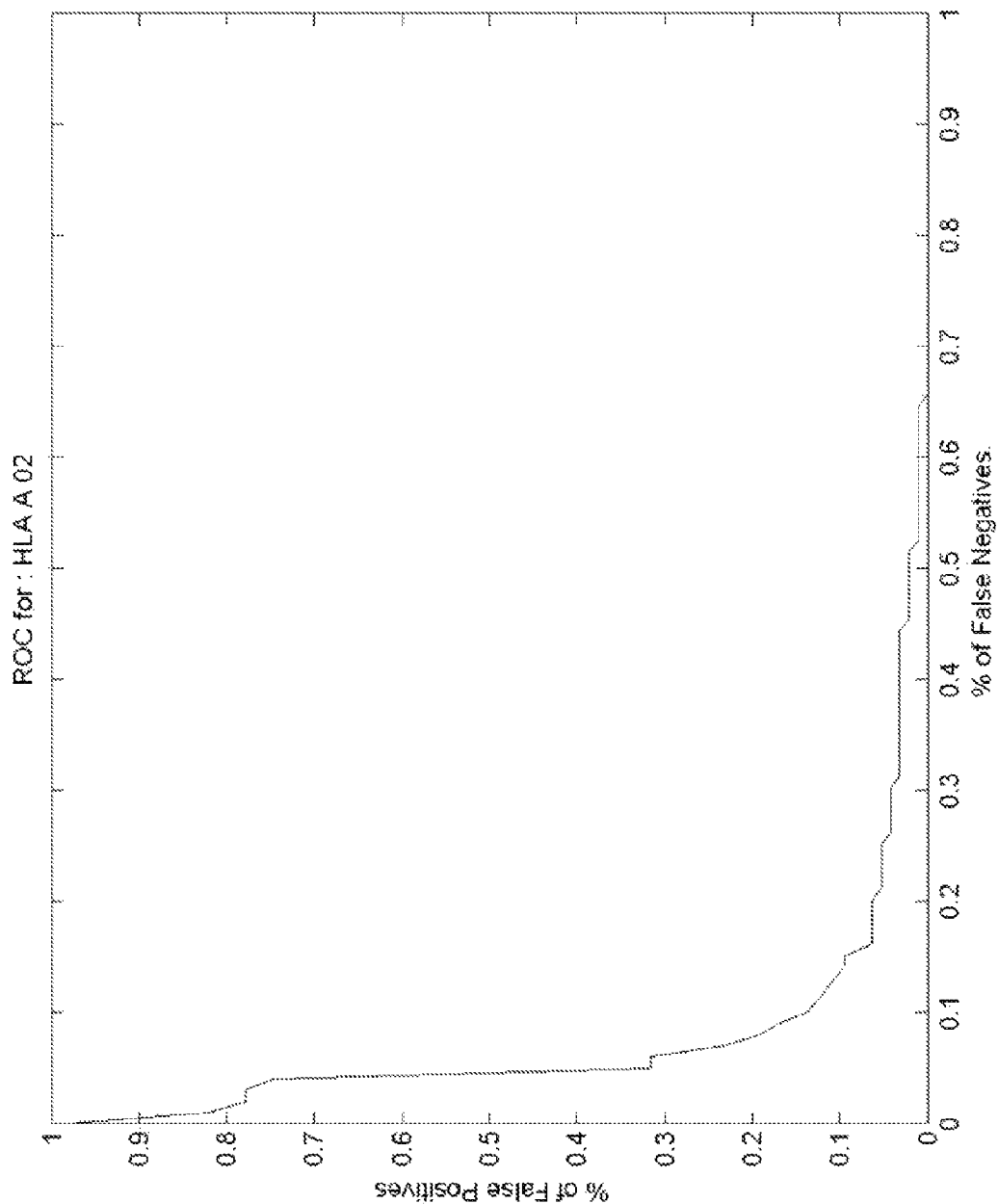
FIGS. 21a-b show ROC curves demonstrating the performance of an adaptive threading predictor trained on data from over 50 MHC molecules.
Figure 21B:
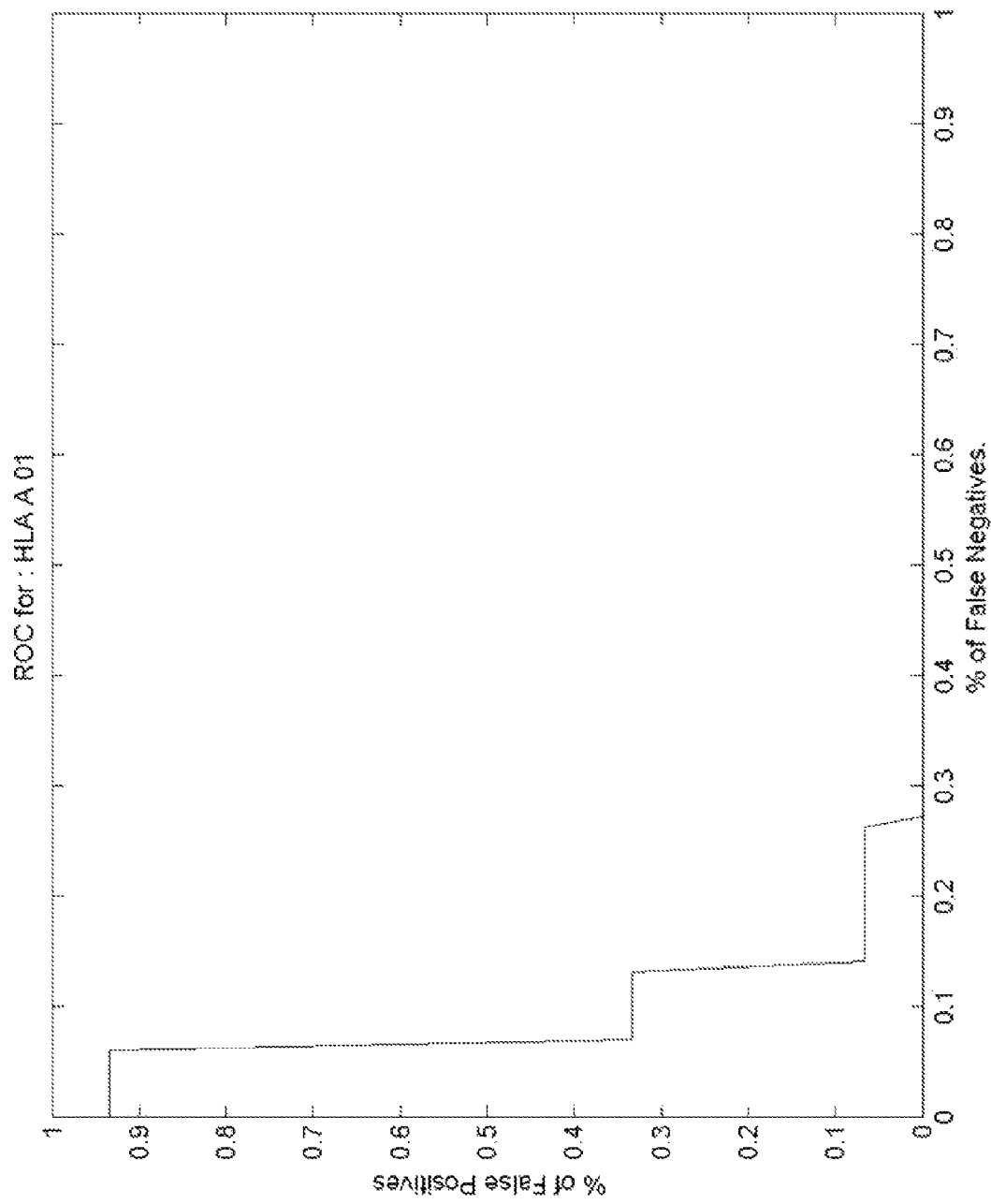

FIG. 8 shows a system 800 for determining the binding free energies of protein-protein complexes. Machine learning means 810 estimating amino acid contact potentials and their corresponding weights from at least some of the data that is available. Machine learning means 820 determines a binding free energy of one protein (e.g., an MHC molecule) to another protein (e.g., an 8-11 amino acid long peptide) utilizing an optimized soft step function 830 defining an amino acid distance criterion, the amino acid contact potentials and their corresponding weights. The machine learning means 810 and 820 can be, for instance, any of the machine learning means described in reference to FIGS. 2-7 above.

The following examples are provided for the purpose of demonstrating utility. Although MHC-peptide binding energies have been selected to illustrate how the subject matter can be employed, the claimed subject matter facilitates making predictions about any molecular complex and is not limited to predicting MHC-peptide binding energies.

EXAMPLE 1

A bilinear predictor having a soft step distance function and hidden variable m as described in detail above was used to predict molecular interactions. Data to train and validate the model included 37 structural data files obtained from the RCSB protein data bank, experimentally obtained binding energies of 870 different MHC-peptide combinations and binary information on known good binders (epitopes) and nonbinders from the SYFPEITHI database, the Los Alamos National Laboratory HIV Database and the MHCBN Database. The binary energy data is data that indicates if a peptide is a strong binder with very low binding energy, or a nonbinder with very high binding energy for a particular MHC type without providing the exact energy of binding.

The range of experimental binding energies (or equivalently IC50 ratios, the negative log of which corresponds to energy) for peptides used in the experiments was large and only some of the peptides exhibited very high energies (epitopes). The peptides were divided into three categories: good binders, intermediate binders and non binders. The peptides having relative binding (IC50 ratio) above 0.1 were labeled as good binders, and those with IC50 below 0.0001 were considered non-binders. Table 1 summarizes the number of peptides for which data was available in terms of the MHC molecules, peptide lengths and the binding strength.

TABLE 1

| MHC, peptide | Good Binders | Intermediate | Non-binders |
| --- | --- | --- | --- |
| A0201, peptide length 9 | 62 | 254 | 202 |
| A0201, peptide length 10 | 27 | 138 | 100 |
| A6801, peptide length 9 | 10 | 34 | 7 |
| B2709, peptide length 9 | 11 | 11 | 14 |

In order to compare the adjusted threading method to standard threading, the performance of an adjusted predictor was evaluated in terms of peptide ranking measured by Spearman correlation factor. The Spearman correlation factor varies between −1 and 1. Values close to 1 indicate that the ranking of peptides according to the predicted energies is similar to a ranking according to the experimentally measured energies.

To train and test the model, the data was divided 100 times into random training/testing partitions such that 70% of the data was used for training and the remainder used to validate the model. The data distribution for both sets was kept similar to that of Table 1. Table 2 shows the average performance as well as the standard deviation across the experiments and shows that the trained, bilinear model clearly outperforms regular threading on this dataset.

TABLE 2

| MHC, peptide | Standard Threading Model | Trained Adjusted Threading Model | Standard Deviation |
| --- | --- | --- | --- |
| A0201, peptide length 9 | 0.46 | 0.78 | 0.03 |
| A0201, peptide length 10 | 0.56 | 0.82 | 0.03 |
| A6801, peptide length 9 | 0.16 | 0.67 | 0.13 |
| B2709, peptide length 9 | 0.40 | 0.71 | 0.09 |

In order to evaluate the performance of both of the adjusted models (i.e., one with MHC-dependent weights and one with MHC-independent weights) on the data for which only binary energies are known, the entire set of measured binding energies, all available 3-D structures, and some of the binary data were used for training, and the rest of the binary data was used for testing. The training and testing sets were chosen randomly 10 times. The training set spanned 9 MHC types (A0201, A6801, B2705, A1101, B3501, B5301, A0301, B4402, and B0702), and the peptides had lengths of 9-10 amino acids.

Since both the standard threading model and the trained adjusted threading models output a binding energy and not a binary decision, the two were compared in terms of Receiver Operating Characteristics (ROC) curves. The ROC curves were obtained by using test data from the SYFPEITHI database, varying the good-binder (epitope) threshold (i.e., the cut-off value for classifying a peptide as an epitope) and measuring the number of false positives and false negatives. The standard threading model employed two previously published pairwise contact potential matrices (Miy and Bet published in S. Miyazawa and R. L. Jernigan, "Residue-residue potentials with a favorable contact pair term and an unfavorable high packing density term for simulation and threading," J. Mol. Biol. (1996) 256:623-644 and M. R. Betancourt and D. Thirumalai, "Pair potentials for protein folding: Choice of reference states and sensitivity of predicted native states to variations in the interaction schemes," Protein Sci. (1999) 8:361-369, respectively).

As shown in the ROC curves of FIGS. 9a-12e, both of the adjusted threading models (Bil) significantly outperformed standard threading. Of particular note, for A0301 and B0702, the crystal structures were not available. Using the amino acid content of the MHC molecule, an analogous MHC molecule with available crystal structure was inferred. This approach still resulted in improved performance compared to the standard threading model.

FIGS. 13a-14d show ROC curves demonstrating the ability of both of the above trained models (i.e., the MHC-specific and MHC-independent trained models producing the ROC curves shown in FIGS. 9a-12e) to predict binding energies for 4 MHC molecules that were not part of the training set (A6801, B1508, B5301 and CW0401). This model transfer was conducted using the parameters m and distance d for the MHC molecule used during training that had the closest sequence to that of the MHC molecule under study. As shown in the ROC curves of FIGS. 13a-14d, both of the trained adjusted models outperformed the standard threading model.

Figure 22:
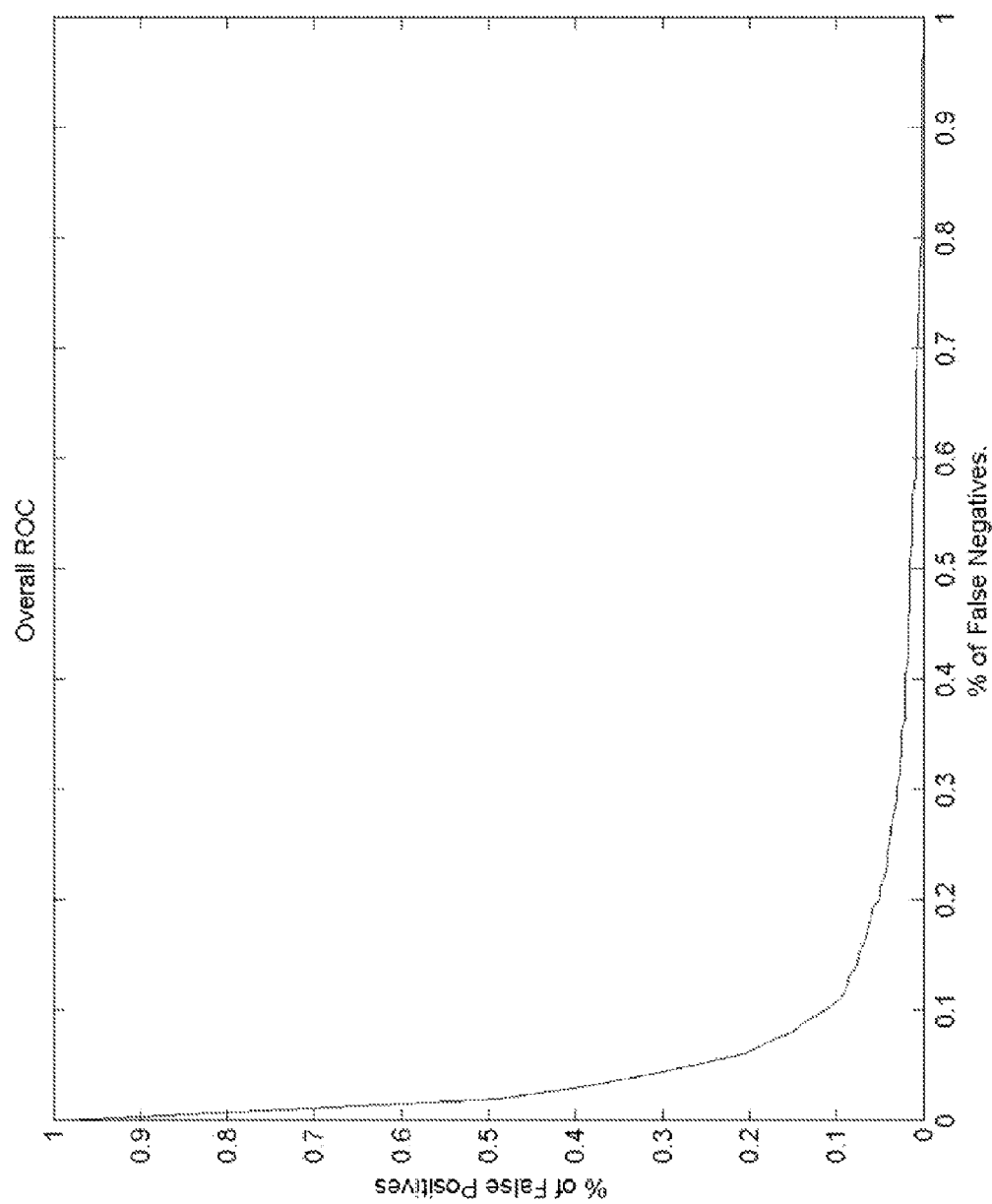
FIG. 22 is an overall ROC curve demonstrating the performance of an adaptive threading predictor trained on data from over 50 MHC molecules.

FIGS. 15a-21b show ROC curves demonstrating the performance of an adaptive threading predictor trained on data from 53 MHC molecules. FIG. 22 is an overall ROC curve demonstrating the overall performance of the adaptive threading predictor trained on 53 MHC molecules. The overall ROC shows the performance of the energy predictions for all of the peptides and all of the MHC types tested. The 53 MHC molecules used to train the model were A0201, B2705, A1101, B3501, B5101, B4402, A0301, B0702, A02, B57, B53, B1509, C04, A30, B51, A03, B07, A24, A6802, B1501, C08, B27, B08, A26, A01, A29, B40, A11, B45, A6801, B18, B1510, A31, B37, A25, B1513, B39, B58, B14, B1516, B38, B35, A66, B1502, B52, B44, B1517, B55, C07, C01, C03, B1508, and A33.

EXAMPLE 2

The adaptive binding energy predictor described above was used to study viral infections in 246 HIV patients from the West Australian (WA) cohort, and over 1000 sequences in HIV clade B from Los Alamos National Laboratory database, which capture the course of HIV evolution over the last 20 years. The results of the study illustrate short, medium, and long-term adaptation of HIV to the human immune system.

Using the bilinear adjusted threading model with a soft step distance function and hidden variable m, the average binding energy of all HIV 9mers taken from the current consensus sequence for lade B (starting from each site in each protein) was computed to be 9.74. In comparison, the average binding energy in a randomized HIV sequence (i.e., HIV sequence containing the same set of proteins having the same lengths but with random amino acid content) is 9.3. The difference in average binding energies has a very strong statistical significance ($p < 10^{-5}$ based on 50 different randomizations), and can be explained by viral evolution (i.e., higher average binding energy translates into a smaller total number of presented peptides which trigger immune reaction). Similar patterns should be expected from other viruses that are variable enough to use mutation as an escape mechanism and even possible that less variable viruses evolving over a very long time, may exhibit the same evolution over time.

It previously has been shown that some HIV mutations correlate with MHC types of the host. The adjusted binding energy estimators aides in explaining these correlations. FIG. 23A shows a significant correlation ($p < 0.05$) between the average A0201 binding energy and viral load in HIV positive patients having HLA type A0201 (i.e., A0201 positive) from the WA cohort. As would be expected, in A0201 negative patients, no correlation was found. Each patient's HIV was sequenced providing a source of 9mers and 10mers. In FIG. 23A, each chronically infected and untreated A0201 positive patient in the cohort is represented by a dot with coordinates equal to the patient's viral load and the sum of 9mer and 10mer average binding energies for A0201.

A viral strain coding for peptides that bind well to a particular MHC molecule and infecting an individual with that particular MHC type is typically under strong immune pressure to mutate away from its fittest form towards a form that binds less well to that particular MHC. However, as HIV damages the individual's immune system, the pressure to escape the particular MHC type wanes and the viral load increases. Thus, the negative trend in FIG. 16A can be explained by reversion of the viral sequence towards the wild type having higher replicative fitness and lower adaptation to A0201 in patients whose immune system is starting to fail.

Figure 23B:
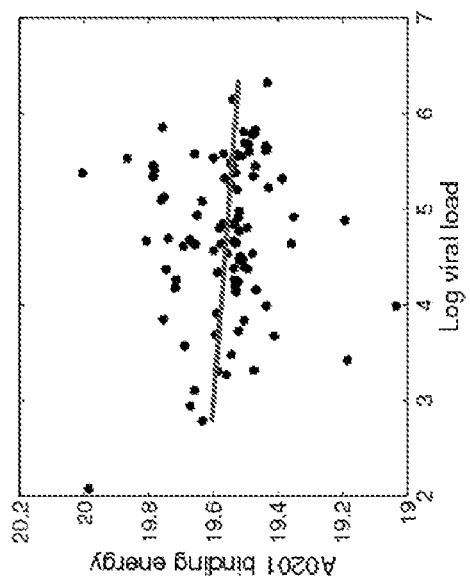
FIG. 23B is a graph showing the average binding energy of MHC A0201 to HIV peptides over the last 23 years.
Figure 23A:
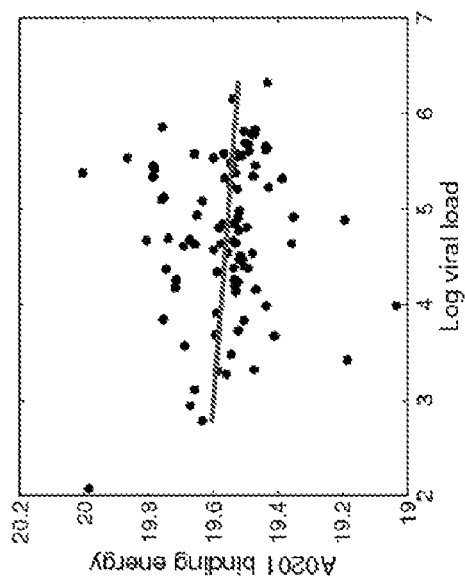
FIG. 23A is a graph showing HIV peptide-MHC A0201 binding energy trends as a function of viral load in individual's infected with HIV.

FIG. 23B shows the average binding energy of MHC A0201 to HIV peptides over the last 23 years. The HIV sequences were obtained from the Los Alamos National Laboratory database. To smooth out the sampling density over time, all sequences were grouped into 3 year time intervals (i.e., 1982-1984, 1985-1987, . . . , 2003-2005). The apparent upward trend is statistically weak, but could indicate that HIV as a population is adapting to the immune systems of the host population. The recent trend of HIV fitness attenuation that has been noted is consistent with this observation.

Thus, the examples provided above show that an adjusted threading model of MHC-peptide binding can be used to estimate a high range of binding energies for high resolution MHC types (four digits, based on MHC sequencing). Both in terms of peptide ranking and binary classification performance, the adjusted model significantly outperforms the standard threading model. The increased predictive power of the adjusted model facilitates capturing pathogen evolution patterns (e.g., escape mutations, immunodominance, etc.) in response to the immune pressure of the host (whereas the standard threading model did not show statistically significant trends). The adjusted model also can be used to provide binding energies for epitome learning Epitome learning is described elsewhere (see, N. Jojic, V. Jojic, B. Frey, C. Meek, and D. Heckerman, "Modeling genetic diversity with epitomes: Rational design of HIV vaccine cocktails," $19^{th}$ Annual Conference on Neural Information Processing Systems, Dec. 5-10,2005.

Figure 24:
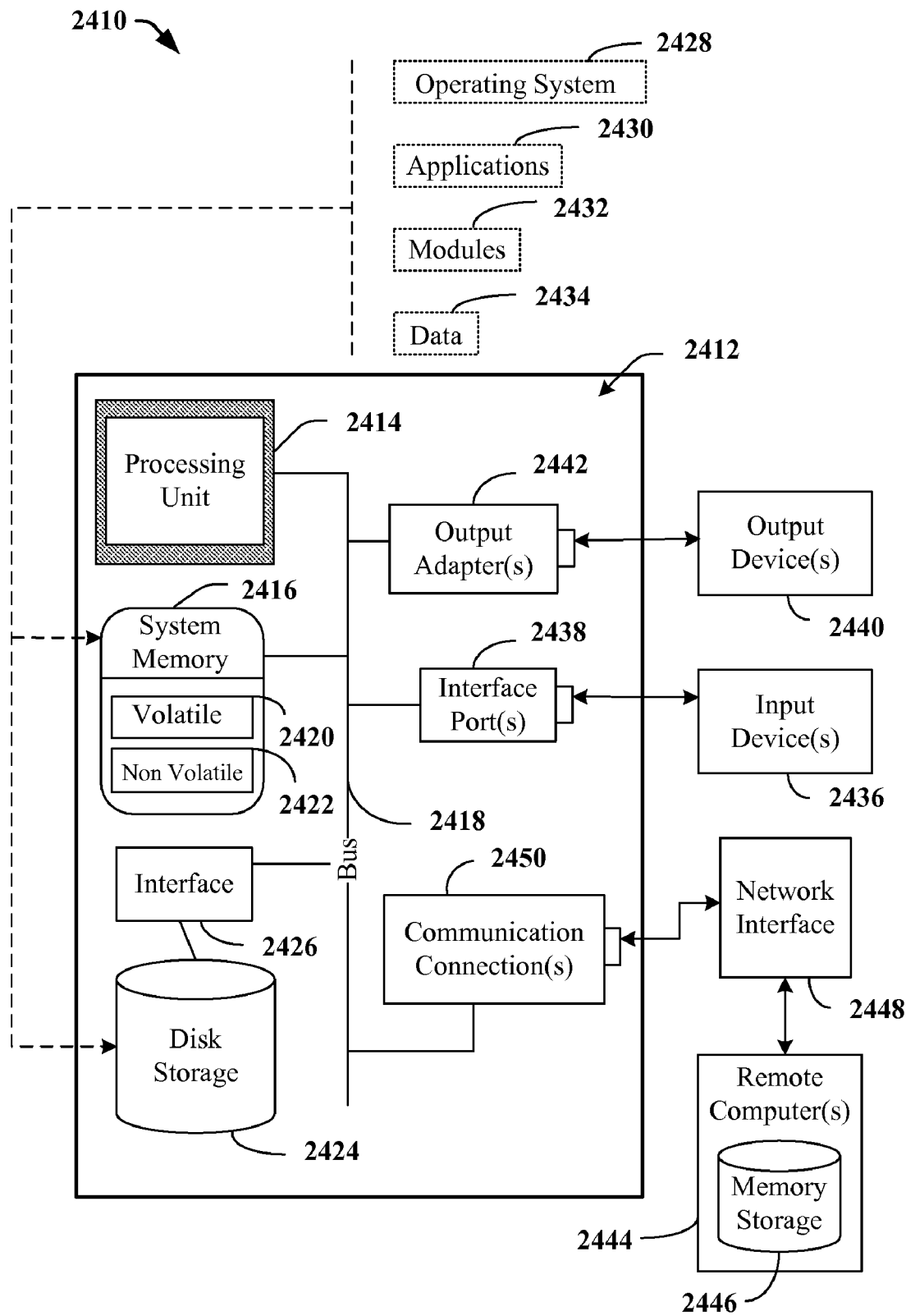
FIG. 24 schematically illustrates an exemplary computing architecture.
Figure 25:
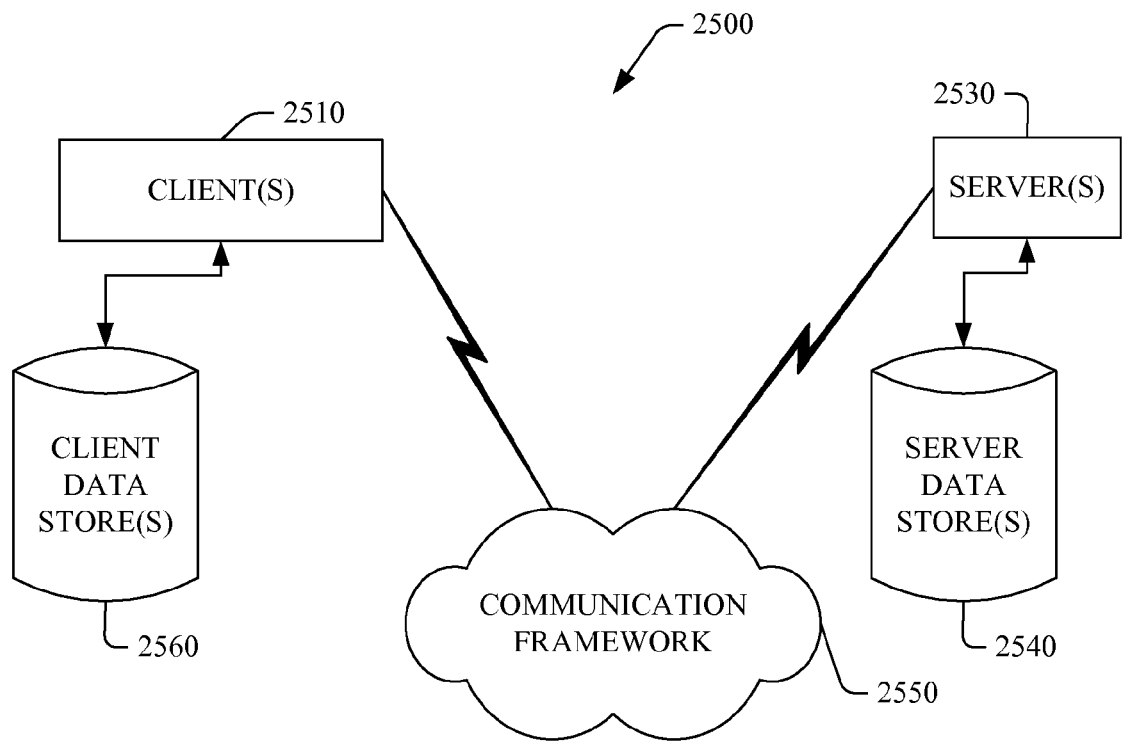
FIG. 25 schematically illustrates an exemplary networking environment.

FIGS. 24-25 and the following discussion are intended to provide a brief, general description of a suitable computing environment in which the various aspects of the subject matter can be implemented. While the subject matter has been described above in the general context of computer-executable instructions of a computer program that runs on a local computer and/or remote computer, the subject matter also can be implemented in combination with other program modules.

Moreover, the subject matter can be practiced with other computer system configurations, including single-processor or multi-processor computer systems, minicomputers, mainframe computers, as well as personal computers, hand-held computing devices, microprocessor-based and/or programmable consumer electronics and the like, each of which may operatively communicate with one or more associated devices. The subject matter also can be practiced in distributed computing environments such that certain tasks are performed by remote processing devices that are linked through a communications network. In a distributed computing environment, program modules may be located in local and/or remote memory storage devices. However, some, if not all, of the subject matter can be practiced on stand-alone computers.

The subject matter can operate in the general context of computer-executable instructions, such as program modules, executed by one or more components. Generally, program modules include routines, programs, objects, data structures, etc., that perform particular tasks or implement particular abstract data types. Typically, the functionality of the program modules may be combined or distributed as desired. The subject matter can be embodied on a computer-readable medium having computer-executable instructions or transmitted as signals manufactured to transmit such instructions as well as the results of performing the instructions, for instance, on a network.

FIG. 24 schematically illustrates an exemplary environment 2410 for implementing various aspects of the subject matter. The environment 2410 includes a computer 2412, which includes a processing unit 2414, a system memory 2416 and a system bus 2418. The system bus 2418 couples system components including, but not limited to, the system memory 2416 to the processing unit 2414. The processing unit 2414 can be any of various available processors. Dual microprocessors and other multiprocessor architectures also can be employed as the processing unit 2414.

The system bus 2418 can be any of several types of bus structure(s) including the memory bus or memory controller, a peripheral bus or external bus, and/or a local bus using any variety of available bus architectures including, but not limited to, 10-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI).

The system memory 2416 includes volatile memory 2420 and nonvolatile memory 2422. The basic input/output system (BIOS) containing the basic routines to transfer information between elements within the computer 2412, such as during start-up, is stored in nonvolatile memory 2422. By way of illustration, and not limitation, nonvolatile memory 2422 can include read only memory (ROM), programmable ROM (PROM), electrically programmable ROM (EPROM), electrically erasable programmable ROM (EEPROM), or flash memory. Volatile memory 2420 includes random access memory (RAM), which can act as an external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and Rambus Direct RAM (RDRAM), direct Rambus dynamic RAM (DRDRAM), and Rambus dynamic RAM (RDRAM).

Computer 2412 also includes removable/non-removable, volatile/non-volatile computer storage media. FIG. 24 illustrates, for example a disk storage device 2424. Disk storage device 2424 includes, but is not limited to, devices like a magnetic disk drive, floppy disk drive, tape drive, Jaz drive, Zip drive, LS-100 drive, flash memory card, or memory stick. In addition, disk storage device 2424 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 2424 to the system bus 2418, a removable or non-removable interface is typically used such as interface 2426.

In addition to hardware components, FIG. 24 illustrates software that acts as an intermediary between users and the basic computer resources described in suitable operating environment 2410. Such software includes an operating system 2428. Operating system 2428, which can be stored on disk storage devices 2424, acts to control and allocate resources of the computer system 2412. System applications 2430 take advantage of the management of resources by operating system 2428 through program modules 2432 and program data 2434 stored either in system memory 2416 or on disk storage devices 2424. The subject matter can be implemented with various operating systems or combinations of operating systems.

A user enters commands or information into the computer 2412 through input device(s) 2436. Input devices 2436 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 2414 through the system bus 2418 via interface port(s) 2438. Interface port(s) 2438 include, for example, a serial port, a parallel port, a game port, and a universal serial bus (USB). Output device(s) 2440 use some of the same type of ports as input device(s) 2436. Thus, for example, a USB port may be used to provide input to computer 2412 and to output information from computer 2412 to an output device 2440. Output adapter 2442 is provided to illustrate that there are some output devices 2440 like monitors, speakers, and printers, among other output devices 2440, which require special adapters. The output adapters 2442 include, by way of illustration and not limitation, video and sound cards that provide a means of connection between the output device 2440 and the system bus 2418. It should be noted that other devices and/or systems of devices provide both input and output capabilities such as remote computer(s) 2444.

Computer 2412 can operate in a networked environment using logical connections to one or more remote computers, such as remote computer(s) 2444. The remote computer(s) 2444 can be a personal computer, a server, a router, a network PC, a workstation, a microprocessor based appliance, a peer device or other common network node and the like, and typically includes many or all of the elements described relative to computer 2412. For purposes of brevity, only a memory storage device 2446 is illustrated with remote computer(s) 2444. Remote computer(s) 2444 is logically connected to computer 2412 through a network interface 2448 and then physically connected via communication connection 2450. Network interface 2448 encompasses communication networks such as local-area networks (LAN) and wide-area networks (WAN). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 2450 refers to the hardware/software employed to connect the network interface 2448 to the bus 2418. While communication connection 2450 is shown for illustrative clarity inside computer 2412, it can also be external to computer 2412. The hardware/software necessary for connection to the network interface 2448 includes, for exemplary purposes only, internal and external technologies such as, modems including regular telephone grade modems, cable modems and DSL modems, ISDN adapters, and Ethernet cards.

FIG. 25 is a schematic block diagram of a sample computing environment 2500 with which the subject matter can interact. The system 2500 includes one or more client(s) 2510. The client(s) 2510 can be hardware and/or software (e.g., threads, processes, computing devices). The system 2500 also includes one or more server(s) 2530. The server(s) 2530 also can be hardware and/or software (e.g., threads, processes, computing devices). The servers 2530 can house threads to perform transformations by employing the subject matter.

One possible communication between a client 2510 and a server 2530 can be in the form of a data packet or signal manufactured to be transmitted between two or more computer processes. The system 2500 includes a communication framework 2550 that can be employed to facilitate communications between the client(s) 2510 and the server(s) 2530. The client(s) 2510 can connect to one or more client data store(s) 2560 that can be employed to store information local to the client(s) 2510. Similarly, the server(s) 2530 can connect to one or more server data store(s) 2540 that can be employed to store information local to the servers 2530.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It is, of course, not possible to describe every conceivable combination of components or methodologies that fall within the claimed subject matter, and many further combinations and permutations of the subject matter are possible. While a particular feature may have been disclosed with respect to only one of several implementations, such feature may be combined with one or more other features of the other implementations of the subject matter as may be desired and advantageous for any given or particular application.

In regard to the various functions performed by the above described components, computer-executable instructions, means, systems and the like, the terms are intended to correspond, unless otherwise indicated, to any functional equivalents even though the functional equivalents are not structurally equivalent to the disclosed structures. Furthermore, to the extent that the terms "includes," and "including" and variants thereof are used in either the specification or the claims, these terms are intended to be inclusive in a manner similar to the term "comprising." Accordingly, the claimed subject matter is intended to embrace all such alterations, modifications, and variations that fall within the spirit and scope of the appended claims.

What is claimed is:

1. A method executed on a processing unit, the method comprising:
    providing an optimized set of weighted contact potentials, the set of optimized weighted contact potentials optimized utilizing one or more machine learning algorithms;
    choosing a set of distances according to a structural template relating to a contact between a protein and a peptide, the set of distances defining minimum distances of the contact between amino acids of the protein and an amino acids of a peptide;
    determining a score that rates the contact between the protein and the peptide, the score determined by evaluating the protein sequence and peptide sequence data according to the set of distances and the optimized set of weighted contact potentials;
    inferring a hidden variable representing information about geometry of a protein-peptide complex to facilitate evaluating the contact between the protein and the peptide, wherein the inferring occurs by defining distances for the set of distances from structural data corresponding to the protein sequence; and
    utilizing the hidden variable to influence the protein sequence.

2. The method of claim 1, wherein choosing the set of distances according to the structural template relating to the protein comprises inferring an identity of the structural template by making a Bayesian inference.

3. The method of claim 2, wherein the protein is obtained by mutating a naturally occurring protein.

4. The method of claim 1, wherein the one or more machine learning algorithms comprise an iterative optimization.

5. The method of claim 4, wherein the iterative optimization is iterative least squares.

6. The method of claim 1, wherein evaluating protein sequence and peptide sequence data according to the set of distances comprises utilizing an optimized soft step distance function.

7. The method of claim 6, further comprising optimizing the soft step distance function by using a gradient descent.

8. The method of claim 1, wherein the protein is a MHC molecule and the peptide is an amino acid sequence from about 8 to about 11 amino acids in length.

9. A system comprising:
    a processing unit;
    a memory coupled to the processing unit;
    components executed on the processing unit including:
        a prediction component providing an optimized set of weighted contact potentials, the set of optimized weighted contact potentials optimized utilizing one or more machine learning algorithms;
        the prediction component choosing a set of distances according to a structural template relating to a contact between a protein and a peptide, the set of distances defining minimum distances of the contact between amino acids of the protein and amino acids of the peptide;
        the prediction component determining a score that rates the contact between the protein and the peptide, the score determined by evaluating protein sequence and peptide sequence data according to the set of distances and the optimized set of weighted contact potentials;
        an inference component inferring a hidden variable representing information about geometry of a protein-peptide complex to facilitate evaluating the contact between the protein and the peptide, wherein the inferring occurs by defining distances for the set of distances from structural data corresponding to the protein sequence; and
        the prediction component utilizing the hidden variable to influence the protein sequence.

10. The system of claim 9, wherein choosing the set of distances according to the structural template relating to the protein comprises inferring an identity of the structural template by making a Bayesian inference.

11. The system of claim 10, wherein the protein is obtained by mutating a naturally occurring protein.

12. The system of claim 9, wherein the one or more machine learning algorithms comprise an iterative optimization.

13. The system of claim 12, wherein the iterative optimization is iterative least squares.

14. The system of claim 9, wherein evaluating the protein sequence and peptide sequence data according to the set of distances comprises utilizing a soft step distance function.

15. The system of claim 14, further comprising optimizing the soft step distance function by using a gradient descent.

16. The system of claim 9, wherein the protein is a MHC molecule and the peptide is an amino acid sequence from about 8 to about 11 amino acids in length.

* * * * *